(12) United States Patent
Chahal et al.

(10) Patent No.: US 8,389,286 B2
(45) Date of Patent: Mar. 5, 2013

(54) CANCER-ASSOCIATED ANTIGEN

(75) Inventors: Francina C. Chahal, Calgary (CA);
Glen MacDonald, Winnipeg (CA);
Jeannick Cizeau, Winnipeg (CA)

(73) Assignee: Viventia Biotechnologies Inc.,
Mississauga, Ontario (CA)

( * ) Notice: Subject to any disclaimer, the term of this patent is extended or adjusted under 35 U.S.C. 154(b) by 0 days.

(21) Appl. No.: 13/094,118

(22) Filed: Apr. 26, 2011

(65) Prior Publication Data

US 2012/0058106 A1 Mar. 8, 2012

Related U.S. Application Data

(63) Continuation of application No. 12/097,336, filed as application No. PCT/CA2006/002101 on Dec. 21, 2006, now Pat. No. 7,956,162.

(60) Provisional application No. 60/751,965, filed on Dec. 21, 2005.

(51) Int. Cl.
*G01N 33/574* (2006.01)
(52) U.S. Cl. .......................... 436/64; 435/7.23
(58) Field of Classification Search .................. None
See application file for complete search history.

(56) References Cited

U.S. PATENT DOCUMENTS

2008/0213922 A1* 9/2008 Chahal ........................ 436/543

FOREIGN PATENT DOCUMENTS

| WO | WO00/29623 A2 | 5/2000 |
| WO | WO2006/105653 A1 | 10/2006 |

OTHER PUBLICATIONS

Tosatto et al (Current Pharmaceutical Design, 12:2067-2086, 2006).*
Jones (Pharmacogenomics Journal, 1:126-134, 2001).*
Wikstrand et al (Can Res, 55:3140-3148, 1995).*
Database EMBL [Online] "*Homo sapiens* transcriptional repressor scratch mRNA, complete cds", Database Accession No. AY014996, Feb. 28, 2001.
Database EMBL [Online] "*Homo sapiens* SCRT1 gene, Virual Transcript, partial sequence, genomic survey sequence", Database Accession No. DQ035314, Jun. 3, 2005.
Database EMBL [Online] "RZPD *Homo sapiens* cDNA clone IMAGp998I079430=IMAGE:4156878 5' EST", Database Accession No. BX282754, Feb. 26, 2003.
De Craene, B., et al. "Unravelling signalling cascades for the Snail family of transcription factors", Cellular Signalling, 2005, vol. 17, No. 5, p. 535-547.
Nakaura, E.K., et al. "Mammalian Scratch: A neural-specific Snail family transcriptional repressor", Proceedings of the Nat. Academy of Sc. USA, 2001, vol. 98, p. 4010-4015.
Nieto, M.A., "The snail superfamily of zinc-finger transcription factors", Nature Reviews Mol. Cell Biol., 2002, vol. 3, No. 3, p. 155-166.
Roark, M. et al. "Scratch, a pan-neural gene encoding a zinc finger protein related to snail, promotes neural development", Genes & Develop., 1995, vol. 9, No. 19, p. 2384-2398.

* cited by examiner

*Primary Examiner* — Brad Duffy
(74) *Attorney, Agent, or Firm* — Bereskin & Parr LLP/S.E.N.C.R.L., s.r.l.; Micheline Gravelle

(57) ABSTRACT

The present invention provides a novel cancer-associated antigen that can be used in the treatment and diagnosis of cancer. Further, the invention provides amino acid and nucleic acid sequence of the novel antigen, binding proteins, and immunoconjugates. The invention also relates to diagnostic and therapeutic methods and kits.

4 Claims, 18 Drawing Sheets

FIGURE 1
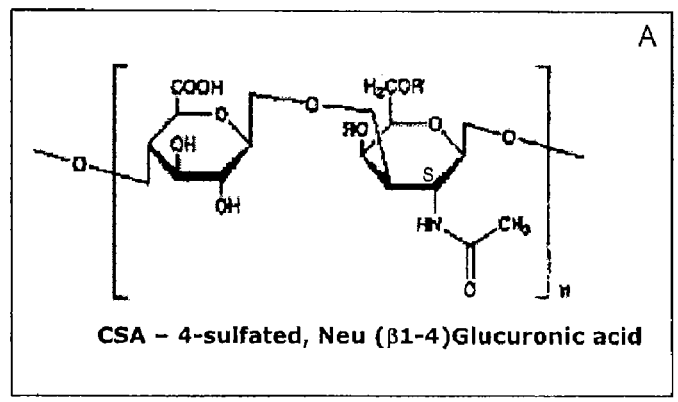
CSA – 4-sulfated, Neu (β1-4)Glucuronic acid
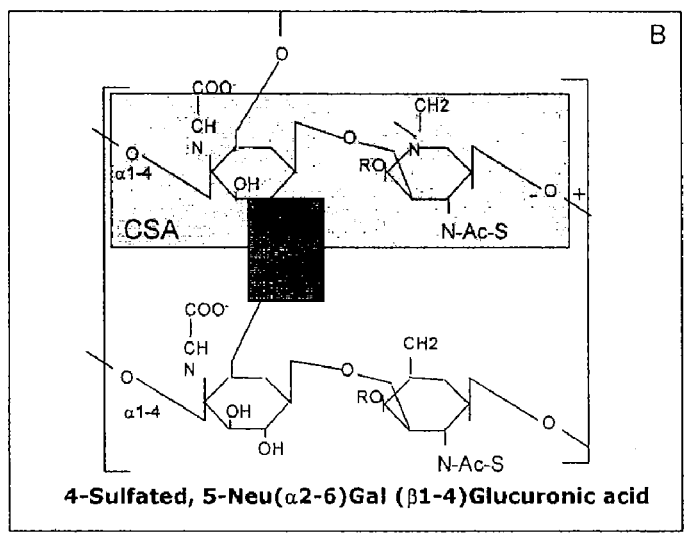
4-Sulfated, 5-Neu(α2-6)Gal (β1-4)Glucuronic acid
FIGURE 2
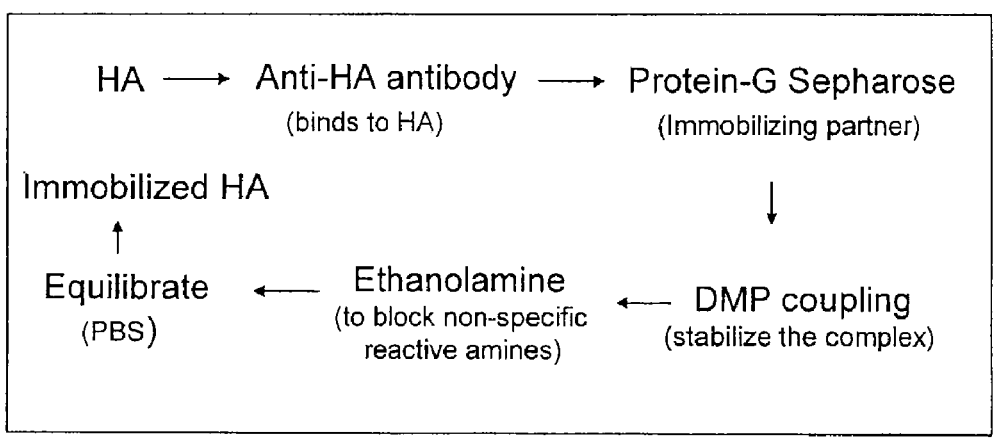

FIGURE 5

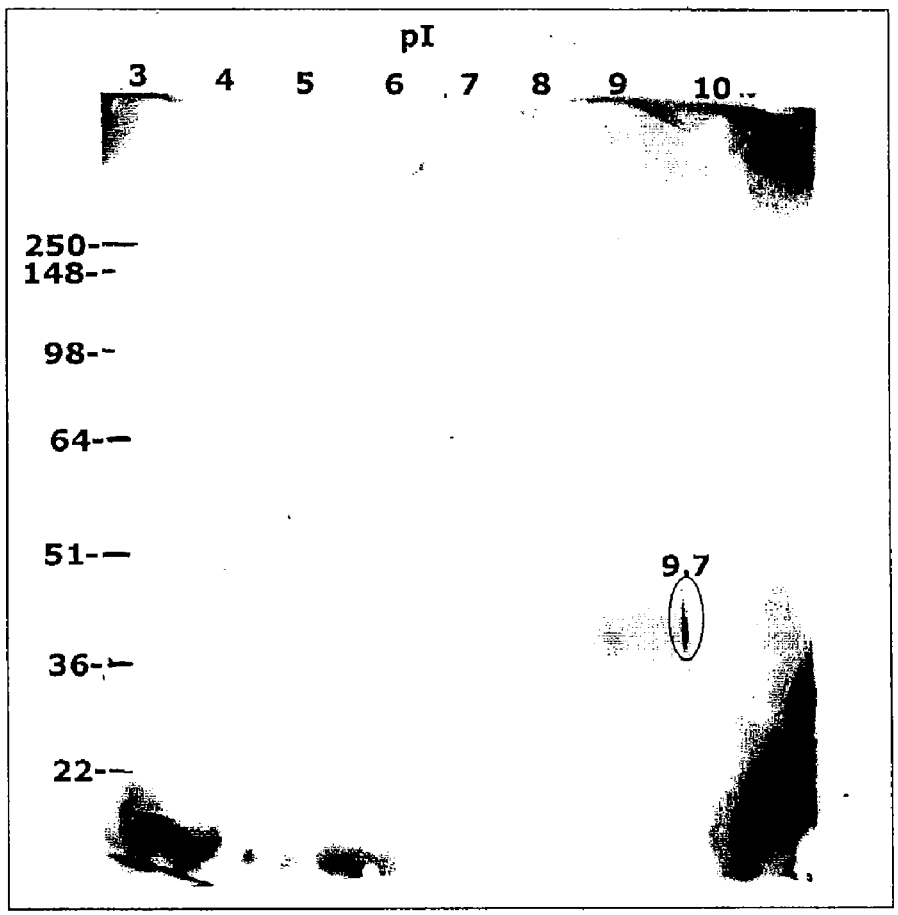

FIGURE 6

```
    MPRSFLVKKV KLDAFSSADL ESAYGRARSD LGAPLHDKGY LSDYVGPSSV
 51 YDGDAEAALL KGPSPEPMYA AAVRGELGPA AAGSAPPPTP RPELATAAGG
101 YINGDAAVSE GYAADAFFIT DGRSRRKASN AGSAAAPSTA SAAAPDGDAG
151 GGGGAGGRSL GSGPGGRGGT RAGAGTEARA GPGAAGAGGR HACGECGKTY
201 ATSSNLSRHK QTHRSLDSQL ARRCPTCGKV YVSMPAMAMH LLTHDLRHKC
251 GVCGKAFSRP WLLQGHMRSH TGEKPFGCAH CGKAFADRSN LRAHMQTHSA
301 FKHFQCKRCK KSFALKSYLN KHYESACFKG GAGGPAAPAP PQLSPVQA
```

FIGURE 7

Sequence coverage obtained for gi|15928387 from MDA-MB-435S

Unknown (protein for IMAGE:4156878) [Homo sapiens] gi|15928387

```
    AGAGGRHACG ECGKTYATSS NLSRHKQTHR SLDSQLARRC PTCGKVYVSM
 51 PAMAMHLLTH DLRHKCGVCG KAFSRPWLLQ GHMRSHTGEK PFGCAHCGKA
101 FADRSNLRAH MQTHSAFKHF QCKRCKKSFA LKSYLNKHYE SACFKGGAGG
151 PAAPAPPQLS PVQA
```

BLAST sequence comparison for 435S-derived sequence and Scrt

```
435S_seq    1 AGAGGRHACGECGKTYATSSNLSRHKQTHRSLDSQLARRCPTCGKVYVSMPAMAMHLLTH
              ************************************************************
Scrt_seq  185    GGRHACGECGKTYATSSNLSRHKQTHRSLDSQLARRCPTCGKVYVSMPAMAMHLLTH 435S_seq   61 DLRHKCGVCGKAFSRPWLLQGHMRSHTGEKPFGCAHCGKAFADRSNLRAHMQTHSAFKHF
              ************************************************************
Scrt_seq  245 DLRHKCGVCGKAFSRPWLLQGHMRSHTGEKPFGCAHCGKAFADRSNLRAHMQTHSAFKHF 435S_seq  121 QCKRCKKSFALKSYLNKHYESACFKGGAGGPAAPAPPQLSPVQA
              ************************************************************
Scrt_seq  305 QCKRCKKSFALKSYLNKHYESACFKGGAGGPAAPAPPQLSPVQA
```

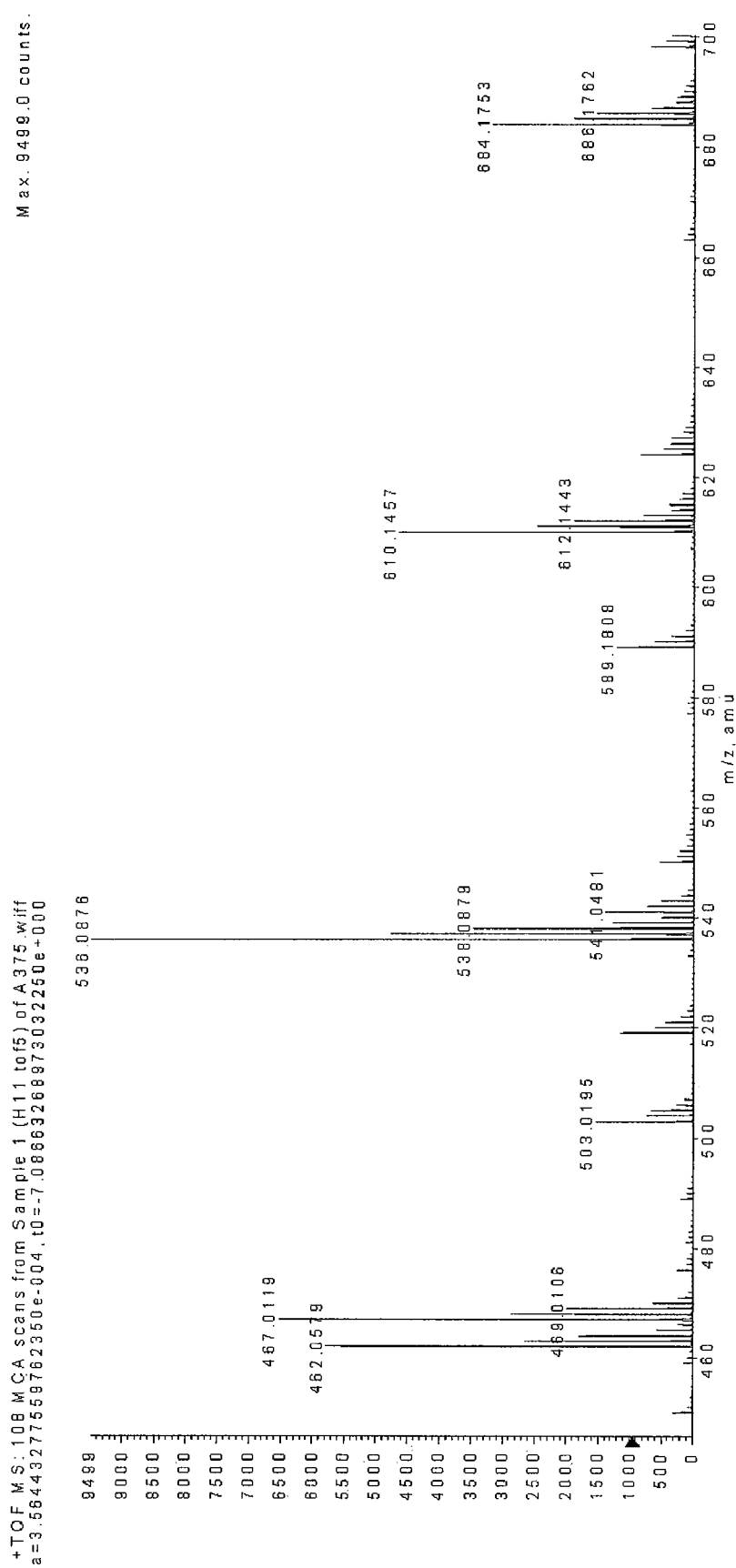
FIGURE 8A – TOF-MS of A-375_H11

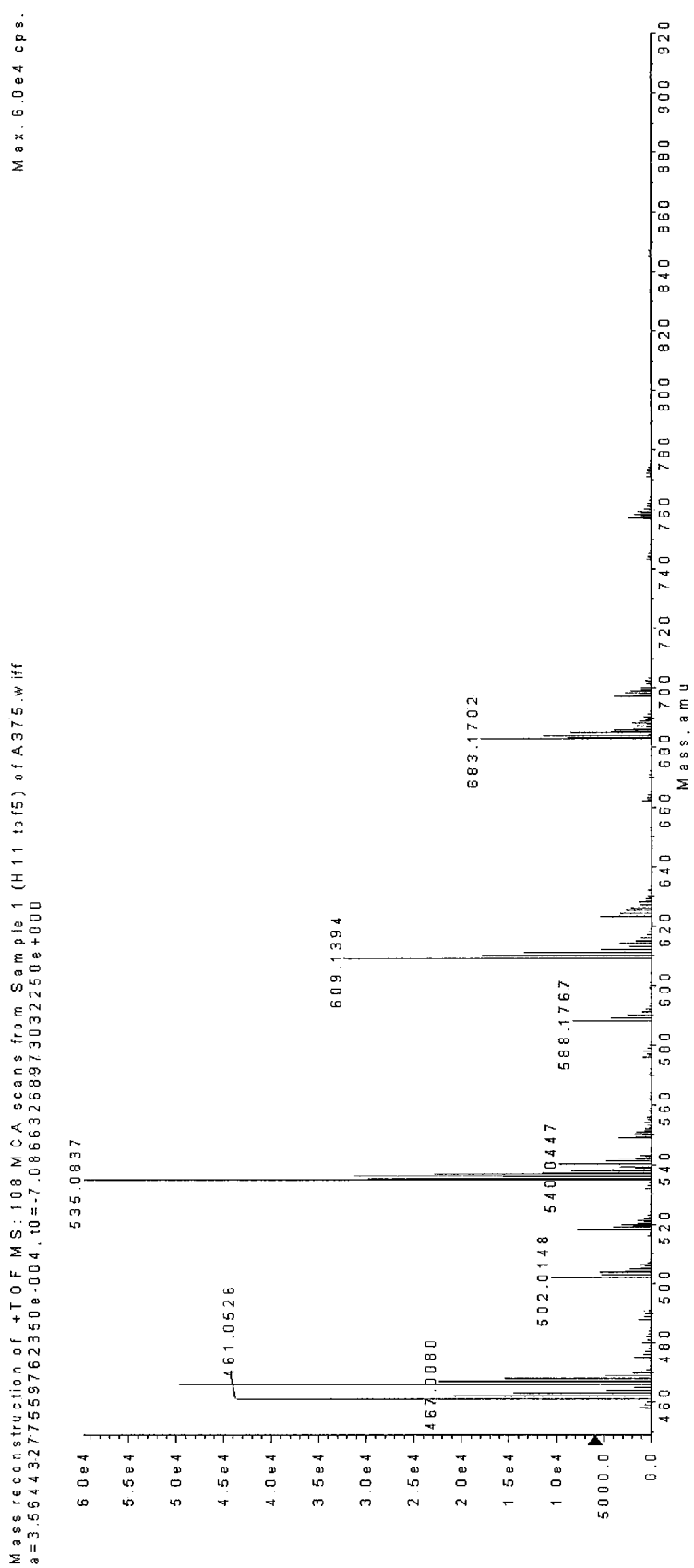
FIGURE 8B – Mass reconstruction of A-375_H11

FIGURE 11

SEQ ID NO: 1

```
    MPRSFLVKKV KLDAFSSADL ESAYGRAREL AAELAAAGEE GFALSPSSV
 51 YDGDAEAALL KGPSPEPMYA AAVRGELGPA AAGSAPPPTP RPELATAAGG
101 YINGDAAVSE GYAADAFFIT DGRSRRKASN AGSAAAPSTA SAAAPDGDAG
151 GGGGAGGRSL GSGPGGRGGT RAGAGTEARA GPGAAGAGGR HACGECGKTY
201 ATSSNLSRHK QTHRSLDSQL ARRCPTCGKV YVSMPAMAMH LLTHDLRHKC
251 GVCGKAFSRP WLLQGHMRSH TGEKPFGCAH CGKAFADRSN LRAHMQTHSA
301 FKHFQCKRCK KSFALKSYLN KHYESACFKG GAGGPAAPAP PQLSPVQA
```

FIGURE 12

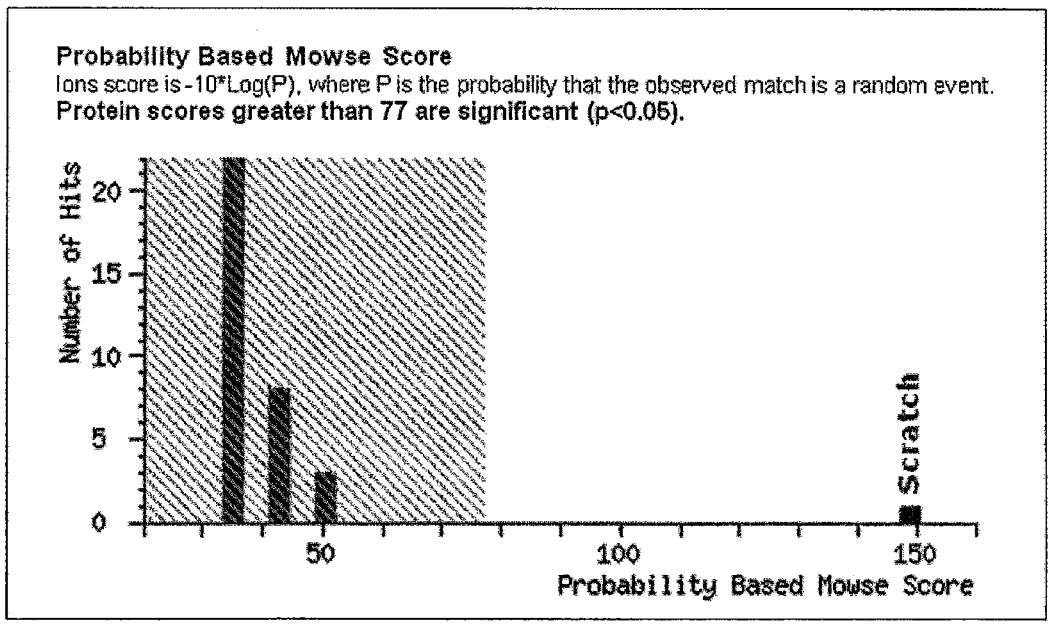

FIGURE 13

| | Accession | Mass | Score | Description |
|---|---|---|---|---|
| 1 | gi\|13775236 | 35570 | 259 | scratch [Homo sapiens] |
| 2 | gi\|18700038 | 36546 | 137 | Scratch homolog1 Zinc finger protein [Mus musculus] |
| 3 | gi\|34867010 | 36573 | 58 | PREDICTED: similar to transcriptional repressor scratch [Rattus norvegicus] |
| 4 | gi\|46430491 | 32583 | 52 | scratch 2 protein [Homo sapiens] |
| 5 | gi\|51460390 | 13830 | 52 | PREDICTED: hypothetical protein XP_499570 [Homo sapiens] |
| 6 | gi\|76633954 | 17808 | 51 | PREDICTED: similar to scratch homolog 1, zinc finger protein, partial [Bos taurus] |
| 7 | gi\|62646193 | 29336 | 48 | PREDICTED: similar to Transcriptional repressor scratch 2 |
| 8 | gi\|68401409 | 26007 | 41 | PREDICTED: similar to scratch homolog 1, zinc finger protein [Danio rerio] |
| 9 | gi\|235397 | 24695 | 30 | HMFG [Homo sapiens] |
| 10 | gi\|2239432 | 3387 | 30 | T-cell receptor delta chain [Homo sapiens] |
| 11 | gi\|184111 | 5867 | 30 | Kruppel-related protein (AA at 172) |
| 12 | gi\|70798131 | 12787 | 30 | immunoglobulin heavy chain variable region [Homo sapiens] |
| 13 | gi\|5668903 | 101098 | 30 | heparan N-deacetylase/N-sulfotransferase 3 [Homo sapiens] |
| 14 | gi\|55957998 | 41108 | 30 | OTTHUMP00000021964 [Homo sapiens] |
| 15 | gi\|40218010 | 14253 | 29 | immunoglobulin heavy chain variable region [Homo sapiens] |
| 16 | gi\|17384998 | 13254 | 29 | immunoglobulin heavy chain variable region [Homo sapiens] |
| 17 | gi\|3212542 | 43068 | 29 | Chain D, Structure Of Human Isovaleryl-Coa Dehydrogenase |
| 18 | gi\|1552280 | 14036 | 28 | immunoglobulin G heavy chain [Homo sapiens] |
| 19 | gi\|1675307 | 9276 | 28 | rearranged Ig heavy chain [Homo sapiens] |
| 20 | gi\|746415 | 52725 | 28 | I kappa BR |

Monoisotopic mass of neutral peptide Mr(calc): 2134.9614 Ions Score: 90 Expect: 0.0016
Matches: 38/220 fragment ions using 36 most intense peaks

FIGURE 17

Restriction map of Scratch-1

```
            Ppu MI
            |
atgcccaggtccttcctggtcaagaaggtcaaacttgacgcgttctcttcggccgacctggagagcgcct
++++|++++|++++|++++|++++|++++|++++|++++|++++|++++|++++|++++|++++|++++|   70
tacgggtccaggaaggaccagttcttccagtttgaactgcgcaagagaagccggctggacctctcgcgga
 M  P  R  S  F  L  V  K  K  V  K  L  D  A  F  S  S  A  D  L  E  S  A Acc 65I
       Eco 57MI                            |  Kpn I
       Bpm I      Bsg I    Asc I           |  | Bbv CI              Psp OMI
       |          |        |                  ||                    |
acggacgcgcccgcagcgacctcggcgcgccactgcacgataaagggtacctcagcgactacgtggggcc
++++|++++|++++|++++|++++|++++|++++|++++|++++|++++|++++|++++|++++|++++|   140
tgcctgcgcgggcgtcgctggagccgcgcggtgacgtgctatttcccatggagtcgctgatgcaccccgg
 Y  G  R  A  R  S  D  L  G  A  P  L  H  D  K  G  Y  L  S  D  Y  V  G  P Bme 1580I  Bcc I
Apa I     | Acc I                                 Bsa XI'
|         || |                                    |
ctcgtccgtctacgatggcgacgccgaggctgcgctgctcaaagggccgtcgccggagcccatgtacgca
++++|++++|++++|++++|++++|++++|++++|++++|++++|++++|++++|++++|++++|++++|   210
gagcaggcagatgctaccgctgcggctccgacgcgacgagtttcccggcagcggcctcgggtacatgcgt
 S  S  V  Y  D  G  D  A  E  A  A  L  L  K  G  P  S  P  E  P  M  Y  A Bsa XI
        |
gcagctgtgcgtggagagctgggtccggcggctgcagggtctgcgccgccgcccaccccgcgcccggagc
++++|++++|++++|++++|++++|++++|++++|++++|++++|++++|++++|++++|++++|++++|   280
cgtcgacacgcacctctcgacccaggccgccgacgtccagacgcggcggcgggtggggcgcgggcctcg
 A  A  V  R  G  E  L  G  P  A  A  A  G  S  A  P  P  P  T  P  R  P  E Drd I                    Tsp DTI  Hph I
                                 |                        |        |
tggccaccgctgcgggcggctacatcaacggcgacgcggccgtcagcgagggctacgcggcggacgcctt
++++|++++|++++|++++|++++|++++|++++|++++|++++|++++|++++|++++|++++|++++|   350
accggtggcgacgcccgccgatgtagttgccgctgcgccggcagtcgctcccgatgcgccgcctgcggaa
 L  A  T  A  A  G  G  Y  I  N  G  D  A  A  V  S  E  G  Y  A  A  D  A  F Ecl I
       |
cttcatcaccgacgggcgctcgcggcgtaaggcttccaatgccggcgctgccgccgctccctccacagcc
++++|++++|++++|++++|++++|++++|++++|++++|++++|++++|++++|++++|++++|++++|   420
gaagtagtggctgcccgcgagcgccgcattccgaaggttacggccgcgacggcggcgagggaggtgtcgg
 F  I  T  D  G  R  S  R  R  K  A  S  N  A  G  A  A  A  A  P  S  T  A Bst YI
                                                      Bam HI
                                                      Sau 3AI
                                                      | Dpn I
                                                      |  | Bst KTI
                                                      |  ||
tcggcggcggcccccgacggcgacgccggaggcggggcggggcgggcggcgcagcttgggatccggc
++++|++++|++++|++++|++++|++++|++++|++++|++++|++++|++++|++++|++++|++++|   490
agccgccgccgggggctgccgctgcggcctccgcccccgccccgcccgccgcgtcgaaccctaggcccg
 S  A  A  A  P  D  G  D  A  G  G  G  G  A  G  G  R  S  L  G  S  G
```

Continuation of FIGURE 17

```
cggggggccggggcggcacgcgcgcgggggcaggcaccgaggcgcgcgcggggccaggggccgcaggtgc
                                                                                    560
gcccccggccccgccgtgcgcgcgccccgtccgtggctccgcgcgcgcccggtccccggcgtccacg
 P  G  G  R  G  G  T  R  A  G  A  G  T  E  A  R  A  G  P  G  A  A  G  A Taq I
                                                              |
tggcggccggcacgcgtgcggcgagtgcggcaaaacatacgccacgtcgtcgaacctgagccgccacaag
                                                                                    630
accgccggccgtgcgcacgccgctcacgccgttttgtatgcggtgcagcagcttggactcggcggtgttc
    G  G  R  H  A  C  G  E  C  G  K  T  Y  A  T  S  S  N  L  S  R  H  K cagacgcaccgcagcctggacagccagctggcgcggcgctgcccgacgtgcggcaaggtgtacgtgtcca
                                                                                    700
gtctgcgtggcgtcggacctgtcggtcgaccgcgccgcgacgggctgcacgccgttccacatgcacaggt
    Q  T  H  R  S  L  D  S  Q  L  A  R  R  C  P  T  C  G  K  V  Y  V  S Sty I
         Nco I    Msl I
           |       |
tgccggccatggccatgcacctgctcacgcacgacctgcgccacaagtgcggcgtgtgcggcaaagcctt
                                                                                    770
acggccggtaccggtacgtggacgagtgcgtgctggacgcggtgttcacgccgcacacgccgtttcggaa
    M  P  A  M  H  L  L  T  H  D  L  R  H  K  C  G  V  C  G  K  A  F Sgr AI
                                         |
ctcgcggccctggctgctgcagggccacatgcgctcgcacaccggcgagaaaccccttcggctgcgcgcac
                                                                                    840
gagcgccgggaccgacgacgtcccggtgtacgcgagcgtgtggccgctctttgggaagccgacgcgcgtg
    S  R  P  W  L  L  Q  G  H  M  R  S  H  T  G  E  K  P  F  G  C  A  H Mme I
                                           | Bsm I
                                           | |
tgcggcaaggccttcgccgaccgctccaacctgcgcgcgcacatgcagacgcattcggccttcaagcact
                                                                                    910
acgccgttccggaagcggctggcgaggttggacgcgcgcgtgtacgtctgcgtaagccggaagttcgtga
    C  G  K  A  F  A  D  R  S  N  L  R  A  H  M  Q  T  H  S  A  F  K  H Sap I                                                         Ple I
   Bsr I    Afe | Bpu EI           Sml I                         Hin fI     | Mly I
     |       |  |  |                 |                              |       | |
tccagtgcaagcgctgcaagaagagcttcgcgctcaagtcctatctcaacaagcactacgagtcggcctg
                                                                                    980
aggtcacgttcgcgacgttcttctcgaagcgcgagttcaggatagagttgttcgtgatgctcagccggac
    F  Q  C  K  R  C  K  K  S  F  A  L  K  S  Y  I  N  K  H  Y  E  S  A  C Kas I
          | Nar I
          |  | Sfo I
          |  |  | Bbe I      Sac II               Blp I              Bfa I
          |  |  |  |           |                    |                  |
cttcaagggcggcgccggaggccccgcggctcctgcgccgccacagctcagccctgtgcaggcctag
                                                                                    1047
gaagttcccgccgcggcctccggggcgccgaggacgcggcggtgtcgagtcgggacacgtccggatc
    F  K  G  G  A  G  G  P  A  A  P  A  P  P  Q  L  S  P  V  Q  A
```

CANCER-ASSOCIATED ANTIGEN

RELATED APPLICATIONS

This application is a continuation of U.S. application Ser. No. 12/097,336 filed Nov. 12, 2008 (now Pat. No. 7,956,162), which is a national phase entry application of PCT/CA2006/002101 filed Dec. 21, 2006 (which designed the U.S.) which claims the benefit of U.S. provisional application Ser. No. 60/751,965 filed Dec. 21, 2005 (now abandoned). All of the prior applications are incorporated herein by reference in their entirety.

Incorporation of Sequence Listing

A computer readable form of the Sequence Listing "10241-232_SequenceListing.txt" (18,407 bytes), submitted via EFS-WEB and created on Apr. 19, 2011, is herein incorporated by reference.

FIELD OF THE INVENTION

The invention relates to a novel antigen associated with cancer and methods and compositions for treating and detecting cancer.

BACKGROUND OF THE INVENTION

In the year 2000, an estimated 22 million people were suffering from cancer worldwide and 6.2 millions deaths were attributed to this class of diseases. Every year, there are over 10 million new cases and this estimate is expected to grow by 50% over the next 15 years (WHO, World Cancer Report. Bernard W. Stewart and Paul Kleihues, eds. IARC Press, Lyon, 2003). Current cancer treatments are limited to invasive surgery, radiation therapy and chemotherapy, all of which cause either potentially severe side-effects, non-specific toxicity and/or traumatizing changes to ones body image and/or quality of life. Cancer can become refractory to chemotherapy reducing further treatment options and likelihood of success. The prognosis for some cancer is worse than for others and some are almost always fatal. In addition, some cancers with a relatively high treatment success rate remain major killers due to their high incidence rates.

One of the causes for the inadequacy of current cancer treatments is their lack of selectivity for affected tissues and cells. Surgical resection always involves the removal of apparently normal tissue as a "safety margin" which can increase morbidity and risk of complications. It also always removes some of the healthy tissue that may be interspersed with tumor cells and that could potentially maintain or restore the function of the affected organ or tissue. Radiation and chemotherapy will kill or damage many normal cells due to their non-specific mode of action. This can result in serious side-effects such as severe nausea, weight loss and reduced stamina, loss of hair etc., as well as increasing the risk of developing secondary cancer later in life. Treatment with greater selectivity for cancer cells would leave normal cells unharmed thus improving outcome, side-effect profile and quality of life.

The selectivity of cancer treatment can be improved by targeting molecules that are specific to cancer cells and not found on normal cells. These molecules can then be used as a target to antibody-based diagnostic or therapeutics or for drugs capable of altering their function.

What little is known about the wild type Scratch protein, has been obtained on the basis of conceptual translation and analysis of the resulting hypothetical protein sequence. Expression of Mammalian Scratch (Scrt) mRNA has been found confined to the brain, spinal cord and newly differentiating, postmitotic neurons suggesting a potential role in neuronal differentiation. The human mammalian Scratch gene has been mapped to q24.3 (chromosome 8) Nakakura et al 2001a, PNAS vol 98 p 4010-4015 and Nakakura et al 2001. Mol. Brain. Res. Vol 95 p 162-166.

Mammalian Scratch shares a SNAG domain with other zinc finger proteins, such as SNAI1, SNAI2, SNAI3, GFII and GFIIB. While quite a few labs working on SNAG domains (Bathe E et al. 2000. Nat. Cell Biol, Vol. 2:84-89; Kataoka H et al., 2000. Nucleic Acids Res. Vol. 28:626-633; Grimes H L et al. 1996. Mol. Cell. Biol. Vol. 16:6263-6272; Hemavathy K et al. 2000. Mol. Cell. Biol. Vol: 20:5087-5095) and snail locomotor functionality have come across the overexpression of the Scrt gene, the presence of the protein itself has not been shown thus far. Based on the hypothetical protein sequence, the Scratch protein should have five zinc finger domains and a SNAG domain responsible for a function in transcription repression. The sequence indicates that the resulting protein would be an intra-nuclear one and in fact expression of recombinant Mammalian Scratch has been found confined to nucleus of transfected cells (Nakakura et al 2001a, PNAS vol 98 p 4010-4015).

SUMMARY OF THE INVENTION

The present inventors have identified a novel cancer-associated protein. Accordingly, the invention provides a novel cancer-associated antigen that can be used in the treatment and diagnosis of cancer. In particular, the antigen is associated with glioblastoma, melanoma, breast cancer, lung cancer, ovarian cancer, lymphoma, colon cancer, gastric cancers and/or prostate cancer.

The novel antigen is a variant of Mammalian Scratch. The variant has a transmembrane domain that is absent in wild type Scratch and as a result the protein of the invention is detectable on the cell surface. Accordingly, the invention includes an isolated protein comprising, a cancer-associated variant of Mammalian Scratch that is expressed on the surface of cancer cells. In an embodiment of the invention, the cancer-associated variant of Mammalian Scratch comprises the amino acid sequence defined by SEQ ID NO:1 or a variant thereof, or the amino acid sequence defined by SEQ ID NO:2 or a variant thereof.

Another aspect of the invention is an isolated protein comprising the amino acid sequence of SEQ ID NO:1 or a variant thereof or the amino acid sequence of SEQ ID NO:2 or a variant thereof.

The invention also includes isolated nucleic acid sequences encoding the isolated protein of the invention, recombinant expression vectors comprising the nucleic acid sequences of the invention and host cells comprising the recombinant expression vectors of the invention.

In another aspect of the invention, the invention includes a method of detecting or monitoring cancer in a subject having or suspected of having cancer, comprising detecting the isolated protein of the invention on a cell in the sample, wherein cancer is indicated, if the isolated protein is detected on the cell.

In addition, the invention includes methods of detecting or monitoring cancer in a subject having or suspected of having cancer, comprising detecting the expression of the cancer-associated variant of Mammalian Scratch in the cell in the sample, wherein cancer is indicated, if the expression of the cancer-associated variant of Mammalian Scratch is detected in the cell.

A further aspect of the invention is a method of treating or preventing cancer in a subject by modulating the function or expression of a Mammalian Scratch in the cancer cell.

The invention also includes pharmaceutical compositions comprising an effective amount of the isolated proteins of the invention, the isolated nucleic acid sequences of the invention and/or the recombinant expression vectors of the invention.

A further aspect of the invention is the use of the isolated proteins of the invention, the isolated nucleic acid sequences of the invention and/or the recombinant expression vectors of the invention to elicit an immune response in a subject.

Another aspect of the invention is the use of the isolated proteins of the invention, the isolated nucleic acid sequences of the invention and/or the recombinant expression vectors of the invention to treat or prevent cancer.

In addition, the invention includes methods for treating or preventing cancer in a subject comprising administering to the subject or a cell from the subject an effective amount of the isolated proteins of the invention, the isolated nucleic acid sequences of the invention and/or the recombinant expression vectors of the invention.

The invention also includes methods for inducing an immune response in a subject against the isolated protein of the invention comprising administering to the subject or a cell from the subject an effective amount of the isolated proteins of the invention, the isolated nucleic acid sequences of the invention and/or the recombinant expression vectors of the invention.

A further aspect of the invention is a method of detecting or monitoring cancer in a subject, comprising the steps of:

(1) contacting a test sample taken from said subject with a binding protein that binds specifically to an antigen on the cancer cell to produce a binding protein-antigen complex;
(2) measuring the amount of binding protein-antigen complex in the test sample; and
(3) comparing the amount of binding protein-antigen complex in the test sample to a control.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 1 shows the glycan structures involved in the binding of VB3-011 to the protein of the invention. Chondroitin sulphate A, also known as Chondroitin-4-sulphate, (due to the presence of the Sulfate molecule at position 4), is a linear molecule of repeating D-galactosamine and glucuronic acid (A). When two such CSA molecules get cross-linked via a 2-6 alpha linkage, the glycan unit now represents the one recognized by Heamagglutinin (HA) (B).

FIG. 2 is a schematic representation of HA reagent immobilization. At the first level, the specificity of HA is enhanced by blocking the anti-HA/protein-G-sepharose epitopes. At the second level, it is immobilized with protein-G-sepharose, simultaneously blocking any non-specificity arising due to the anti-IgG coupling step. Level 3, reaction with ethanolamine, ensures that apart from the HA epitope, all other reactive amine groups are blocked, thus increasing specificity for HA.

FIG. 5 shows the presence of one single protein spot in the purified antigen complex, at Mw~36 kDa and pI=9.7. This represents a Western blot profile of the 2D-PAGE obtained on VB3-011 antigen purification. The corresponding spot from the gel was used for ID purposes.

FIG. 6 and SEQ ID NO:3 show the complete mapping of the peptides obtained and the sequence coverage of the wild type Mammalian Scratch molecule, Accession # gi|13775236. The underlined amino acids represent the sequences of amino acids identified from MS analysis.

FIG. 7 and SEQ ID NO:4 show the sequence coverage obtained for gi|15928387 from MDA-MB-435S and a BLAST sequence comparison for 435S-derived sequence and Scrt. MDA-MD-435S shows the presence of a truncated version of Scratch, i.e., 17.823 kDa protein gi|15928387, with 100% homology to sequences 185-366 of SEQ ID NO:3 of the Wild type Mammalian Scratch molecule.

FIG. 8 shows the TOF-MS scans of peptides obtained from A-375 cell line, to detect the presence of all peptide ions in the sample. One hundred scans at 1200-1400V in the range of 100-1200 amu on a static nanospray resulted in the recovery of a significant number of peptides, which when analyzed yielded a protein ID as Mammalian scratch. FIG. 8A represents the TOF-MS scan with all multiply charged peptide ions and FIG. 8B represents the deconvoluted spectrum with singly charged peptide ions.

FIG. 9 shows TOF-MS scans of peptides obtained from U87MG cell line, to detect the presence of all peptide ions in the sample. Three hundred scans at 1200-1400V in the range of 100-1200 amu on a static nanospray resulted in the recovery of a significant number of peptides, which when analyzed yielded a protein ID as Mammalian Scratch.

FIG. 10 shows TOF-MS scans of peptides obtained from U118MG cell line, to detect the presence of all peptide ions in the sample. Twenty-seven scans at 1200-1400V in the range of 100-1200 amu on a static nanospray resulted in the recovery of a significant number of peptides, which when analyzed yielded a protein ID as Mammalian Scratch.

FIG. 11 and SEQ ID NO:1 show the sequence coverage of peptides recovered from mass spectrometry analysis as listed in Table 2. A total of 18 peptides were recovered from in-gel tryptic digestion and 67% coverage of the protein was obtained. Underlined sequences represent the peptide sequences recovered. The highlighted peptide includes novel sequences. Specifically, the sequences in bold are the novel sequences and the ones in italics represent exact matches with Mammalian Scratch.

FIG. 12 shows the peptide mass fingerprinting results for the peptides recovered from VB3-011Ag. Protein scores greater than 77 were considered significant. The only significant protein IDs observed pointed to the one antigen, known as Mammalian Scratch with a score of 149.

FIG. 13 shows that the identified antigen, Mammalian Scratch, has a significant score of 149. Due to the nature of the database server and the similarity/homology linked proteins, all the isoforms of this protein were pulled down as hits. MS/MS fragmentation and identity of peptides confirms that the antigen is Mammalian Scratch.

FIG. 17 and SEQ ID NOS:5 and 3 show a restriction map of Scratch-1.

Figure 3:
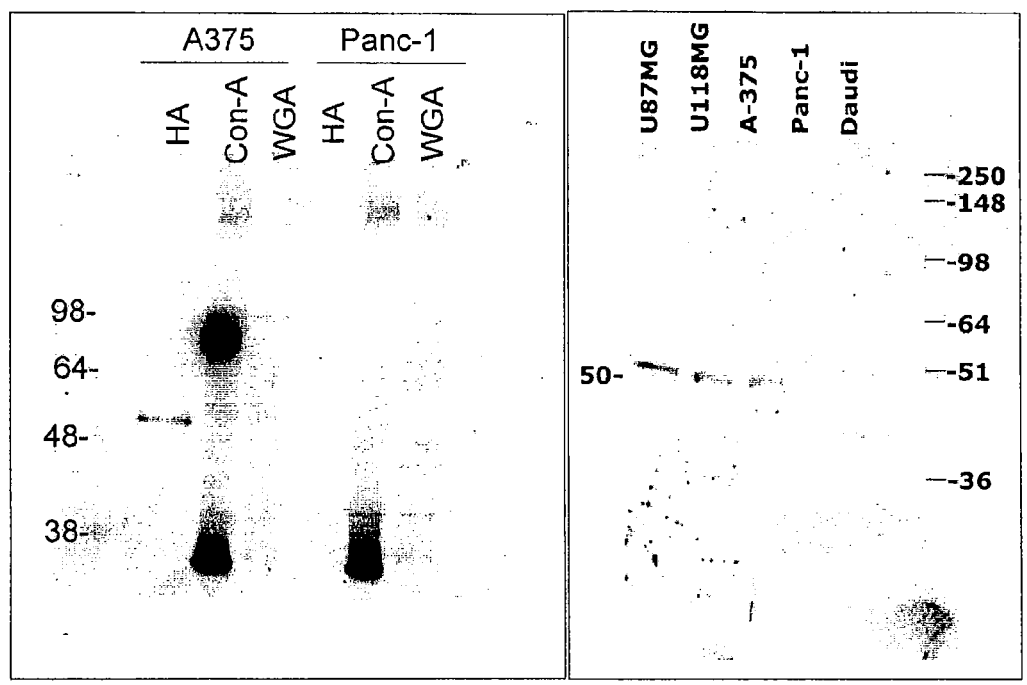
FIG. 3 shows the results of a lectin-based purification of the protein of the invention that is detected by VB3-011. Con-A and WGA lectins pulled down non-specific proteins, whereas HA pulled down only one protein present in the positive and absent in the negative cell line (FIG. 3A). U87MG, U118MG and A375 show a single band when purified with HA, whereas Panc-1 and Daudi show no detectable bands (FIG. 3B).

DETAILED DESCRIPTION OF THE INVENTION (A) Definitions

The term "a cell" includes a single cell as well as a plurality or population of cells. Administering an agent (such as a cancer-associated protein) to a cell includes both in vitro and in vivo administrations.

The term "administered systemically" as used herein means that the immunoconjugate and/or other cancer therapeutic may be administered systemically in a convenient manner such as by injection (subcutaneous, intravenous, intramuscular, etc.), oral administration, inhalation, transdermal administration or topical application (such as topical cream or ointment, etc.), suppository applications, or means of an implant. An implant can be of a porous, non-porous, or gelatinous material, including membranes, such as sialastic membranes, or fibers. Suppositories generally contain active ingredients in the range of 0.5% to 10% by weight.

The term "amino acid" includes all of the naturally occurring amino acids as well as modified amino acids.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', F(ab')$_2$, scFv, dsFv, ds-scFv, dimers, minibodies, diabodies, and multimers thereof and bispecific antibody fragments. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, dsFv, ds-scFv, dimers, minibodies, diabodies, bispecific antibody fragments and other fragments can also be synthesized by recombinant techniques.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log10 [Na+])+0.41(% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm −5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

The term "binding protein" as used herein refers to proteins that specifically bind to another substance such as a cancer-associated antigen of the invention. In an embodiment, binding proteins are antibodies or antibody fragments.

By "biologically compatible form suitable for administration in vivo" is meant a form of the substance to be administered in which any toxic effects are outweighed by the therapeutic effects.

The terms "cancer-associated variant of Mammalian Scratch", "cancer-associated antigen of the invention", "tumor-associated antigen of the invention" or "isolated protein of the invention" as used herein refer to a novel variant of Mammalian Scratch that is expressed on the surface of cancer cells or a variant thereof that is also expressed on the surface of cancer cells. In one embodiment, the novel cancer-associated antigen has at least one transmembrane domain. In specific embodiments, the cancer-associated antigen of Mammalian Scratch is an isolated protein comprising the amino acid sequence defined by SEQ ID NO:1 or an isolated protein comprising the amino acid sequence defined by SEQ ID NO:2.

The term "cancer cell" includes cancer or tumor-forming cells, transformed cells or a cell that is susceptible to becoming a cancer or tumor-forming cell.

A "conservative amino acid substitution", as used herein, is one in which one amino acid residue is replaced with another amino acid residue without abolishing the protein's desired properties.

The term "control" as used herein refers to a sample from a subject or a group of subjects who are either known as having cancer or not having cancer.

The term "controlled release system" as used means the immunoconjugate and/or other cancer therapeutic of the invention can be administered in a controlled fashion. For example, a micropump may deliver controlled doses directly into the area of the tumor, thereby finely regulating the timing and concentration of the pharmaceutical composition (see, e.g., Goodson, 1984, in Medical Applications of Controlled Release, vol. 2, pp. 115-138).

The term "derivative of a peptide" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

The phrase "detecting or monitoring cancer" refers to a method or process of determining if a subject has or does not have cancer, the extent of cancer, the severity of cancer and/or grade of cancer.

The term "direct administration" as used herein means the cancer therapeutic may be administered, without limitation, intratumorally, intravascularly, and peritumorally. For example, the cancer therapeutic may be administered by one or more direct injections into the tumor, by continuous or discontinuous perfusion into the tumor, by introduction of a reservoir of the cancer therapeutic, by introduction of a slow-release apparatus into the tumor, by introduction of a slow-release formulation into the tumor, and/or by direct application onto the tumor. By the mode of administration "into the tumor," introduction of the cancer therapeutic to the area of the tumor, or into a blood vessel or lymphatic vessel that substantially directly flows into the area of the tumor, is included.

As used herein, the phrase "effective amount" means an amount effective, at dosages and for periods of time necessary to achieve the desired result. Effective amounts of therapeutic may vary according to factors such as the disease state, age, sex, weight of the animal. Dosage regime may be adjusted to provide the optimum therapeutic response. For example, several divided doses may be administered daily or the dose may be proportionally reduced as indicated by the exigencies of the therapeutic situation.

The term "eliciting an immune response" or "inducing an immune response" as used herein means initiating, triggering, causing, enhancing, improving or augmenting any response of the immune system, for example, of either a humoral or cell-mediate nature. The initiation or enhancement of an immune response can be assessed using assays known to those skilled in the art including, but not limited to, antibody assays (for example ELISA assays), antigen specific cytotoxicity assays and the production of cytokines (for example ELISPOT assays). Preferably, the isolated proteins, nucleic acid sequences or recombinant expression vectors of the present invention, and the method of the present invention, trigger or enhance a cellular immune response, more preferably a T cell response.

The term "VB3-011 antibody" as used herein refers to an antibody with the variable region of the antibody disclosed in WO 97/044461 which has been shown to specifically bind to a variety of cancer cells and does not significantly bind to normal tissue or cells.

The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded.

The term "isolated proteins" refers to a protein substantially free of cellular material or culture medium when produced by recombinant DNA techniques, or chemical precursors or other chemicals when chemically synthesized. It includes the novel cancer-associated antigen of the invention.

"Mammalian Scratch" (gi|13775236; gi|46397014; gi|13129535) is a protein encoded by a gene that has been mapped to q24.3 of human chromosome 8. From the analysis of the hypothetical protein sequence based on conceptual translation, mammalian scratch has 5 zinc finger domains and a SNAG domain. It is thought to be an intranuclear protein. The hypothetical protein sequence is shown in SEQ ID NO:3.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present invention may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

The term "sample" as used herein refers to any fluid, cell or tissue sample from a subject which can be assayed for cancer.

The term "sequence identity" as used herein refers to the percentage of sequence identity between two polypeptide sequences. In order to determine the percentage of identity between two polypeptide sequences, the amino acid sequences of such two sequences are aligned, preferably using the Clustal W algorithm (Thompson, J D, Higgins D G, Gibson T J, 1994, Nucleic Acids Res. 22 (22): 4673-4680), together with BLOSUM 62 scoring matrix (Henikoff S, and Henikoff J. G., 1992, Proc. Natl. Acad. Sci. USA 89: 10915-10919) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Other methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990: 215: 403).

The term "subject" as used herein refers to any member of the animal kingdom, preferably a mammal, more preferably a human being. In a preferred embodiment, the subject is suspected of having or has cancer.

As used herein, the phrase "treating or preventing cancer" refers to inhibiting of cancer cell replication, preventing transformation of a cell to a cancer-forming cell, inhibiting of cancer spread (metastasis), inhibiting of tumor growth, reducing cancer cell number or tumor growth, decreasing in the malignant grade of a cancer (e.g., increased differentiation), or improving cancer-related symptoms.

The term "variant" as used herein includes modifications or chemical equivalents of the amino acid and nucleotide sequences of the present invention that perform substantially the same function as the proteins or nucleic acid molecules of the invention in substantially the same way. For example, variants of proteins of the invention include, without limitation, conservative amino acid substitutions. Variants of proteins of the invention also include additions and deletions to the proteins of the invention. In addition, variant peptides and variant nucleotide sequences include analogs and derivatives thereof. A variant of the cancer-associated antigen of the invention means a protein sequence that is expressed on cancer cells but not normal cells.

(B) Novel Cancer-Associated Antigen

The invention provides a novel cancer-associated antigen that is expressed on the surface of cancer cells and is not significantly expressed on the surface of normal cells. The novel cancer-associated antigen is a variant of Mammalian Scratch. It has a transmembrane domain that is not present in Mammalian Scratch. A sequence of the transmembrane domain is shown in SEQ ID NO:2. A sequence of the cancer associated variant is shown in SEQ ID NO:1.

In one embodiment, the invention provides an isolated protein comprising the amino acid sequence defined by SEQ ID NO:1 or a variant thereof. In another embodiment, the invention provides an isolated protein comprising the amino acid sequence defined by SEQ ID NO:2. or a variant thereof.

The novel cancer-associated antigen is a variant of Mammalian Scratch that is expressed on the surface of cancer cells. Accordingly, the invention provides an isolated protein comprising a cancer-associated variant of Mammalian Scratch, wherein the cancer-associated variant of Mammalian Scratch is expressed on the surface of cancer cells. In one embodiment, the cancer-associated variant of Mammalian Scratch comprises the amino acid sequence defined by SEQ ID NO:1.

In another embodiment, the cancer-associated variant of Mammalian Scratch comprises the amino acid sequence defined by SEQ ID NO:2.

A person skilled in the art will appreciate that the invention includes variants to the amino acid sequences of SEQ ID NOS:1-2 wherein such variants are also cancer-associated antigens. Variants include chemical equivalents to the sequences disclosed by the present invention. Such equivalents include proteins that perform substantially the same function as the specific proteins disclosed herein in substantially the same way. For example, equivalents include, without limitation, conservative amino acid substitutions.

In one embodiment, the variant amino acid sequences of the isolated proteins of the invention have at least 50%, preferably at least 60%, more preferably at least 70%, most preferably at least 80%, and even more preferably at least 90% sequence identity to SEQ ID NOS:1 or 2.

The invention also provides an isolated nucleic acid sequence encoding the isolated proteins of the invention. In one embodiment, the isolated nucleic acid has the sequence shown in SEQ ID NO:6. In addition, the invention includes variants to the isolated nucleic acid sequences that encode the isolated proteins of the invention. For example, the variants include nucleotide sequences that hybridize to the nucleic acid sequences encoding the isolated proteins of the invention under at least moderately stringent hybridization conditions. The variant nucleic acid sequences will encode a protein that is a cancer-associated antigen.

The invention includes the use of the isolated proteins or cancer-associated antigens and corresponding nucleic acid sequences For example, the use of the isolated proteins of the invention to generate binding proteins and immunoconjugates that can be used to treat or prevent cancer or that can be used to detect or monitor cancer in a subject. Accordingly, the invention includes the use of the isolated proteins and nucleic acid sequences of the invention to treat or prevent cancer and in the manufacture of a medicament to treat or prevent cancer or for the diagnosis of cancer.

(C) Pharmaceutical Compositions, Methods and Uses of the Novel Cancer-Associated Antigen The invention provides a novel cancer-associated antigen that is expressed on the surface of cancer cells and not significantly expressed on the surface of normal cells. Thus, the novel cancer-associated antigen can be used in therapies to treat and prevent cancer, including using the isolated proteins of the invention to elicit an immune response in vivo. In addition, the invention includes diagnostic methods for cancer that comprise detecting the novel cancer-associated antigen.

The cancer can be any cancer that expresses the cancer-associated antigen of the invention on its cell surface. In one embodiment of the invention, cancer includes, without limitation, stomach cancer, colon cancer, prostate cancer as well as cervical cancer, uterine cancer, ovarian cancer, pancreatic cancer, kidney cancer, liver cancer, head and neck cancer, squamous cell carcinoma, gastrointestinal cancer, breast cancer (such as carcinoma, ductal, lobular, and nipple), lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer, neuroblastoma, sarcomas, rectum cancer, bladder cancer, pancreatic cancer, endometrial cancer, plasmacytoma, lymphoma, and melanoma. In a preferred embodiment, the cancer includes, without limitation, glioblastoma, melanoma, breast cancer, lung cancer, ovarian cancer, lymphoma, colon cancer, gastric cancers and/or prostate cancer.

(i) Pharmaceutical Compositions

One aspect of the invention is a pharmaceutical composition comprising an effective amount of the isolated protein of the invention in admixture with a suitable diluent or carrier. Another aspect of the invention is a pharmaceutical a composition comprising an effective amount of the isolated nucleic acid of the invention in admixture with a suitable diluent or carrier. A further aspect of the invention is a pharmaceutical composition comprising an effective amount of the recombinant expression vector of the invention in admixture with a suitable diluent or carrier.

For example, the pharmaceutical compositions of the invention can be used to treat or prevent cancer. In addition, the pharmaceutical compositions can be used to elicit an immune response in a subject against an isolated protein of the invention.

The compositions described herein can be prepared by known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, $20^{th}$ ed., Mack Publishing Company, Easton, Pa., USA, 2000). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Immunogenicity can be significantly improved if the immunizing agents (i.e. the isolated protein of the invention, and/or nucleic acid sequences coding therefore, and/or recombinant expression vectors) and/or composition is, regardless of administration format, co-immunized with an adjuvant. Commonly, adjuvants are used as a 0.05 to 1.0 percent solution in phosphate buffered saline. Adjuvants enhance the immunogenicity of an immunogen but are not necessarily immunogenic in of themselves. Adjuvants may act by retaining the immunogen locally near the site of administration to produce a depot effect facilitating a slow, sustained release of immunogen to cells of the immune system. Adjuvants can also attract cells of the immune system to an immunogen depot and stimulate such cells to elicit immune response. As such, embodiments of this invention encompass pharmaceutical compositions further comprising adjuvants.

Adjuvants have been used for many years to improve the host immune responses to, for example, vaccines. Intrinsic adjuvants (such as lipopolysaccharides) normally are the components of killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established. Notwithstanding, it does have limitations. For example, alum is ineffective for influenza vaccination and inconsistently elicits a cell mediated immune response with other immunogens. The antibodies elicited by alum-adjuvanted antigens are mainly of the IgG1 isotype in the mouse, which may not be optimal for protection by some vaccinal agents.

A wide range of extrinsic adjuvants can provoke potent immune responses to immunogens. These include saponins complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

In one aspect of this invention, adjuvants useful in any of the embodiments of the invention described herein are as follows. Adjuvants for parenteral immunization include aluminum compounds (such as aluminum hydroxide, aluminum phosphate, and aluminum hydroxy phosphate). The antigen can be precipitated with, or adsorbed onto, the aluminum compound according to standard protocols. Other adjuvants such as RIBI (ImmunoChem, Hamilton, Mont.) can also be used in parenteral administration.

Adjuvants for mucosal immunization include bacterial toxins (e.g., the cholera toxin (CT), the *E. coli* heat-labile toxin (LT), the *Clostridium difficile* toxin A and the pertussis toxin (PT), or combinations, subunits, toxoids, or mutants thereof). For example, a purified preparation of native cholera toxin subunit B (CTB) can be of use. Fragments, homologs, derivatives, and fusion to any of these toxins are also suitable, provided that they retain adjuvant activity. Preferably, a mutant having reduced toxicity is used. Suitable mutants have been described (e.g., in WO 95/17211 (Arg-7-Lys CT mutant), WO 96/6627 (Arg-192-Gly LT mutant), and WO 95/34323 (Arg-9-Lys and Glu-129-Gly PT mutant)). Additional LT mutants that can be used in the methods and compositions of the invention include, for example Ser-63-Lys, Ala-69-Gly, Glu-110-Asp, and Glu-112-Asp mutants. Other adjuvants (such as a bacterial monophosphoryl lipid A (MPLA) of various sources (e.g., *E. coli, Salmonella minnesota, Salmonella typhimurium,* or *Shigella flexneri,* saponins, or polylactide glycolide (PLGA) microspheres) can also be used in mucosal administration.

Adjuvants useful for both mucosal and parenteral immunization include polyphosphazene (for example, WO 95/2415), DC-chol (3 b-(N—(N',N'-dimethyl aminomethane)-carbamoyl) cholesterol (for example, U.S. Pat. No. 5,283,185 and WO 96/14831) and QS-21 (for example, WO 88/9336).

A subject may be immunized with a pharmaceutical composition comprising an isolated protein of the invention, an isolated nucleic acid sequence of the invention and/or a recombinant expression vector of the invention by any conventional route as is known to one skilled in the art. This may include, for example, immunization via a mucosal (e.g., ocular, intranasal, oral, gastric, pulmonary, intestinal, rectal, vaginal, or urinary tract) surface, via the parenteral (e.g., subcutaneous, intradermal, intramuscular, intravenous, or intraperitoneal) route or intranodally. Preferred routes depend upon the choice of the immunogen as will be apparent to one skilled in the art. The administration can be achieved in a single dose or repeated at intervals.

The appropriate dosage depends on various parameters understood by skilled artisans such as the immunogen itself (i.e. peptide vs. nucleic acid (and more specifically type thereof)), the route of administration and the condition of the animal to be vaccinated (weight, age and the like).

A person skilled in the art will appreciate that the pharmaceutical compositions can be formulated for administration to subjects in a biologically compatible form suitable for administration in vivo. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of the recombinant protein of the invention to elicit a desired response in the individual. Dosage regime may be adjusted to provide the optimum therapeutic response. For example, several divided doses may be administered daily or the dose may be proportionally reduced as indicated by the exigencies of the therapeutic situation.

The pharmaceutical composition of the invention may be administered systemically. The pharmaceutical preparation may be administered directly to the cancer site. Depending on the route of administration, the pharmaceutical composition may be coated in a material to protect the composition from the action of enzymes, acids and other natural conditions that may inactivate the compound.

In accordance with one aspect of the present invention, the pharmaceutical composition is delivered to the subject by direct administration. The invention contemplates the pharmaceutical composition being administered in at least an amount sufficient to achieve the endpoint, and if necessary, comprises a pharmaceutically acceptable carrier.

In accordance with another aspect, the pharmaceutical composition may be administered in vitro. For example, lymphocytes may be removed from a subject with cancer and stimulated in vitro with the composition and then infused back into the subject.

The invention also provides methods for reducing the risk of post-surgical complications comprising administering an effective amount of the pharmaceutical composition of the invention before, during, or after surgery to treat cancer.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The pharmaceutical compositions of the invention may be supplied, for example but not by way of limitation, as a lyophilized powder which is reconstituted with sterile water or saline prior to administration to the subject.

Pharmaceutical compositions of the invention may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N,N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the subject.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In various embodiments of the invention, the pharmaceutical composition is directly administered systemically or directly to the area of the tumor(s).

The pharmaceutical compositions may be used in methods for treating animals, including mammals, preferably humans, with cancer. The dosage and type of pharmaceutical composition to be administered will depend on a variety of factors which may be readily monitored in human subjects. Such factors include the etiology and severity (grade and stage) of the cancer.

Clinical outcomes of cancer treatments using the pharmaceutical compositions of the invention are readily discernable by one of skill in the relevant art, such as a physician. For example, standard medical tests to measure clinical markers of cancer may be strong indicators of the treatment's efficacy. Such tests may include, without limitation, physical examination, performance scales, disease markers, 12-lead ECG, tumor measurements, tissue biopsy, cytoscopy, cytology, longest diameter of tumor calculations, radiography, digital imaging of the tumor, vital signs, weight, recordation of adverse events, assessment of infectious episodes, assessment of concomitant medications, pain assessment, blood or serum chemistry, urinalysis, CT scan, and pharmacokinetic analysis. Furthermore, synergistic effects of a combination therapy comprising the pharmaceutical compositions of the invention and another cancer therapeutic may be determined by comparative studies with patients undergoing monotherapy.

Another embodiment of the invention is a kit for treating or preventing cancer comprising an effective amount of the pharmaceutical composition of the invention, and directions for the use thereof to treat the cancer.

In the majority of approved anticancer therapies, the anticancer therapy is used in combination with other anticancer therapies. Accordingly, the invention provides a method of preventing or treating cancer using the pharmaceutical compositions of the invention in combination with at least one additional anticancer therapy. The other cancer therapy may be administered prior to, overlapping with, concurrently, and/or after administration of the pharmaceutical composition of the invention. When administered concurrently, the pharmaceutical composition of the invention and the other cancer therapeutic may be administered in a single formulation or in separate formulations, and if separately, then optionally, by different modes of administration. The combination of one or more pharmaceutical compositions of the invention and one or more other cancer therapies may synergistically act to combat the tumor or cancer. The other cancer therapies include, without limitation, radiation and other anticancer therapeutic agents. These other cancer therapeutics may include, without limitation, 2,2',2"trichlorotriethylamine, 6-azauridine, 6-diazo-5-oxo-L-norleucine, 6-mercaptopurine, aceglarone, aclacinomycins actinomycin, altretamine, aminoglutethimide, amsacrine, anastrozole, ancitabine, angiogenin antisense oligonucleotide, anthramycin, azacitidine, azaserine, aziridine, batimastar, bcl-2 antisense oligonucleotide, benzodepa, bicalutamide, bisantrene, bleomycin, buserelin, busulfan, cactinomycin, calusterone, carboplatin, carboquone, caminomycin, carmofur, carmustine, carubicin, carzinophilin, chlorambucil, chlornaphazine, chiormadinone acetate, chlorozotocin, chromomycins, cisplatin, cladribine, cyclophosphamide, cytarabine, dacarbazine, dactinomycin, daunorubicin, defosfamide, demecolcine, denopterin, detorubicin, diaziquone, docetaxel, doxifluridine, doxorubicin, droloxifene, dromostanolone, edatrexate, eflomithine, elliptinium acetate, emitefur, enocitabune, epirubicin, epitiostanol, esorubicin, estramustine, etoglucid, etoposide, fadrozole, fenretinide, floxuridine, fludarabine, fluorouracil, flutamide, folinic acid, formestane, fosfestrol, fotemustine, gallium nitrate, gemcitabine, goserelin, hexestrol, hydroxyurea, idarubicin, ifosfamide, improsulfan, interferon-alpha, interferon-beta, interferon-gamma, interleukin-2, L-asparaginase, lentinan, letrozole, leuprolide, lomustine, lonidamine, mannomustine, marcellomycin, mechlorethamine, mechlorethamine oxide hydrochloride, medroxyprogesterone, megestrol acetate, melengestrol, melphalan, menogaril, mepitiostane, methotrexate, meturedepa, mibopl-atin, miltefosine, mitobronitol, mitoguazone, mitolactol, mitomycins, mitotane, mitoxantrone, mopidamol, mycophenolic acid, nilutamide, nimustine, nitracine, nogalamycin, novembichin, olivomycins, oxaliplatin, paclitaxel, pentostatin, peplomycin, perfosfamide, phenamet, phenesterine, pipobroman, piposulfan, pirarubicin, piritrexim, plicamycin, podophyllinic acid 2-ethyl-hydrazide, polyestradiol phosphate, porfimer sodium, porfiromycin, prednimustine, procabazine, propagermanium, PSK, pteropterin, puromycin, quelamycin, ranimustine, razoxane, rodorubicin, roquinimex, sizofican, sobuzoxane, spirogermanium, streptonigrin, streptozocin, tamoxifen, taxotere, tegafur, temozolomide, teniposide, tenuzonic acid, testolacone, thiamiprine, thioguanine, thiotepa, Tomudex, topotecan, toremifene, triaziquone, triethylenemelamine, triethylenephosphoramide, triethylenethiophosphoramide, trilostane, trimetrexate, triptorelin, trofosfamide, trontecan, tubercidin, ubenimex, uracil mustard, uredepa, urethan, vinblastine, vincristine, zinostatin, and zorubicin, cytosine arabinoside, gemtuzumab, thioepa, cyclothosphamide, antimetabolites (e.g., methotrexate, 6-mercaptopurine, 6-thioguanine, cytarabine, 5-fluorouracil, fludarabine, gemcitabine, dacarbazine, temozoamide), hexamethylmelamine, LYSODREN, nucleoside analogues, plant alkaloids (e.g., Taxol, paclitaxel, camptothecin, topotecan, irinotecan (CAMPTOSAR,CPT-11), vincristine, vinca alkyloids such as vinblastine.) podophyllotoxin, epipodophyllotoxin, VP-16 (etoposide), cytochalasin B, gramicidin D, ethidium bromide, emetine, anthracyclines (e.g., daunorubicin), doxorubicin liposomal, dihydroxyanthracindione, mithramycin, actinomycin D, aldesleukin, allutamine, biaomycin, capecitabine, carboplain, chlorabusin, cyclarabine, daclinomycin, floxuridhe, lauprolide acetate, levamisole, lomusline, mercaptopurino, mesna, mitolanc, pegaspergase, pentoslatin, picamycin, riuxlmab, campath-1, straplozocin, tretinoin, VEGF antisense oligonucleotide, vindesine, and vinorelbine. Compositions comprising one or more cancer therapeutics (e.g., FLAG, CHOP) are also contemplated by the present invention. FLAG comprises fludarabine, cytosine arabinoside (Ara-C) and G-CSF. CHOP comprises cyclophosphamide, vincristine, doxorubicin, and prednisone. For a full listing of cancer therapeutics known in the art, see, e.g., the latest editions of The Merck Index and the Physician's Desk Reference.

Pharmaceutical compositions for combination therapy may also include, without limitation, antibiotics (e.g., dactinomycin, bleomycin, mithramycin, anthramycin), asparaginase, *Bacillus* and *Guerin*, diphtheria toxin, procaine, tetracaine, lidocaine, propranolol, anti-mitotic agents, abrin, ricinA, *Pseudomonas* exotoxin, nerve growth factor, platelet derived growth factor, tissue plasminogen activator, antihistaminic agents, anti-nausea agents, etc.

Indeed, administration of an effective amount of a pharmaceutical composition of the invention to a patient in need of such treatment may result in reduced doses of another cancer therapeutic having clinically significant efficacy. Such efficacy of the reduced dose of the other cancer therapeutic may not be observed absent administration with the pharmaceutical compositions of the invention. Accordingly, the present invention provides methods for treating a tumor or cancer comprising administering a reduced dose of one or more other cancer therapeutics.

Moreover, combination therapy comprising the pharmaceutical composition of the invention to a patient in need of such treatment may permit relatively short treatment times when compared to the duration or number of cycles of standard treatment regimens. Accordingly, the present invention provides methods for treating a tumor or cancer comprising administering one or more other cancer therapeutics for relatively short duration and/or in fewer treatment cycles.

Thus, in accordance with the present invention, combination therapies comprising a pharmaceutical composition of the invention and another cancer therapeutic may reduce toxicity (i.e., side effects) of the overall cancer treatment. For example, reduced toxicity, when compared to a monotherapy or another combination therapy, may be observed when delivering a reduced dose of a pharmaceutical composition of the invention and/or other cancer therapeutic, and/or when reducing the duration of a cycle (i.e., the period of a single administration or the period of a series of such administrations), and/or when reducing the number of cycles.

Accordingly, the invention provides a pharmaceutical composition of the invention further comprising one or more additional anticancer therapeutic, optionally in a pharmaceutically acceptable carrier.

The present invention also provides a kit comprising an effective amount of a pharmaceutical composition of the invention, optionally, in combination with one or more other cancer therapeutic, together with instructions for the use thereof to treat cancer.

As stated above, combination therapy with a pharmaceutical composition of the invention may sensitize the cancer or tumor to administration of an additional cancer therapeutic. Accordingly, the present invention contemplates combination therapies for preventing, treating, and/or preventing recurrence of cancer comprising administering an effective amount of a pharmaceutical composition of the invention prior to, subsequently, or concurrently with a reduced dose of a cancer therapeutic. For example, initial treatment with a pharmaceutical composition of the invention may increase the sensitivity of a cancer or tumor to subsequent challenge with a dose of cancer therapeutic. This dose is near, or below, the low range of standard dosages when the cancer therapeutic is administered alone, or in the absence of a pharmaceutical composition of the invention. When concurrently administered, the pharmaceutical composition of the invention may be administered separately from the cancer therapeutic, and optionally, via a different mode of administration.

In an alternate embodiment, administration of the additional cancer therapeutic may sensitize the cancer or tumor to pharmaceutical composition of the invention. In such an embodiment, the additional cancer therapeutic may be given prior to administration of a pharmaceutical composition of the invention.

In one embodiment, the additional cancer therapeutic comprises cisplatin, e.g., PLATINOL or PLATINOL-AQ (Bristol Myers), at a dose ranging from approximately 5 to 10, 11 to 20, 21 to 40, or 41 to 75 mg/m$^2$/cycle.

In another embodiment, the additional cancer therapeutic comprises carboplatin, e.g., PARAPLATIN (Bristol Myers), at a dose ranging from approximately 2 to 3, 4 to 8, 9 to 16, 17 to 35, or 36 to 75 mg/m$^2$/cycle.

In another embodiment, the additional cancer therapeutic comprises cyclophosphamide, e.g., CYTOXAN (Bristol Myers Squibb), at a dose ranging from approximately 0.25 to 0.5, 0.6 to 0.9, 1 to 2, 3 to 5, 6 to 10, 11 to 20, or 21 to 40 mg/kg/cycle.

In another embodiment, the additional cancer therapeutic comprises cytarabine, e.g., CYTOSAR-U (Pharmacia & Upjohn), at a dose ranging from approximately 0.5 to 1, 2 to 4, 5 to 10, 11 to 25, 26 to 50, or 51 to 100 mg/m$^2$/cycle. In another embodiment, the additional cancer therapeutic comprises cytarabine liposome, e.g., DEPOCYT (Chiron Corp.), at a dose ranging from approximately 5 to 50 mg/m$^2$/cycle.

In another embodiment, the additional cancer therapeutic comprises dacarbazine, e.g., DTIC or DTICDOME (Bayer Corp.), at a dose ranging from approximately 15 to 250 mg/m$^2$/cycle or ranging from approximately 0.2 to 2 mg/kg/cycle.

In another embodiment, the additional cancer therapeutic comprises topotecan, e.g., HYCAMTIN (SmithKline Beecham), at a dose ranging from approximately 0.1 to 0.2, 0.3 to 0.4, 0.5 to 0.8, or 0.9 to 1.5 mg/m$^2$/Cycle. In another embodiment, the additional cancer therapeutic comprises irinotecan, e.g., CAMPTOSAR (Pharmacia & Upjohn), at a dose ranging from approximately 5 to 9, 10 to 25, or 26 to 50 mg/m$^2$/cycle.

In another embodiment, the additional cancer therapeutic comprises fludarabine, e.g., FLUDARA (Berlex Laboratories), at a dose ranging from approximately 2.5 to 5, 6 to 10, 11 to 15, or 16 to 25 mg/m$^2$/cycle.

In another embodiment, the additional cancer therapeutic comprises cytosine arabinoside (Ara-C) at a dose ranging from approximately 200 to 2000 mg/m$^2$/cycle, 300 to 1000 mg/m$^2$/cycle, 400 to 800 mg/m$^2$/cycle, or 500 to 700 mg/m$^2$/cycle.

In another embodiment, the additional cancer therapeutic comprises docetaxel, e.g., TAXOTERE (Rhone Poulenc Rorer) at a dose ranging from approximately 6 to 10, 11 to 30, or 31 to 60 mg/m$^2$/cycle.

In another embodiment, the additional cancer therapeutic comprises paclitaxel, e.g., TAXOL (Bristol Myers Squibb), at a dose ranging from approximately 10 to 20, 21 to 40, 41 to 70, or 71 to 135 mg/kg/cycle.

In another embodiment, the additional cancer therapeutic comprises 5-fluorouracil at a dose ranging from approximately 0.5 to 5 mg/kg/cycle, 1 to 4 mg/kg/cycle, or 2-3 mg/kg/cycle.

In another embodiment, the additional cancer therapeutic comprises doxorubicin, e.g., ADRIAMYCIN (Pharmacia & Upjohn), DOXIL (Alza), RUBEX (Bristol Myers Squibb), at a dose ranging from approximately 2 to 4, 5 to 8, 9 to 15, 16 to 30, or 31 to 60 mg/kg/cycle.

In another embodiment, the additional cancer therapeutic comprises etoposide, e.g., VEPESID (Pharmacia & Upjohn), at a dose ranging from approximately 3.5 to 7, 8 to 15, 16 to 25, or 26 to 50 mg/m$^2$/cycle.

In another embodiment, the additional cancer therapeutic comprises vinblastine, e.g., VELBAN (Eli Lilly), at a dose ranging from approximately 0.3 to 0.5, 0.6 to 0.9, 1 to 2, or 3 to 3.6 mg/m$^2$/cycle.

In another embodiment, the additional cancer therapeutic comprises vincristine, e.g., ONCOVIN (Eli Lilly), at a dose ranging from approximately 0.1, 0.2, 0.3, 0.4, 0.5, 0.6 or 0.7 mg/m$^2$/cycle.

In another embodiment, the additional cancer therapeutic comprises methotrexate at a dose ranging from approximately 0.2 to 0.9, 1 to 5, 6 to 10, or 11 to 20 mg/m$^2$/cycle.

In another embodiment, a pharmaceutical composition of the invention is administered in combination with at least one other immunotherapeutic which includes, without limitation, rituxan, rituximab, campath-1, gemtuzumab, and trastuzutmab.

In another embodiment, a pharmaceutical composition of the invention is administered in combination with one or more anti-angiogenic agents which include, without limitation, angiostatin, thalidomide, kringle 5, endostatin, Serpin (Serine Protease Inhibitor), anti-thrombin, 29 kDa N-terminal and a 40 kDa C-terminal proteolytic fragments of fibronectin, 16 kDa proteolytic fragment of prolactin, 7.8 kDa proteolytic fragment of platelet factor-4, a 13 amino acid peptide corresponding to a fragment of platelet factor-4 (Maione et al., 1991, Cancer Res. 51:2077-2083), a 14-amino acid peptide corresponding to a fragment of collagen I (Tolsma et al., 1993, J. Cell Biol. 122:497-51 1), a 19 amino acid peptide corresponding to a fragment of Thrombospondin I (Tolsma et al., 1993, J. Cell Biol. 122:497-511), a 20-amino acid peptide corresponding to a fragment of SPARC (Sage et al., 1995, J. Cell. Biochem. 57:1329-1334), and a variant thereof, including a pharmaceutically acceptable salt thereof.

In another embodiment, a pharmaceutical composition of the invention is administered in combination with a regimen of radiation therapy. The therapy may also comprise surgery and/or chemotherapy. For example, a pharmaceutical composition of the invention may be administered in combination with radiation therapy and cisplatin (Platinol), fluorouracil (5-FU, Adrucil), carboplatin (Paraplatin), and/or paclitaxel (Taxol). Treatment with a pharmaceutical composition of the invention may allow use of lower doses of radiation and/or less frequent radiation treatments, which may for example, reduce the incidence of severe sore throat that impedes swallowing function potentially resulting in undesired weight loss or dehydration.

In another embodiment, a pharmaceutical composition is administered in combination with one or more cytokines which include, without limitation, a lymphokine, tumor necrosis factors, tumor necrosis factor-like cytokine, lymphotoxin, interferon, macrophage inflammatory protein, granulocyte monocyte colony stimulating factor, interleukin (including, without limitation, interleukin-1, interleukin-2, interleukin-6, interleukin-12, interleukin-15, interleukin-18), and a variant thereof, including a pharmaceutically acceptable salt thereof.

In yet another embodiment, a pharmaceutical composition of the invention is administered in combination with a cancer vaccine or biological agents including, without limitation, autologous cells or tissues, non-autologous cells or tissues, carcinoembryonic antigen, alpha-fetoprotein, human chorionic gonadotropin, BCG live vaccine, Mycobacterial cell wall-DNA complexes, melanocyte lineage proteins, and mutated, tumor-specific antigens.

In yet another embodiment, a pharmaceutical composition is administered in association with hormonal therapy. Hormonal therapeutics include, without limitation, a hormonal agonist, hormonal antagonist (e.g., flutamide, tamoxifen, leuprolide acetate (LUPRON)), and steroid (e.g., dexamethasone, retinoid, betamethasone, cortisol, cortisone, prednisone, dehydrotestosterone, glucocorticoid, mineralocorticoid, estrogen, testosterone, progestin).

In yet another embodiment, a pharmaceutical composition is administered in association with a gene therapy program to treat or prevent cancer.

Combination therapy may thus increase the sensitivity of the cancer or tumor to the administered pharmaceutical composition of the invention and/or additional cancer therapeutic. In this manner, shorter treatment cycles may be possible thereby reducing toxic events. The cycle duration may vary according to the specific cancer therapeutic in use. The invention also contemplates continuous or discontinuous administration, or daily doses divided into several partial administrations. An appropriate cycle duration for a specific cancer therapeutic will be appreciated by the skilled artisan, and the invention contemplates the continued assessment of optimal treatment schedules for each cancer therapeutic. Specific guidelines for the skilled artisan are known in the art. See, e.g., Therasse et al., 2000, "New guidelines to evaluate the response to treatment in solid tumors. European Organization for Research and Treatment of Cancer, National Cancer Institute of the United States, National Cancer Institute of Canada," J Natl Cancer Inst. February 2; 92(3):205-16.

It is contemplated that a pharmaceutical composition of the invention may be administered by any suitable method such as injection, oral administration, inhalation, transdermal or intratumorally, whereas any other cancer therapeutic may be delivered to the patient by the same or another mode of administration. Additionally, where multiple cancer therapeutics are intended to be delivered to a subject, a pharmaceutical composition of the invention and one or more of the other cancer therapeutics may be delivered by one method, whereas other cancer therapeutics may be delivered by another mode of administration.

The invention also provides kits comprising an effective amount of a pharmaceutical composition of the invention, optionally, in combination with one or more other cancer therapeutic agent, together with instructions for the use thereof.

(ii) Diagnostic Methods

The novel cancer-associated antigen is expressed on cancer cells and is not significantly expressed on normal cells, thus the detection of the novel cancer-associated antigen can be used as a diagnostic method for cancer.

One embodiment of the invention is a method of detecting or monitoring cancer in a subject having or suspected of having cancer, comprising detecting a cancer-associated variant of Mammalian Scratch on a cell in the sample, wherein cancer is indicated, if the cancer-associated variant of Mammalian Scratch is detected on the cell.

In an embodiment of the invention, a method is provided for detecting cancer cells in a subject comprising:
(a) providing a sample from the subject;
(b) detecting the level of the cancer-associated antigen in the sample; and
(c) comparing the level of the cancer-associated antigen in the sample to a control sample, wherein increased levels of the cancer-associated antigen as compared to the control indicates that the subject has cancer.

The phrase "detecting the level of the cancer-associated antigen" includes the detection of the levels of the cancer-associated antigen as well as detection of the levels of nucleic acid molecules encoding the cancer-associated antigen. Examples of methods for detecting proteins and nucleic acids are discussed in greater detail below.

The cancer-associated antigen preferably comprises the sequence shown in SEQ ID NO:2, more preferably, SEQ ID NO:1.

The term sample can be any sample containing cancer cells that one wishes to detect including, but not limited to, biological fluids (including blood, serum, ascites), tissue extracts, freshly harvested cells, and lysates of cells which have been incubated in cell cultures.

The term "control sample" includes any sample that can be used to establish a base or normal level, and may include tissue samples taken from healthy persons or samples mimicking physiological fluid. The control sample can also be a sample from the subject from another point in time, e.g. prior to cancer therapy.

The method of the invention may be used in the diagnosis and staging of the cancer. The invention may also be used to monitor the progression of a cancer and to monitor whether a particular treatment is effective or not. In particular, the method can be used to confirm the absence or removal of all tumor tissue following surgery, cancer chemotherapy, and/or radiation therapy. The methods can further be used to monitor cancer chemotherapy and tumor reappearance.

In an embodiment, the invention contemplates a method for monitoring the progression of cancer in a subject, comprising:
(a) providing a sample from a subject;
(b) determining the level of the cancer-associated antigen expression in the sample;
(c) repeating steps (a) and (b) at a later point in time and comparing the result of step (b) with the result of step (c) wherein a difference in the level of the cancer-associated antigen expression is indicative of the progression of the cancer in the subject.

In particular, increased levels of the cancer-associated antigen at the later time point may indicate that the cancer is progressing and that the treatment (if applicable) is not being effective. In contrast, decreased levels of the cancer-associated antigen at the later time point may indicate that the cancer is regressing and that the treatment (if applicable) is effective.

A number of techniques can be used to detect the cancer-associated variant of Mammalian Scratch on a cell. For example, binding proteins such as antibodies that bind to the cancer-associated variant of Mammalian Scratch can be used in immunoassays to detect cell surface expression of the cancer-associated variant of Mammalian Scratch. A person skilled in the art will appreciate that a number of techniques can be used to detect and/or quantify cell surface expression of the cancer-associated variant of Mammalian Scratch, including, without limitation, Western blots, immunoprecipitation followed by SDS-PAGE, immunocytochemistry, FACS, protein arrays, and the like.

Methods for Detecting Nucleic Acid Molecules

In one embodiment, the methods of the invention involve the detection of nucleic acid molecules encoding the cancer-associated antigen. Those skilled in the art can construct nucleotide probes for use in the detection of nucleic acid sequences encoding the cancer-associated antigen in samples. Suitable probes can be prepared based on the nucleic acid sequence shown in SEQ ID NO:6 or SEQ ID NO:25. Suitable probes include nucleic acid molecules based on nucleic acid sequences encoding at least 5 sequential amino acids from regions of the cancer-associated antigen, preferably they comprise 15 to 30 nucleotides. A nucleotide probe may be labeled with a detectable substance such as a radioactive label which provides for an adequate signal and has sufficient half-life such as $^{32}P$, $^{3}H$, $^{14}C$ or the like. Other detectable substances which may be used include antigens that are recognized by a specific labeled antibody, fluorescent compounds, enzymes, antibodies specific for a labeled antigen, and luminescent compounds. An appropriate label may be selected having regard to the rate of hybridization and binding of the probe to the nucleotide to be detected and the amount of nucleotide available for hybridization. Labeled probes may be hybridized to nucleic acids on solid supports such as nitrocellulose filters or nylon membranes as generally described in Sambrook et al, 1989, Molecular Cloning, A Laboratory Manual (2nd ed.). The nucleic acid probes may be used to detect genes, preferably in human cells, that encode the cancer-associated antigen. The nucleotide probes may also be useful in the diagnosis of disorders involving the cancer-associated antigen, in monitoring the progression of such disorders, or in monitoring a therapeutic treatment. In an embodiment, the probes are used in the diagnosis of, and in monitoring the progression of cancer, preferably gynecological cancer.

The probe may be used in hybridization techniques to detect genes that encode the cancer-associated antigen. The technique generally involves contacting and incubating nucleic acids (e.g. recombinant DNA molecules, cloned genes) obtained from a sample from a subject or other cellular source with a probe under conditions favorable for the specific annealing of the probes to complementary sequences in the nucleic acids. After incubation, the non-annealed nucleic acids are removed, and the presence of nucleic acids that have hybridized to the probe if any are detected.

The detection of nucleic acid molecules may involve the amplification of specific gene sequences using an amplification method such as polymerase chain reaction (PCR), followed by the analysis of the amplified molecules using techniques known to those skilled in the art. Suitable primers can be routinely designed by one of skill in the art.

Hybridization and amplification techniques described herein may be used, to assay qualitative and quantitative aspects of expression of genes encoding the cancer-associated antigen. For example, RNA may be isolated from a cell type or tissue known to express a gene encoding the cancer-associated antigen, and tested utilizing the hybridization (e.g. standard Northern analyses) or PCR techniques which are known in the art.

The primers and probes may be used in the above described methods in situ i.e. directly on tissue sections (fixed and/or frozen) of subject tissue obtained from biopsies or resections.

Accordingly, the present invention provides a method of detecting cancer cells in a subject comprising:
 (a) providing a sample from the subject;
 (b) extracting nucleic acid molecules encoding the cancer-associated antigen or portion thereof from the sample;
 (c) amplifying the extracted nucleic acid molecules using the polymerase chain reaction;
 (d) determining the presence of nucleic acid molecules encoding the cancer-associated antigen; and
 (e) comparing the level of the nucleic acid molecules encoding the cancer-associated antigen in the sample to a control sample, wherein increased levels of the nucleic acid molecules encoding the cancer-associated antigen as compared to the control indicates that the subject has cancer.

In a preferred embodiment, the nucleic acid molecule encodes a cancer-associated antigen that comprises SEQ ID NO:2, more preferably SEQ ID NO:1. In a specific embodiment, the nucleic acid molecule comprises the sequence shown in SEQ ID NO:6 or a diagnostic fragment thereof. In another embodiment, the nucleic acid molecule comprises the sequence shown in SEQ ID NO:25 (which encodes the transmembrane fragment shown in SEQ ID NO:2) or a diagnostic fragment thereof.

The methods of the invention described herein may also be performed using microarrays, such as oligonucleotide arrays, cDNA arrays, genomic DNA arrays, or tissue arrays. Preferably the arrays are tissue microarrays.

In a preferred example, an RNA expression product encoding the cancer-associated variant of Mammalian Scratch is used to detect the expression of the cancer-associated variant of Mammalian Scratch by the cell. One skilled in the art will appreciate that the RNA expression product can be detected or quantified by detecting mRNA encoding the cancer-associated variant of Mammalian Scratch or a fragment thereof, or oligonucleotides, cDNA, DNA, RNA, PCR products, synthetic DNA, synthetic RNA, or other combinations of naturally occurring or modified nucleotides which specifically and/or selectively hybridize to the mRNA encoding the cancer-associated variant of Mammalian Scratch or a fragment thereof.

A number of methods can be used to detect and/or quantify RNA expression of the cancer-associated variant of Mammalian Scratch by a cell including RT-PCR, nuclease protection assays, such as ribonuclease protection assays and S1 nuclease assays, and Northern blots and the like.

In a particular embodiment, the inventors have prepared PCR primers that amplify both variant and wildtype scratch (SEQ ID NO:26) or only variant scratch (SEQ ID NO:27) as described in Example 4. Using such primers allows one to distinguish between variant and wild type scratch.

The inventors have also determined that the sequence of wild type Mammalian Scratch contains a KpnI restriction site at nucleotide 118 that is not present in the cancer-associated variant. Therefore, to test if a cancer expresses the variant, the amplified PCR product can be digested with the KpnI restriction enzyme followed by gel electrophoresis. If the cells being tested express wildtype Mammalian Scratch then 2 fragments of 67 bp and 93 bp will be detected. If the cells express the cancer-associated variant then the size of the PCR product will be the same as the undigested control.

Accordingly, the present invention provides a method of detecting cancer cells or monitoring cancer in a subject having or suspected of having cancer comprising:
 (a) providing a sample from the subject;
 (b) extracting nucleic acid molecules encoding wild type scratch or the cancer-associated variant of scratch from the sample;
 (c) digesting the nucleic acid molecules with a KpnI restriction enzyme; and
 (d) determining the size of the digested nucleic acid molecules wherein the presence of undigested nucleic acid molecules indicates that the subject has cancer.

Methods for Detecting the Cancer-Associated Antigen

In another embodiment, the methods of the invention involve the detection of the cancer-associated antigen. In one embodiment, the cancer-associated antigen is detected using antibodies that specifically bind to the cancer-associated antigen. Antibodies to the cancer-associated antigen may be prepared using techniques known in the art.

Antibodies specifically reactive with the cancer-associated antigen, or derivatives, such as enzyme conjugates or labeled derivatives, may be used to detect the cancer-associated antigen in various samples (e.g. biological materials). They may be used as diagnostic or prognostic reagents and they may be used to detect abnormalities in the level of protein expression, or abnormalities in the structure, and/or temporal, tissue, cellular, or subcellular location of the cancer-associated antigen. In vitro immunoassays may also be used to assess or monitor the efficacy of particular therapies. The antibodies of the invention may also be used in vitro to determine the level of expression of a gene encoding the cancer-associated antigen in cells genetically engineered to produce the cancer-associated antigen.

The antibodies may be used in any known immunoassays which rely on the binding interaction between an antigenic determinant of the cancer-associated antigen and the antibodies. Examples of such assays are radioimmunoassays, enzyme immunoassays (e.g. ELISA), immunofluorescence, immunoprecipitation, latex agglutination, hemagglutination, and histochemical tests. The antibodies may be used to detect and quantify the cancer-associated antigen in a sample in order to determine its role in cancer and to diagnose the cancer.

In particular, the antibodies of the invention may be used in immuno-histochemical analyses, for example, at the cellular and subcellular level, to detect an the cancer-associated antigen, to localize it to particular cells and tissues, and to specific subcellular locations, and to quantitate the level of expression.

Cytochemical techniques known in the art for localizing antigens using light and electron microscopy may be used to detect the cancer-associated antigen. Generally, an antibody of the invention may be labeled with a detectable substance and the cancer-associated antigen may be localised in tissues and cells based upon the presence of the detectable substance. Examples of detectable substances include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualised by electron microscopy.

The antibody or sample may be immobilized on a carrier or solid support which is capable of immobilizing cells, antibodies etc. For example, the carrier or support may be nitrocellulose, or glass, polyacrylamides, gabbros, and magnetite. The support material may have any possible configuration including spherical (e.g. bead), cylindrical (e.g. inside surface of a test tube or well, or the external surface of a rod), or flat (e.g. sheet, test strip). Indirect methods may also be employed in which the primary antigen-antibody reaction is amplified by the introduction of a second antibody, having specificity for the antibody reactive against the cancer-associated antigen. By way of example, if the antibody having specificity against the cancer-associated antigen is a rabbit IgG antibody, the second antibody may be goat anti-rabbit gamma-globulin labeled with a detectable substance as described herein.

Where a radioactive label is used as a detectable substance, the cancer-associated antigen may be localized by radioautography. The results of radioautography may be quantitated by determining the density of particles in the radioautographs by various optical methods, or by counting the grains.

Labeled antibodies against the cancer-associated antigen may be used in locating tumor tissue in subjects undergoing surgery i.e. in imaging. Typically for in vivo applications, antibodies are labeled with radioactive labels (e.g. iodine-123, iodine-125, iodine-131, gallium-67, technetium-99, and indium-111). Labeled antibody preparations may be administered to a subject intravenously in an appropriate carrier at a time several hours to four days before the tissue is imaged. During this period unbound fractions are cleared from the subject and the only remaining antibodies are those associated with tumor tissue. The presence of the isotope is detected using a suitable gamma camera. The labeled tissue can be correlated with known markers on the subject's body to pinpoint the location of the tumor for the surgeon.

Accordingly, in another embodiment the present invention provides a method for detecting cancer in a subject comprising:
 (a) providing a sample from the subject;
 (b) contacting the sample with an antibody that binds to the cancer-associated antigen;
 (c) detecting the level of the cancer-associated antigen in the sample; and
 (d) comparing the level of the cancer-associated antigen in the sample to a control sample, wherein increased levels of the cancer-associated antigen as compared to the control indicates that the subject has cancer.

(iii) Therapeutic Methods

As mentioned above, the novel cancer-associated antigen is present on cancer cells, but not significantly on normal cells. Thus, the novel cancer-associated antigen can be used in therapeutic methods to prevent and treat cancer. In addition, the novel cancer-associated antigen or fragments thereof can be used to elicit an immune response in vivo, for example in a vaccine, or in vitro.

One embodiment of the invention is the use of an isolated protein of the invention or fragment thereof in the manufacture of a medicament to treat or prevent cancer. Yet another embodiment of the invention is the use of an isolated protein of the invention or fragment thereof to treat or prevent cancer. A further embodiment of the invention is the use of an isolated protein of the invention or fragment thereof in the manufacture of a medicament to elicit an immune response. Yet another embodiment of the invention is the use of an isolated protein of the invention or fragment thereof to elicit an immune response.

The invention also includes the use of an isolated nucleic acid sequence of the invention in the manufacture of a medicament to treat or prevent cancer. The invention further includes the use of an isolated nucleic acid sequence of the invention to treat or prevent cancer. In addition, the invention includes the use of an isolated nucleic acid sequence of the invention in the manufacture of a medicament to elicit an immune response. The invention further includes the use of an isolated nucleic acid sequence of the invention to elicit an immune response.

A further embodiment of the invention is the use of the recombinant expression vector of the invention in the manufacture of a medicament to treat or prevent cancer. Yet another embodiment of the invention is the use of the recombinant expression vector of the invention to treat or prevent cancer. Also, the invention includes the use of the recombinant expression vector of the invention in the manufacture of a medicament to elicit an immune response in a subject. Yet another embodiment of the invention is the use of the recombinant expression vector of the invention to elicit an immune response in a subject.

An additional embodiment of the invention is a method of treating or preventing cancer comprising administering an effective amount of an isolated protein of the invention or a fragment thereof to a subject or cell in need thereof. In addition, the invention includes a method of treating or preventing cancer comprising administering an effective amount of the isolated nucleic acid sequence of the invention to a subject or cell in need thereof. Further, the invention includes a method of treating or preventing cancer comprising administering an effective amount of the recombinant expression vector of the invention to a subject or cell in need thereof.

Another embodiment of the invention is a method of inducing an immune response in a subject against an isolated protein of the invention, comprising administering an effective amount of the isolated protein of the invention or a fragment thereof to a subject or cell in need thereof. In addition, the invention includes a method of inducing an immune response in a subject against the isolated protein of the invention, comprising administering an effective amount of the isolated nucleic acid sequence of the invention to a subject or cell in need thereof. Further, the invention includes a method of inducing an immune response in a subject against the isolated protein of the invention comprising administering an effective amount of the recombinant expression vector of the invention to a subject or cell in need thereof.

The above methods include both in vivo and in vitro administration of the isolated protein of the invention. For in vitro uses, the protein can be used to stimulate lymphocytes obtained from the patient which are then re-infused into the subject to mount an immune response against the cancer cells expressing the cancer-associated antigen.

A further aspect of the invention is a method of treating or preventing cancer in a subject by modulating the activity or expression of the cancer-associated variant of Mammalian Scratch on or in a cancer cell.

In one embodiment of the invention, the method of treating or preventing cancer in a subject comprises preventing or decreasing the function of the cancer-associated variant of Mammalian. In one embodiment of the invention, a binding protein of the invention is used to prevent or decrease the function of the cancer-associated variant of Mammalian Scratch.

In another embodiment of the invention, the function of the cancer-associated variant of Mammalian Scratch is prevented or decreased by decreasing or preventing the expression of the cancer-associated variant of Mammalian Scratch in the cell.

Standard techniques can be used to prevent or decrease the expression of the cancer-associated variant of Mammalian Scratch in a cell including using antisense, triple helix, or ribozyme molecules reactive to the transcripts of the cancer-associated variant of Mammalian Scratch gene.

For example, standard techniques can be utilized for the production of antisense nucleic acid molecules, i.e., molecules which are complementary to a sense nucleic acid encoding a polypeptide of interest, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of interest. The non-coding regions ("5' and 3' untranslated regions") are the 5' and 3' sequences that flank the coding region and are not translated into amino acids.

An antisense oligonucleotide can be, for example, about 5, 10, 15, 20, 25, 30, 35, 40, 45 or 50 nucleotides or more in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Antisense nucleic acid molecules administered to a subject or generated in situ such that they hybridize with or bind to cellular mRNA encoding the polypeptide of interest to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell, e.g., a T cell or brain cell, e.g., by linking the antisense nucleic acid molecules to peptides or antibodies which bind to cell surface receptors or antigens. The antisense nucleic acid molecules can also be delivered to cells using vectors, e.g., gene therapy vectors, described below. To achieve sufficient intracellular concentrations of the antisense molecules, vector constructs in which the antisense nucleic acid molecule is placed under the control of a strong pol II or pol III promoter are preferred.

An antisense nucleic acid molecule of interest can be an α-anomeric nucleic acid molecule. An α-anomeric nucleic acid molecule forms specific double-stranded hybrids with complementary RNA in which, contrary to the usual α-units, the strands run parallel to each other (Gautier et al., 1987, Nucleic Acids Res. 15:6625-6641). The antisense nucleic acid molecule can also comprise a 2'-o-methylribonucleotide (Inoue et al., 1987, Nucleic Acids Res. 15:6131-6148) or a chimeric RNA-DNA analogue (Inoue et al., 1987, FEBS Lett. 215:327-330).

Ribozymes are catalytic RNA molecules with ribonuclease activity that are capable of cleaving a single-stranded nucleic acid, such as an mRNA, to which they have a complementary region, and can also be generated using standard techniques. Thus, ribozymes (e.g., hammerhead ribozymes (described in Haseloff and Gerlach, 1988, Nature 334:585-591)) can be used to catalytically cleave mRNA transcripts to thereby inhibit translation of the protein encoded by the mRNA. A ribozyme having specificity for a nucleic acid molecule encoding a polypeptide of interest can be designed based upon the nucleotide sequence of a cDNA encoding a cancer-associated variant of Mammalian Scratch. For example, a derivative of a Tetrahymena L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a polypeptide of interest can be used to select a catalytic RNA having a specific ribonuclease activity from a pool of RNA molecules. See, e.g., Bartel and Szostak, 1993, Science 261:1411-1418.

Triple helical structures can also be generated using well known techniques. For example, expression of a polypeptide of interest can be inhibited by targeting nucleotide sequences complementary to the regulatory region of the gene encoding the polypeptide (e.g., the promoter and/or enhancer) to form triple helical structures that prevent transcription of the gene in target cells. See generally Helene, 1991, Anticancer Drug Des. 6(6):569-84; Helene, 1992, Ann. N.Y. Acad. Sci. 660: 27-36; and Maher, 1992, Bioassays 14(12):807-15.

In various embodiments, nucleic acid compositions can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, Bioorganic & Medicinal Chemistry 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al., 1996, supra; Perry-O'Keefe et al., 1996, Proc. Natl. Acad. Sci. USA 93: 14670-675.

PNAs can, for example, be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup, 1996, supra, and Finn et al., 1996, Nucleic Acids Res. 24(17):3357-63. For example, a DNA chain can be synthesized on a support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, Nucleic Acids Res. 17:5973-88). PNA monomers are then coupled in a stepwise manner to produce a chimeric molecule with a 5' PNA segment and a 3' DNA segment (Finn et al., 1996, Nucleic Acids Res. 24(17):3357-63). Alternatively, chimeric molecules can be synthesized with a 5' DNA segment and a 3' PNA segment (Petersen et al., 1995, Bioorganic Med. Chem. Lett. 5:1119-1124).

In other embodiments, the oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. USA 86:6553-6556; Lemaitre et al., 1987, Proc. Natl. Acad. Sci. USA 84:648-652; International Publication No. WO 88/09810) or the blood-brain barrier (see, e.g., International Publication No. WO 89/10134). In addition, oligonucleotides can be modified with hybridization-triggered cleavage agents (see, e.g., van der Krol et al., 1988, Bio/Techniques 6:958-976) or intercalating agents (see, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

Another aspect of the invention is a method to identify compounds that are able to modulate the expression or activity of the cancer-associated variant of Mammalian Scratch, which can be used to prevent or treat cancer. In one embodiment of the invention, the method for identifying a compound for ability to prevent or treat cancer comprises the steps:

(a) contacting a cell expressing a cancer-associated variant of Mammalian Scratch with a test compound; and
(b) determining the expression or function of the cancer-associated variant of Mammalian Scratch; and
(c) comparing the expression or function of the cancer-associated variant of Mammalian Scratch to a control, wherein a decrease in expression or function of the cancer-associated variant of Mammalian Scratch as compared to the control is indicative of a compound useful to prevent or treat cancer.

(D) Binding Proteins

Another aspect of the invention is a binding protein, preferably an antibody or antibody fragment, that binds to the isolated proteins of the invention. Such a binding protein can be generally referred to herein as "a binding protein of the invention", or preferably "an antibody or antibody fragment of the invention".

In one embodiment, the invention includes a binding protein that is specific for a cancer-associated variant of Mammalian Scratch. In a preferred embodiment, the cancer-associated variant of Mammalian Scratch comprises the amino acid sequence defined by SEQ ID NO:1 or a variant thereof or the amino acid sequence defined by SEQ ID NO:2 or a variant thereof. In another embodiment, the binding proteins bind to an isolated protein comprising the amino acid sequence defined by SEQ ID NO:1 or a variant thereof or the amino acid sequence defined by SEQ ID NO:2 or a variant thereof.

In certain embodiments, the antibody or antibody fragment comprises all or a portion of a heavy chain constant region, such as an IgG1, IgG2, IgG3, IgG4, IgA1, IgA2, IgE, IgM or IgD constant region. Furthermore, the antibody or antibody fragment can comprise all or a portion of a kappa light chain constant region or a lambda light chain constant region.

The isolated proteins of the invention may be used to prepare monoclonal or polyclonal antibodies. Conventional methods can be used to prepare the antibodies. For example, see Goding, J. W., Monoclonal Antibodies: Principles and Practice, $2^{nd}$ Ed., Academic Press, London, 1986.

Specific antibodies, or antibody fragments, reactive against particular antigens or molecules, such as antigens or molecules on a cancer cell, may also be generated by screening expression libraries encoding immunoglobulin genes, or portions thereof, expressed in bacteria with cell surface components. For example, complete Fab fragments, VH regions and FV regions can be expressed in bacteria using phage expression libraries (See for example Ward et al., Nature 341:544-546 (1989); Huse et al., Science 246:1275-1281 (1989); and McCafferty et al., Nature 348:552-554 (1990)).

The invention also provides compositions comprising the binding proteins of the invention, preferably antibodies and antibody fragments, with a pharmaceutically acceptable excipient, carrier, buffer or stabilizer.

In addition, the binding proteins of the invention can be used in the diagnosis of cancer.

In a preferred embodiment, the binding proteins are antibodies or antibody fragments that bind to cancer-associated variants of Mammalian Scratch that is expressed on the surface of cancer cells, preferably an isolated protein comprising any one of the amino acid sequences of SEQ ID NOS: 1 or 2. In addition, cancer cells may be evaluated to determine their susceptibility to the treatment methods of the invention by, for example, obtaining a sample of the cancer cells and determining the ability of the sample to bind to the binding proteins of the invention, preferably antibodies or antibody fragments.

Accordingly, the present invention includes diagnostic methods, agents, and kits that can be used by themselves or prior to, during or subsequent to the therapeutic method of the invention in order to determine whether or not cancer cells are present that express the antigen and can bind to the binding proteins of the invention, preferably antibodies and antibody fragments.

In one embodiment, the invention provides a method of detecting or monitoring cancer in a subject comprising the steps of
(1) contacting a test sample taken from said subject with a binding protein that binds specifically to an antigen on the cancer cell to produce a binding protein-antigen complex;
(2) measuring the amount of binding protein-antigen complex in the test sample; and
(3) comparing the amount of binding protein-antigen complex in the test sample to a control.

In one embodiment, the antigen is a cancer-associated variant of Mammalian Scratch, preferably an isolated protein comprising any one of the amino acid sequences of SEQ ID NOS:1-2.

The invention further includes a kit for detecting or monitoring cancer comprising any one of the binding proteins of the invention that binds to an antigen on the cancer cell and instructions for the use thereof.

For use in the diagnostic applications, the binding proteins of the invention, preferably antibodies or antibody fragments, may be labeled with a detectable marker such as a radioopaque or radioisotope, such as $^3$H, $^{14}$C, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion. As described above, methods of attaching a label to a binding protein, such as an antibody or antibody fragment, are known in the art.

Another aspect of the invention is a method of detecting or monitoring cancer in a subject comprising the steps of
(1) measuring the amount of antibodies of the invention in a test sample taken from said subject; and
(2) comparing the amount of antibodies of the invention in the test sample to a control.

In one embodiment, the amount of antibodies of the invention is measured by measuring the amount of antibodies of the invention in the test sample, for example by ELISA. In another embodiment, the amount of antibodies of the invention is measured by measuring the expression levels of nucleic acids encoding the antibodies of the invention in the test sample, for example by RT-PCR.

(E) Preparation of Proteins of the Invention

A person skilled in the art will appreciate that the proteins of the invention, such as the novel cancer-associated antigen, the binding proteins, preferably antibodies and antibody fragments, may be prepared in any of several ways, but is most preferably prepared using recombinant methods.

Accordingly, the nucleic acid molecules of the present invention may be incorporated in a known manner into an appropriate expression vector which ensures good expression of the proteins of the invention. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence.

Suitable regulatory sequences may be derived from a variety of sources, including bacterial, fungal, viral, mammalian, or insect genes (for example, see the regulatory sequences described in Goeddel, Gene Expression Technology Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms "transformed with", "transfected with", "transformation" and "transfection" are intended to encompass introduction of nucleic acid (e.g. a vector) into a cell by one of many possible techniques known in the art. The term "transformed host cell" as used herein is intended to also include cells capable of glycosylation that have been transformed with a recombinant expression vector of the invention. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 3rd Edition, Cold Spring Harbor Laboratory Press, 2001), and other laboratory textbooks.

Suitable host cells include a wide variety of eukaryotic host cells and prokaryotic cells. For example, the proteins of the invention may be expressed in yeast cells or mammalian cells. Other suitable host cells can be found in Goeddel, Gene Expression Technology: Methods in Enzymology 185, Academic Press, San Diego, Calif. (1990). In addition, the proteins of the invention may be expressed in prokaryotic cells, such as *Escherichia coli* (Zhang et al., Science 303(5656): 371-3 (2004)). In addition, a *Pseudomonas* based expression system such as *Pseudomonas fluorescens* can be used (US Patent Application Publication No. US 2005/0186666, Schneider, Jane C et al).

Yeast and fungi host cells suitable for carrying out the present invention include, but are not limited to *Saccharomyces cerevisiae*, the genera *Pichia* or *Kluyveromyces* and various species of the genus *Aspergillus*. Examples of vectors for expression in yeast *S. cerevisiae* include pYepSec1 (Baldari. et al., Embo J. 6:229-234 (1987)), pMFa (Kurjan and Herskowitz, Cell 30:933-943 (1982)), pJRY88 (Schultz et al., Gene 54:113-123 (1987)), and pYES2 (Invitrogen Corporation, San Diego, Calif.). Protocols for the transformation of yeast and fungi are well known to those of ordinary skill in the art (see Hinnen et al., Proc. Natl. Acad. Sci. USA 75:1929 (1978); Itoh et al., J. Bacteriology 153:163 (1983), and Cullen et al. (Bio/Technology 5:369 (1987)).

Mammalian cells suitable for carrying out the present invention include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)) and pMT2PC (Kaufman et al., EMBO J. 6:187-195 (1987)).

Given the teachings provided herein, promoters, terminators, and methods for introducing expression vectors of an appropriate type into plant, avian, and insect cells may also be readily accomplished. For example, within one embodiment, the proteins of the invention may be expressed from plant cells (see Sinkar et al., J. Biosci (Bangalore) 11:47-58 (1987), which reviews the use of *Agrobacterium rhizogenes* vectors; see also Zambryski et al., Genetic Engineering, Principles and Methods, Hollaender and Setlow (eds.), Vol. VI, pp. 253-278, Plenum Press, New York (1984), which describes the use of expression vectors for plant cells, including, among others, PAPS2022, PAPS2023, and PAPS2034).

Insect cells suitable for carrying out the present invention include cells and cell lines from *Bombyx, Trichoplusia* or *Spodotera* species. Baculovirus vectors available for expression of proteins in cultured insect cells (SF 9 cells) include the pAc series (Smith et al., Mol. Cell. Biol. 3:2156-2165 (1983)) and the pVL series (Luckow, V. A., and Summers, M. D., Virology 170:31-39 (1989)). Some baculovirus-insect cell expression systems suitable for expression of the recombinant proteins of the invention are described in PCT/US/02442.

Alternatively, the proteins of the invention may also be expressed in non-human transgenic animals such as mouse, rats, rabbits, sheep and pigs (Hammer et al. Nature 315:680-683 (1985); Palmiter et al. Science 222:809-814 (1983); Brinster et al. Proc. Natl. Acad. Sci. USA 82:4438-4442 (1985); Palmiter and Brinster Cell 41:343-345 (1985) and U.S. Pat. No. 4,736,866).

The proteins of the invention may also be prepared by chemical synthesis using techniques well known in the chemistry of proteins such as solid phase synthesis (Merrifield, J. Am. Chem. Assoc. 85:2149-2154 (1964); Frische et al., J. Pept. Sci. 2(4): 212-22 (1996)) or synthesis in homogenous solution (Houbenweyl, Methods of Organic Chemistry, ed. E. Wansch, Vol. 15 I and II, Thieme, Stuttgart (1987)).

N-terminal or C-terminal fusion proteins comprising the proteins of the invention conjugated with other molecules, such as proteins may be prepared by fusing, through recombinant techniques. The resultant fusion proteins contain a protein of the invention fused to the selected protein or marker protein as described herein. The recombinant protein of the invention may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate. Examples of proteins which may be used to prepare fusion proteins or conjugates include cell binding proteins such as immunoglobulins, hormones, growth factors, lectins, insulin, low density lipoprotein, glucagon, endorphins, transferrin, bombesin, asialoglycoprotein glutathione-S-transferase (GST), hemagglutinin (HA), and truncated myc.

Accordingly, the invention provides a recombinant expression vector comprising the nucleic acid sequences that encode the proteins of the invention, such as the isolated proteins of the invention. Further, the invention provides a host cell comprising the recombinant expression vector of the invention.

The following non-limiting examples are illustrative of the present invention:

EXAMPLES

Example 1

Isolation and Identification of Cancer Associated Scratch

Experimental Design

Melanoma cell line (A-375), glioma cell lines (U118MG and U87MG), breast cancer cell line (MDA-MB 435S), pancreatic cell line, (PANC-1) and T-cell line (Daudi) were used in the study (Table 1). These cell lines were selected based on the results of tumor cell line profiling by flow cytometry.

Growth and Maintenance of Tumor Cell Lines

The cell lines in the study were purchased from ATCC and cultured in accordance with the guidelines and recommendations of ATCC. Cells were harvested at 90% confluence with viability >90%.

Preliminary Characterization of the Antigen Binding to VB3-011

Preliminary characterization data was obtained from experiments designed to assess the feasibility of the gel-based approach by dot blot assays; and from experiments performed to determine the nature of the epitope associated with the antigens.

The data from these experiments classified the VB3-011 antigen as a "non-blottable" antigen with a glycan modification, i.e., the epitope involved in binding to VB3-011 on the antigen was glycosylated.

VB3-011 Ag Enrichment and Purification

The preliminary data from the blottability study specified a lectin-based purification method as the best antigen preparation method for VB3-011. Extensive experimentation revealed that the glycan modification involved a soluble form of CS (chondroitin sulphate); two of these (CSB and CSE) have limited tissue distribution. As such, the glycan modification could be attributable to CSA and to a lesser extent hyaluronic acid.

Chondroitin sulphate A (CSA) is made up of linear repeating units containing D-galactosamine and D-glucuronic acid. The amino group of galactosamines in the basic unit of chondroitin sulfate A is acetylated, yielding N-acetyl-galactosamine; there is a sulfate group esterified to the 4-position in N-acetyl-galactosamine (FIG. 1A) (Sugahara K et al. 1988. J. Biol. Chem. Vol. 263:10168-10174; Sugahara K et al. 1991. Eur. J. Biochem. Vol. 202:805-811; Prydz K and Dalen K T. 2000. J. Cell Sci. Vol. 113:193-205). When these linear repeating units get cross-linked ($\alpha$ 2-6) at branch points at C2 of the second and C6 of the first carbon chains, such that a single unit of glycan representing more than one linear chains of CSA are present, except for the sulfation, it resembles the glycan, Neu5Ac ($\alpha$ 2→6) Gal($\beta$ 1→4) Glucuronate, recognized by HA (FIG. 1B).

Two or more CSA molecules when cross-linked together resemble the glycan—Neu5Ac ($\alpha$ 2→6) Gal ($\beta$ 1→4) Glucuronate, recognized by Hemagglutinin (HA), Azumi et al., (1991) showed that the activity of a hemagglutinin isolated from hemocytes of the ascidian, Halocynthia roretzi was inhibited by heparin, chondroitin sulfate, and lipopolysaccharide (LPS), but not by mono-and disaccharides such as N-acetyl-galactosamine, galactose, and melibiose. The hemagglutinin showed binding ability to heparin, chondroitin sulfate and LPS, as demonstrated by heparin-Sepharose chromatography and centrifugation experiments, respectively (Ajit Varki et al eds. 1999. Essentials of Glycobiology). Similarly, a Hemagglutinin from mycobacterium was shown to bind to heparan sulfate and Hemagglutinin from *Hemophilus influenzae* binds to CSA with an additional $\alpha$ 2-6 linkage (Azumi K et al. A1991. Dev. Comp. Immunol. Vol. 15(1-2): 9-16; Menozzi F D et al. 11996. J. Exp. Med., Vol. 184(3): 993-1001). Heparan sulfate and Chondroitin sulfate A differ in C5 epimerization. Therefore, a new reagent that would enable lectin-based purification was generated as follows. Recombinant HA was immobilized to anti-HA antibody by coupling with Dimethylpimelimidate (DMP), such that when used as an IP agent, HA recognizes the CSA associated with the antigen on the cell surface. Membrane preparations were affinity purified with immobilized-HA, and the eluates subjected to SDS-PAGE and WB analysis, subsequently probed with VB3-011 antibody.

Lectin-Based Purification

Recombinant HA molecule that binds specifically to the glycan—Neu5Ac ($\alpha$ 2→6) Gal ($\beta$ 1→4) Glc, was made to bind to anti-HA antibody for 2 hours at room temperature on the nutator, followed by binding of the HA-anti-HA complex to Protein-G-sepharose. This was followed by a centrifugation step to get rid of the unbound fraction. The immobilized complex was then cross-linked using Dimethylpimelimidate (DMP) that is known cross-link proteins present in close proximities. The excess or unused cross-linker and the unbound material were removed by a brief centrifugation step. The non-specific amine groups that could have arisen as a by-product of the cross-linking step were neutralized with Triethanolamine for two hours at room temperature. The lectin-based reagent thus created was washed thoroughly with PBS and stored with PBS containing 0.05% NaN3 at 2-8° C. Apart from the HA-reagent, Con-A-agarose and WGA-agarose were also used as affinity purification reagents to detect better antigen recovery.

A minimum of 500 μg membrane protein was used for the lectin-based purification. A pre-clearing step using protein-G sepharose alone was the first step in the purification of the antigen prior to the addition of the reagent. A total of 15-20 μL of the reagent was used as the precipitating agent in the mixture. The antigen-lectin mixtures were nutated overnight at 4° C. using buffer conditions that mimicked physiologic conditions. Care was taken to ensure that protease inhibitors were used in every step of the antigen isolation process.

Antigen-lectin complexes were centrifuged, washed with RIP-A lysis buffer and eluted with 0.2 M glycine pH 2.5. Supernatants representing the unbound fractions were stored to test the proteins that were not isolated by affinity purification. Lectin-based purifications were carried out on two glioma cell lines (U118MG and U87MG), one melanoma cell line (A-375), one epithelial cell line (MDA-MB-435S) and two negative cell lines (Panc-1; and Daudi).

Gel-Based Analysis and Western Blotting

1D-PAGE: The purified proteins were subjected to reducing conditions of sample preparation and were subsequently analyzed by SDS-PAGE/Western Blotting. When reducing conditions were used, the isolated antigens were treated with sample buffer containing 1% β-mercaptoethanol at 65° C. for 15 minutes. The resulting blots were probed with VB3-011 and corresponding secondary antibodies conjugated to HRP, to visualize the purified proteins by chemiluminescence.

2D-PAGE: The purified proteins were separated by two-dimensional gel electrophoresis to resolve any protein stacking effect that may have occurred in the 1D-PAGE analysis. The 2D-gel electrophoresis resolved proteins according to their isoelectric points (pI) in the first dimension and on the basis of their molecular weights in the second dimension. Proteins thus resolved were transferred to nitrocellulose membranes, overnight, and processed as in the case of 1D-PAGE. Western blots were probed with VB3-011 and reacting proteins visualized by chemiluminescence.

Peptide Extraction and Antigen ID

Peptide extraction from in-gel and in-solution tryptic digests: Tryptic digestions were performed with sequencing grade trypsin in a 20-hour peptide extraction process finally resulting in the extraction of peptides that were analyzed on a QSTAR Pulsar-I (ESI-qTOF-MS/MS), equipped with a nanosource with a working flow rate of 20-50 nL/min. The peptides ionize and are detected as doubly, triply or quadruply charged molecules which are then refined to their respective masses. De-novo sequencing of the identified proteins was also performed whenever possible. Peptides were extracted from both positive and negative cell lines to ensure it was the right antigen. Peptide masses extracted from the mass spectra were used directly to identify the antigen according to the MOWSE scores obtained on protein databases that are accessible through the MASCOT search engine. Peptides were extracted both from gel slices and in-solution (U118MG, U87MG, A-375, 435S) and subjected them to MS analysis.

Results

HA Reagent Immobilization

Recombinant HA molecule is not an antibody and therefore does not bind to protein-G-sepharose directly as an immobilizing partner. In order to make it possible for this molecule to be functional in antigen purification processes, HA was bound to anti-HA antibody that would bind specifically to HA, the molecule was immobilized using protein-G-sepharose in a sequential manner. This would not only immobilize the complex but would block any non-specific interaction that could arise from the presence of the anti-HA, as shown schematically in FIG. 2. The immobilized HA-anti-HA complex was thereafter stabilized using Dimethyl pimelimidate, a cross-linking agent that maintained the proximities of the various reactants. The final complex generated a few reactive amines in the process, other than the reactive binding site on the HA molecule. These reactive groups were blocked permanently using 1M triethanolamine, thus ensuring the maximal exposure of the reactive site on the HA molecule.

Lectin-Purification

All purification reactions were performed with pre-cleared proteins. Longer incubation times were used to minimize non-specificity and enhance the stability of cognate antigen-antibody complexes. Six cell lines (A-375, U118MG, U87MG, MDA-MB-435S, Panc-1 and Daudi) were used in the study. Reducing conditions for sample preparations were employed prior to the resolution of the antigens isolated on SDS-PAGE. The Western blots were probed with VB3-011 to ensure that the antigen purified is the cognate binding partner for VB3-011.

1D-PAGE/Western Analysis

Figure 4:
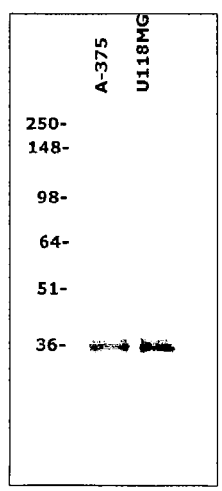
FIG. 4 shows the disappearance of the glycan residue due to degradation at room temperature. A 50 kDa band usually observed on IP with HA reagent, when let to sit at room temperature for an hour prior to separation on SDS-PAGE, resulted in the degradation of the glycan residue, thus showing the presence of a protein band devoid of the glycan portion of the antigen at 36 kDa.

When HA reagent was used, only one specific band was detected after separation on a 1D-PAGE at ~50 kDa under reducing conditions (FIG. 3A) in antigen-positive cell line (A-375), that was absent in the negative cell line (Panc-1). Non-specific interactions were observed with Con-A and WGA lectins indicating that the glycan present on the VB3-011 antigen was the one recognized by HA. Glioma cell line (U118MG and U87MG) also showed the presence of a single band at ~50 kDa when purified using the HA reagent (FIG. 3B). When samples were allowed to sit at room temperature for 1 hour prior to their separation on SDS-PAGE, a predominant band at ~36 kDa and a faint 50 kDa band were observed in antigen-positive cell line (A-375, U118MG and U87MG) (FIG. 4).

2D-PAGE Analysis

In order to determine isoelectric points (pI) and assess the possibility of protein stacking in the 1D-PAGE analysis, the antigens purified by HA were separated on two-dimensional polyacrylamide gel electrophoresis (2D-PAGE), where the separation in the first dimension is on the basis of pI and the second dimension on the basis of molecular weight. The gels were then transferred to nitrocellulose membranes and subjected to standard Western blotting processing. Since the amounts required for the detection of proteins on a 2D gel is ~4 times higher than the requirement for a 1D gel, purified antigens from 4 separate reactions were pooled together for one 2D-PAGE analysis. Two separate gels were processed simultaneously for Western blot analysis to ensure that the proteins detected on the Coomassie stained gels are the same as those observed in the Western blots. The 2D Western blots were probed with VB3-011 and detected by ECL (chemiluniescence). As can be seen in FIG. 5, one single spot was detected at ~36 kDa/pI=9.7±0.2.

Peptide Extraction and Protein Analysis

A-375, U 87MG and U118 MG membranes were used to purify antigen(s) that bind specifically to VB3-011. A ~50 kDa band was observed in all three cell lines as shown in FIGS. 3A and 3B. The protein bands were excised from the coomassie stained gels and used in-gel digestion to extract peptides for MS analysis.

Proteins from 1D-gel band and 2D-spots were digested with trypsin to release them from the gel and analyzed on a reverse-phase LC-MS/MS system. The identities of the proteins were revealed by database analysis using bioinformatic tools. Raw data included peptides obtained as listed in the TOF-MS spectra, MS/MS fragmentation data, and a list of suggested proteins including contaminants that do not match the pI or the molecular weight of the protein isolated. To obtain the analysis MS/MS spectra were submitted directly to Mascot search engines available at www.Matrixscience.com.

Mass Spectral Analysis

Peptide analysis was done in two ways:
  All the peptides recovered and reconstructed to their right masses were used directly in a peptide mass fingerprinting step to obtain an ID for the protein.
  Peptides that were abundant and well ionized were chosen for further MS/MS ion fragmentation, wherein, the 'y' and 'b' ions were used to deduce their primary structure. These sequences were then searched for homologies in the protein database for protein ID.

Peptides ionize and are detected as doubly, triply or quadruply charged molecules, on a LC-MS/MS system as opposed to detection as singly charged on Matrix assisted ionization such as in MALDI. Differentially charged peptides were thereafter refined to their respective masses, in the mass reconstruction step. These peptide masses were then directly analyzed by a matrix science based mascot search engine for antigen ID. Peptide masses extracted from the mass spectra were used directly to identify the antigen according to the MOWSE scores obtained on protein databases that are accessible through search engines such as MASCOT, SEQUEST, and Prospector. QSTAR-pulsar-I was used and selected for all protein identities, because it includes the most recent protein database additions from Pepsea is compatible with MASCOT.

Analysis of 2D Spot

Protein spot excised from the 2D-gel identified Scratch. The pI and the molecular weight clearly matched Mammalian Scratch. A total of 37% sequence coverage with 15 matching peptides, each peptide showing 100% homology to the original protein was recovered (See FIG. 6).

Analysis of the 50 kDa Band Purified from the Glioma and Melanoma Cell Lines

The data obtained from the mass spectra of all three cell lines, (U87MG, U118MG and A375) point towards Mammalian Scratch as the antigen that binds to VB3-011. Of all the cell lines screened, glioma cell lines (U87MG and U118MG) showed the highest scoring identities. A-375, a melanoma cell line also showed an over-expression of the antigen. Apart from the above mentioned cell lines, epithelial cell lines such as MDA-MB-435S, PC-3, A-549 and CFPAC-1 were also screened in the same manner, but except for MDA-MB-435S, which showed the presence of a truncated version of Scratch, i.e., 17.823 kDa protein gi|15928387, with 100% homology to sequences 158-366 of the original scratch molecule. See FIG. 7 (SEQ ID NO:4). The membrane preparations from each of these cell lines were used to affinity purify the VB3-011 antigen using the HA-reagent. Rest of the epithelial cell lines showed no detectable proteins.

Figure 9A:
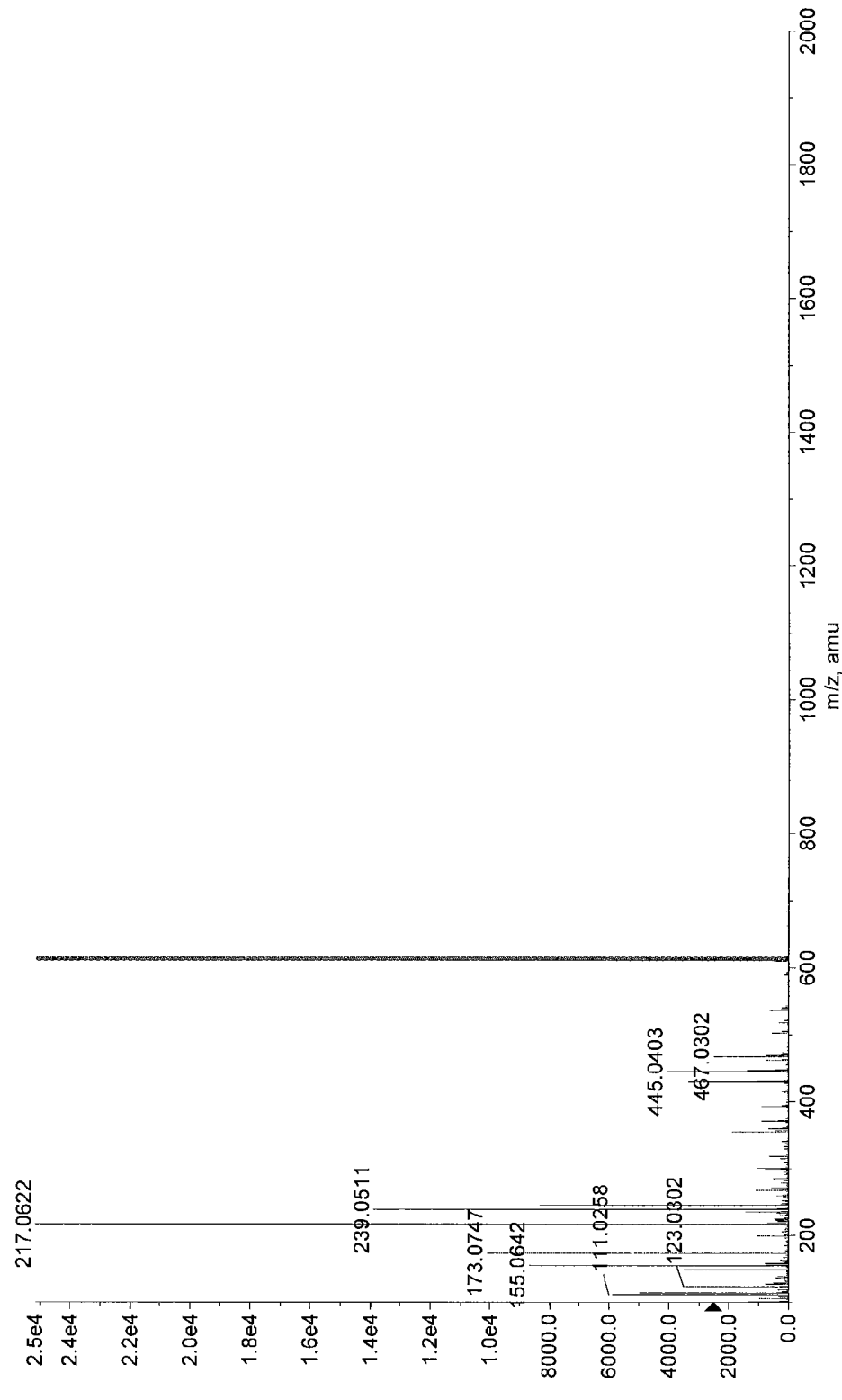
FIG. 9A represents the TOF-MS scan with all multiply charged peptide ions and FIG. 9B represents the deconvoluted spectrum with singly charged peptide ions.
Figure 9B:
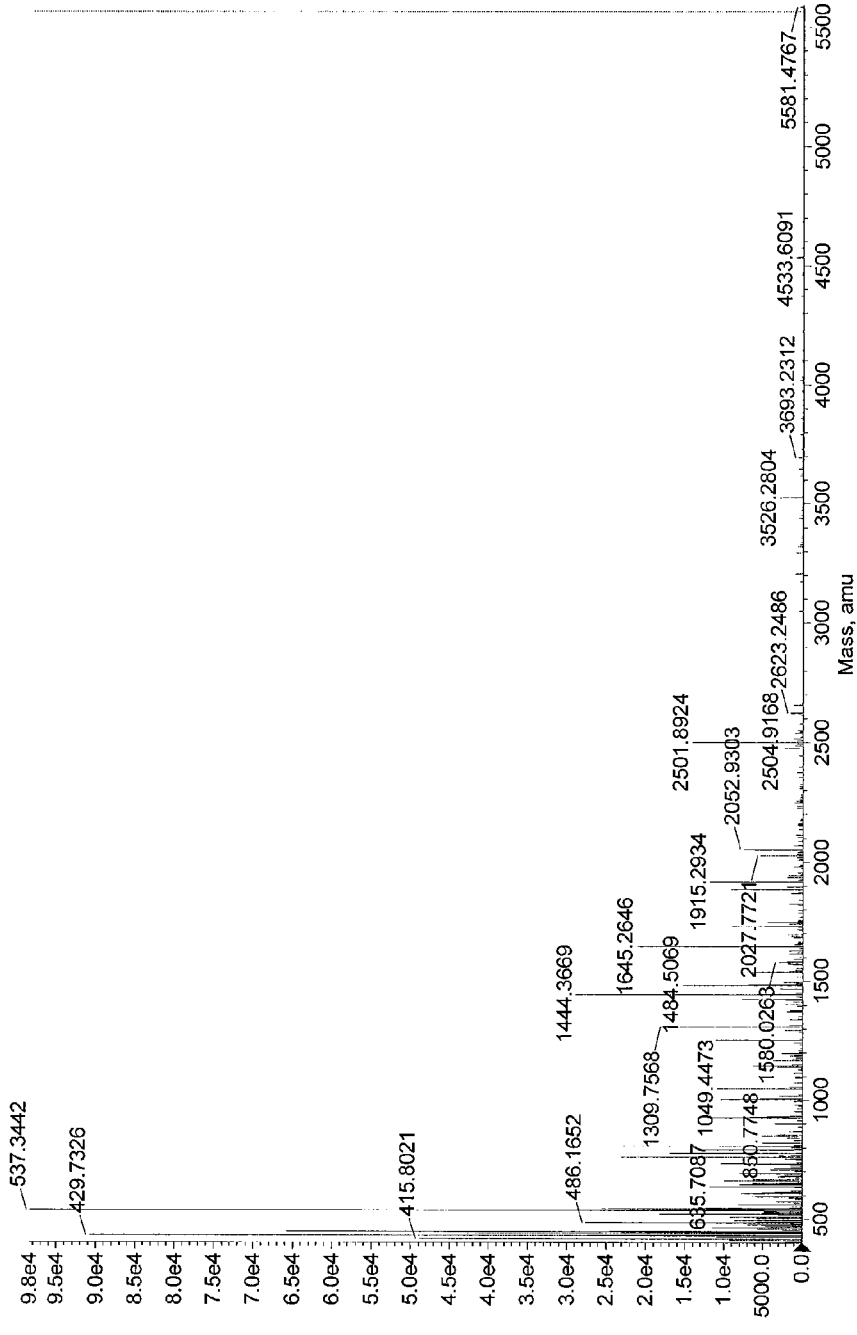
Figure 10A:
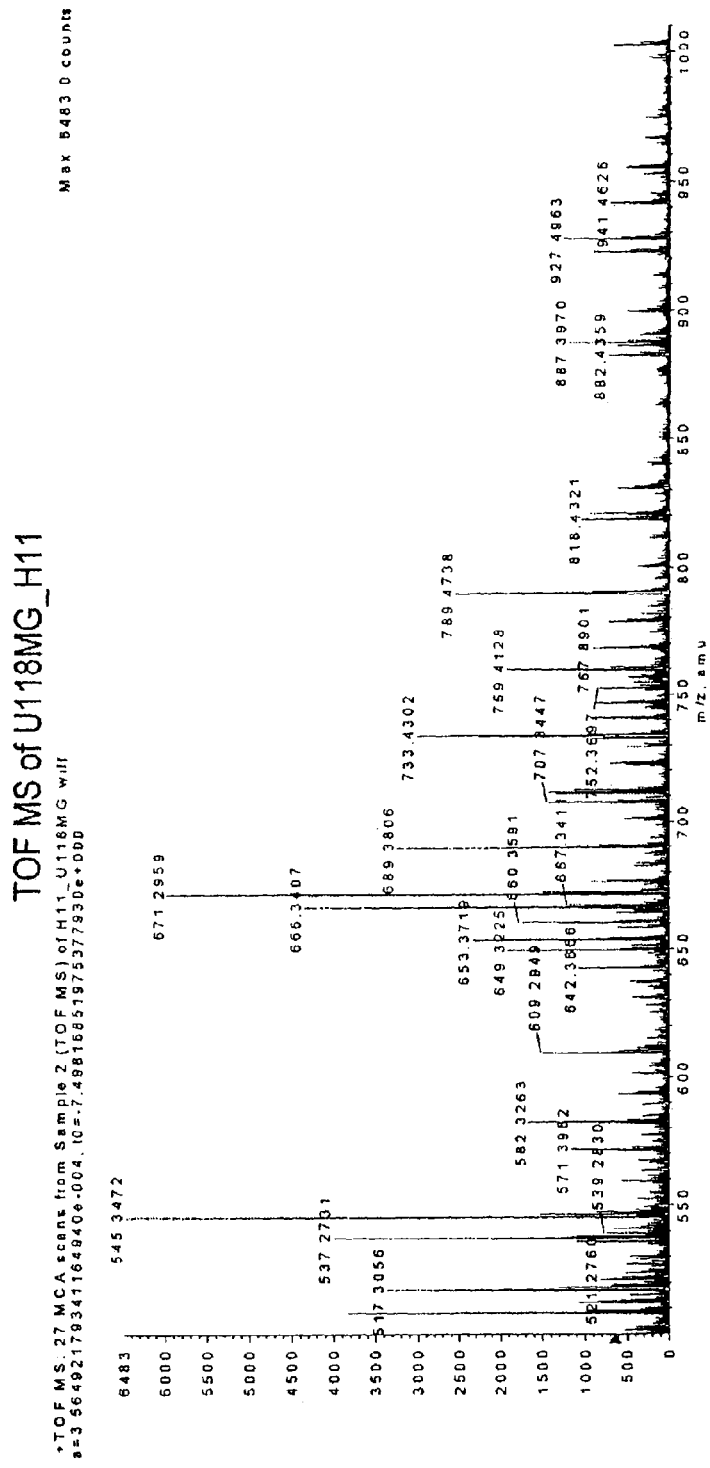
FIG. 10A represents the TOF-MS scan with all multiply charged peptide ions and FIG. 10B represents the deconvoluted spectrum with singly charged peptide ions.
Figure 10B:
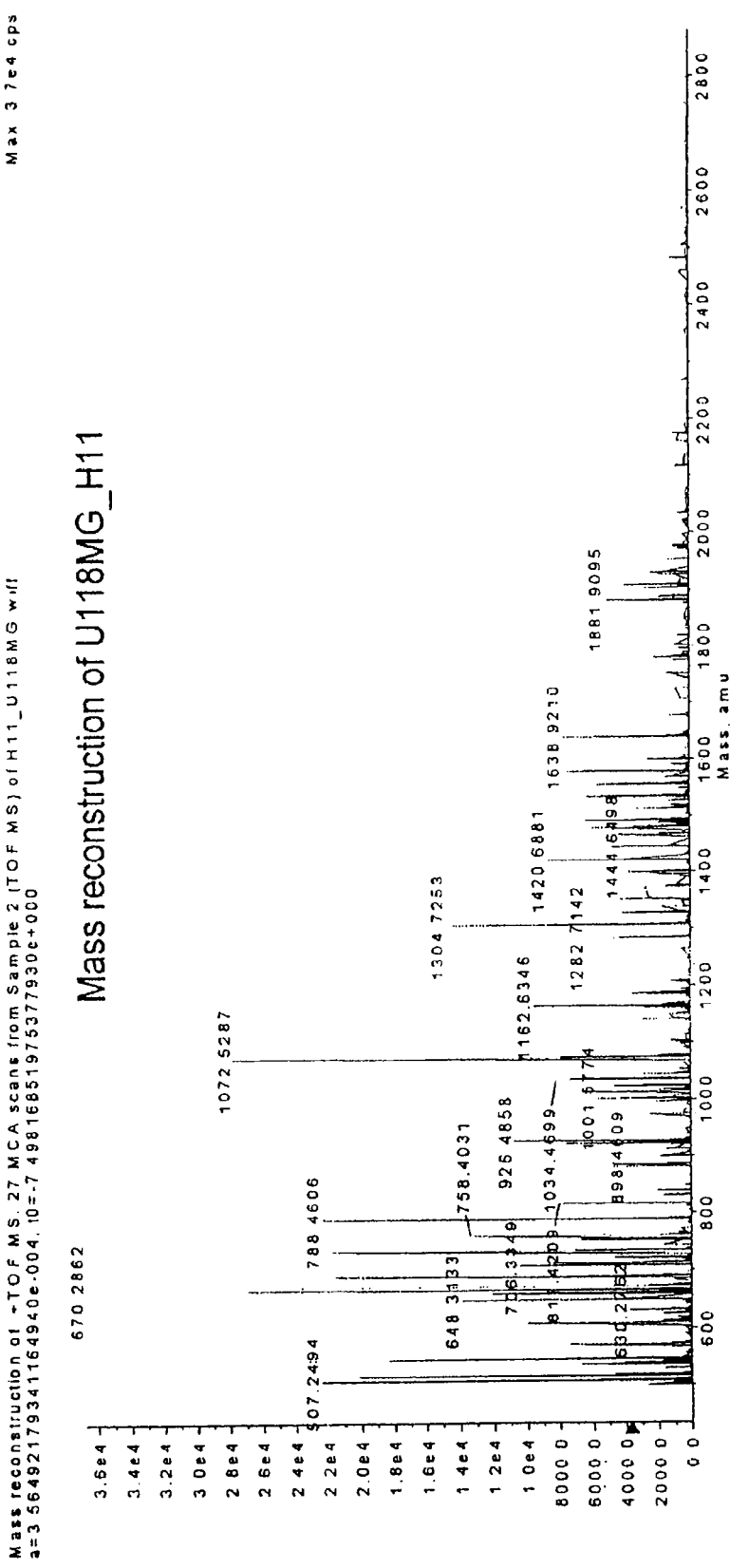

TOF-MS scans were obtained both on a manual mode and an IDA mode to recover the maximum number of peptides for a significant ID. See FIGS. 8-10.

The list of peptides recovered and their mapped positions to the sequence from Mammalian Scratch are as given in FIG. 11 (SEQ ID NO:1) and Table 2 (SEQ ID NOS:2 and 7 to 24). All peptides represented were obtained by de novo sequencing.

MS/MS Fragmentation of Peptide 2402.1206 and 2134.9614

Figure 14:
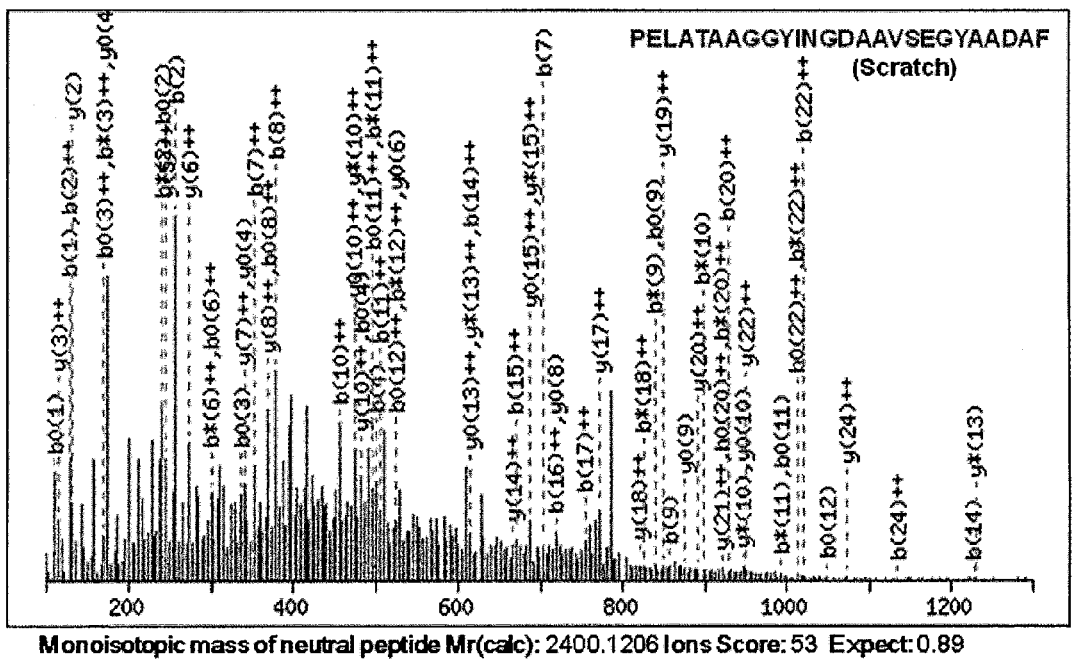
FIG. 14 shows the MS/MS ion fragmentation of the neutral peptide Mr. 2402.978172, appearing as a triply charged molecule (802.00000, 3+). The peptide sequence (residues 92-117 of SEQ ID NO:3) exactly matched the peptide from Scratch.
Figure 15:
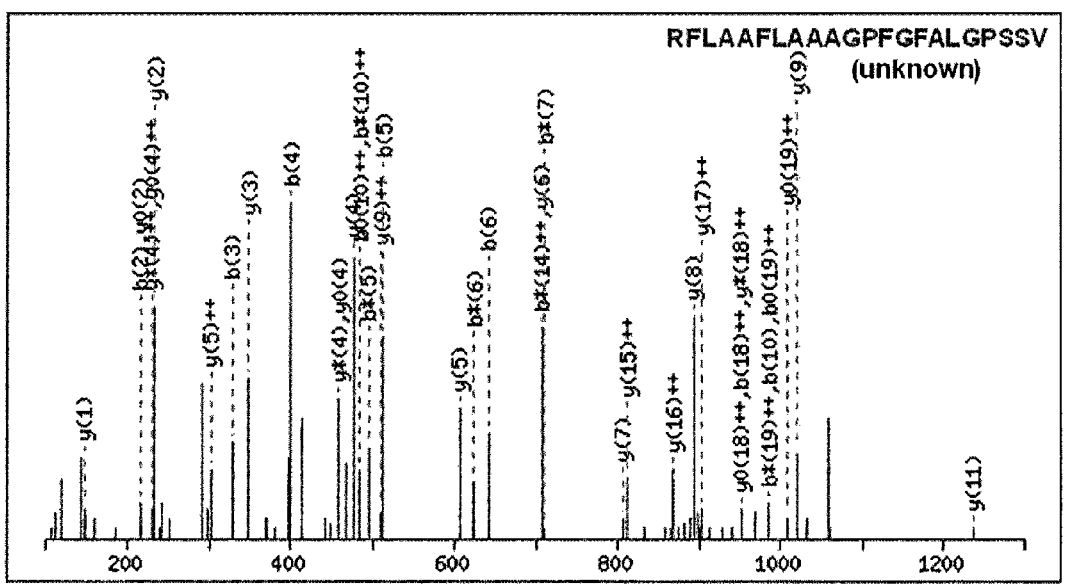
FIG. 15 shows the MS/MS ion fragmentation of the neutral peptide Mr. 2134.985448, appearing as a doubly charged molecule (1068.500000, 2+). The flanking regions of the recovered peptide exactly matched the peptide from Scratch; however the rest of the sequence showed not more than 40% homology in the sequence information. The peptide sequence is residues 2-23 of SEQ ID NO:2.
Figure 16:
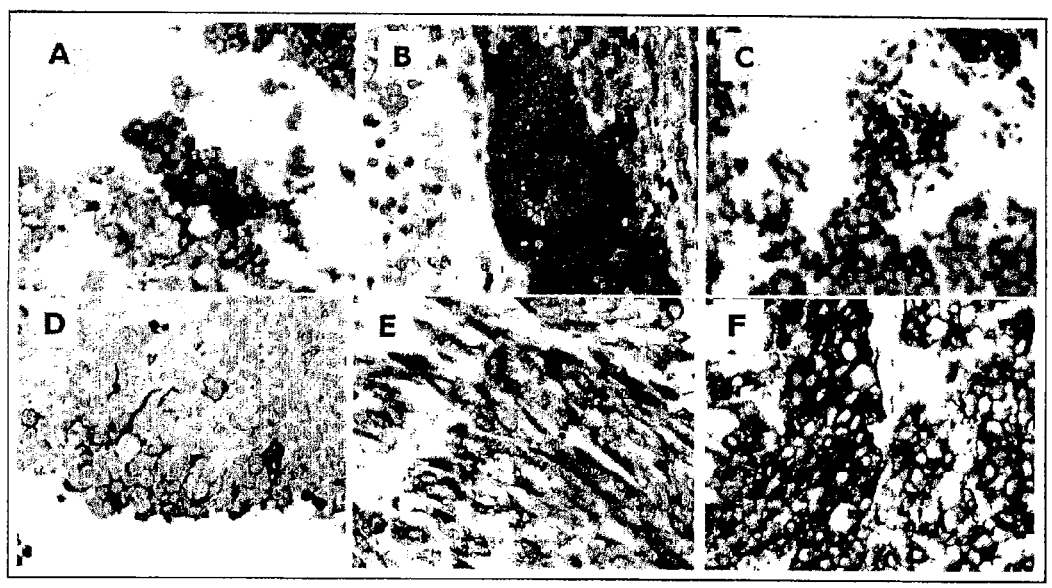
FIG. 16 shows representative photographs of VB3-011 immunohistochemical staining of neuroblastoma tissue (A-C) and melanoma tissue (D-F). Tissue sections are, (A)—Early stage neuroblastoma (Stage I, II, III non-N-myc amplified), 3+; (B)—Non-N-myc amplified Stage IV neuroblastoma, 2+; (C)—N-myc amplified Stage IV neuroblastoma, 3+. (D)—Early stage melanoma (Stage I-III), 3+; (E)—Stage IV melanoma, 3+; (F)—metastatic disease, 3+. All photographs are shown at 400× magnification.

A discrete nanospray head installed on a nanosource was used for the purpose. The collision energy was 48V, curtain gas and CAD gas were maintained at 25 and 6, respectively, and the sample allowed to cycle for 1.667 minutes (100 cycles) to obtain stable mass ion fragmentation. MS/MS fragmentation of two of the peptides (2402.978172−802.00000, 3+; 2134.985448−1068.500000, 2+) gave rise to the fragment ions shown in FIGS. 14 and 15. While one of the peptides, 'PELATAAGGYINGDAAVSEGYAADAF' (SEQ ID NO:7) from peptide mass 2402.97812, mapped 100% to a sequence from Scratch, peptide, RFLAAFLAAAGPFGFALGPSSV (SEQ ID NO:2), from peptide mass 2134.985448, showed 100% homology in the flanking sequences but not with the sequence in the middle, indicating an identification of a novel sequence. The presence of this sequence is responsible for the only transmembrane domain available on the protein. Mammalian Scratch sequence available in the database is a result of conceptual translation and does not have any transmembrane domains in the sequence. The protein sequence recovered shows 67% homology to the Mammalian Scratch protein available in the database and indicative of being present on the cell surface due to the presence of a transmembrane domain. Rest of the peptides derived from the spectra clearly matched the sequences from Mammalian Scratch, and therefore were pulled down as major hits. The ion fragmentation data further confirm the identity of a novel form of Scratch as the cognate antigen for VB3-011.

FIGS. 12 and 13 identify Mammalian Scratch as the antigen.

Discussion

VB3-011, an IgG MAb, was generated from peripheral blood lymphocytes (PBL) isolated from a patient diagnosed with a grade II astrocytoma, using Hybridomics™ and ImmunoMine™ Viventia's proprietary platform technologies (See WO97/044461). The antibody exhibits reactivity to a host of other cell lines each of which is representative of different cancer indications. Despite this demonstration of broad tumor-cell type reactivity, VB3-011 shows limited binding to normal tissue. VB3-011 antigen was classified as a "non-blottable" antigen with a glycan modification, attributable to CSA.

Since CSA molecules are characterized by (1-4) GlcNAc/Glucuronate structures they also resemble the lectin-Neu5Ac (α2→6) Gal(β1→4)Glucuronate, recognized by Hemagglutinin (HA). A new reagent that would enable lectin-based purification was generated using. recombinant HA was immobilized to anti-HA antibody as an purification agent. Membrane preparations were affinity purified with immobilized-HA, and the eluates subjected to SDS-PAGE and WB analysis, subsequently probed with VB3-011 antibody. VB3-011 detected a ~50 kDa protein on 1D-PAGE that further resolved into a ~36 kDa band on 2D-PAGE analysis. LC-MS/MS analysis of the 1D and 2D spots identified Mammalian Scratch as the antigen with molecular weight 36 kDa (of ~50 kDa observed by WB analysis of 1D-PAGE), thus attributing the rest to the presence of the glycan, 4-sulfated, Neu5Ac (α2→6) Gal(β1→4)Glucuronate. The detection of a 36 kDa spot on 2D-PAGE matched the molecular weight and isoelectric point [(pI), i.e., 9.7±0.2] characteristic of Mammalian Scratch.

The protein sequences recovered by denovo sequencing from MS/MS fragment ion analyses, resulted in 67% coverage with 16 out of 17 peptides showing 100% homology to the Mammalian Scratch sequence found in the database (gi|13775236). One peptide, RFLAAFLAAAGPFGFALGPSSV (SEQ ID NO:2), from peptide mass 2134.985448, showed 100% homology in the flanking sequences but not with the sequence in the middle, indicating an identification of a novel sequence. The presence of this sequence is responsible for the only transmembrane domain available on the protein and places Scratch on the cell-surface as opposed to the cytosol. This is the first report depicting Mammalian Scratch as a cell-surface tumor antigen.

Example 2

Tumor Associated Expression of Scratch

An antibody specific for Mammalian Scratch was tested for tumor specificity using HD formalin fixed TMA's. See Table 3 for normal tissues and Table 4 for tumor specific membrane binding. There was no detection of the Scratch antigen on the membrane of normal tissue. However, strongly positive membrane staining was found on a variety of tumor tissues.

Example 3

Localization of Scratch as Cancer Diagnostic

Aberrant localization of the scratch protein as an indicator of cancer: Wild type Scratch protein has a limited expression pattern within the nucleus of cells as described by Nakakura et al, 2001. However, expression in the case of the tumor tissue types and cancer cell types has been established on the membrane and within the cytoplasm of the cells by the inventors. Using techniques known in the art such as flow cytometery, immunohistochemistry, western blotting of membrane fractions of cells aberrant expression of the Scratch protein and variants thereof can be established on the membrane and within the cytoplasm of cancer cells. This change in localization can be used as a diagnostic indicative of cancer.

Membrane expression of variant Scratch proteins has been established by both flow cytometery and western blotting of membrane fractions from cancer cell types such as U-87Mg, A375, MDA-MB-435S, U118-MG. This is shown in Table 1, and FIGS. 3, 4 and 15.

Example 4

Detection of Variant mRNA as Indication of Cancer

RT-PCR methodology for sensitive detection of variant mRNA of Mammalian Scratch containing transmembrane domain: Messenger RNA will be isolated from different types of tumor cells and first strand complement DNA (cDNA) will be synthesized using the reverse transcriptase enzyme and an oligo dT primer. The cDNA will then be used to test for the expression of the wild type Scratch mRNA and possible variants and specifically the transmembrane mutant by PCR using the following primers:

```
5' Primer 1: for wt and variant
(corresponding to nucleotides 51 to 82)
                                    (SEQ ID NO: 26)
5'-GCC GAC CTG GAG AGC GCC TAC GGA CGC GCC 5' Primer 2: for transmembrane variant
(corresponding to nucleotides 76 to 105)
                                    (SEQ ID NO: 27)
5'-CGC GCC CGC TTX1 TTX2 GCX3 GCX3 TTX1 TTX2
GCX3
```

Where X1 is T or C, X2 is A or G and X3 is A, G, C, or T

```
3' Primer:
(corresponding to nucleotides 183 to 210)
                                    (SEQ ID NO: 28)
5'-TGC GTA CAT GGG CTC CGG CGA CGG CCC
```

The PCR reaction included a 50 µL reaction volume containing:

| | |
|---|---|
| 10X PCR buffer | 5 µL |
| 2 mM dNTPs | 5 µL |
| Primer 5' | 20 pmol |
| Primer 3' | 20 pmol |
| Taq DNA Polymerase | 2.5 U |
| DNA template | 50 ng |

The cycling conditions for PCR were: 94° C. for 1 min., 62° C. for 1 min., and 72° C. for 30 sec., for a total of 30 cycles followed by a final extension of 10 min. at 72° C.

Electrophoresis on a 1% agarose gel will demonstrate that the band of interest of 159 bp is present in reactions using primer 1 and 140 bp in reactions using primer 2 if the transmembrane mutant is present.

The sequence analysis of the wild type Mammalian Scratch revealed a KpnI restriction site (position 118) that is not present in the variant. Therefore, to test if the variant form is expressed in tumor cells, the amplified PCR product will be digested with the KpnI restriction enzyme followed electrophoresis on a 1.5% agarose gel. If the tumor cells express the wild type Mammalian Scratch, then two fragments of 67 and 92 bp will be detected under UV lamp. In contrast, if the tumor cells express a variant of Scratch, lacking the KpnI site then the size of the PCR fragment will be identical to the undigested control. Using the primers specific to the transmembrane region of the variant Mammalian Scratch (primer #2) a PCR fragment will only be found in samples containing the variant with the transmembrane domain, thereby identifying the specific variant.

Example 5

Detection of Genomic DNA Sequence as an Indication of Cancer

The gene coding for the human Mammalian Scratch protein has been located to chromosome 8 q24.3 and consists of 2 exons. The gene sequence for the cancer associated membrane bound variant of the Scratch can be easily determined using gene sequencing techniques known in the art such as exon-specific PCR amplification, or direct DNA sequencing initiating from primers to the known sequence.

Once the sequence of the mutated gene is known diagnostic tests based on its detection can be used to evaluate patients. DNA chip arrays can be created by attaching oligonucleotides corresponding to the sense and anti-sense sequences of both wild type and the mutated gene Genomic DNA can be isolated from the peripheral whole blood or from tumor tissues The gene of interest is then amplified using PCR with primers corresponding both to the wild type sequence and to the expected mutations and labeled with an appropriate probe (usually fluorescent). The DNA is then hybridized to the oligonucleotides on the chip and the pattern of fluorescence determined with a fluorescent reader. By comparing the pattern of fluorescence to a map of the known locations of the oligonucleotides sequences the sequence of the patients gene with can be established as either wild type or mutant. (Cooper et al 2004)

Arrays for common mutations in the p53 gene (Affymetrix) among others are already commercially available and custom array services are also available Example 6

Variant Cancer Associated Scratch as a Target for Immunotoxins

VB6-011 is a immunoconjugate of modified bouganin conjugate with an antibody that specifically recognizes Mammalian Scratch protein on the tumor cell surface. Treatment of cells expressing variant Scratch containing a transmembrane domain on the cell surface results in specific uptake of the immunoconjugate and subsequent cell death.

Cytotoxicity of VB6-011 Proteins

The cytotoxicity of VB6-011 was measured by an MTS assay. Briefly, antigen-positive and antigen-negative cells were seeded at 1000 cells per well and incubated at 37° C. for 3 hours. Subsequently, varying concentrations of VB6-011 and de-bouganin were added to the cells and after 5 days, the cell viability determined.

Figure 18:
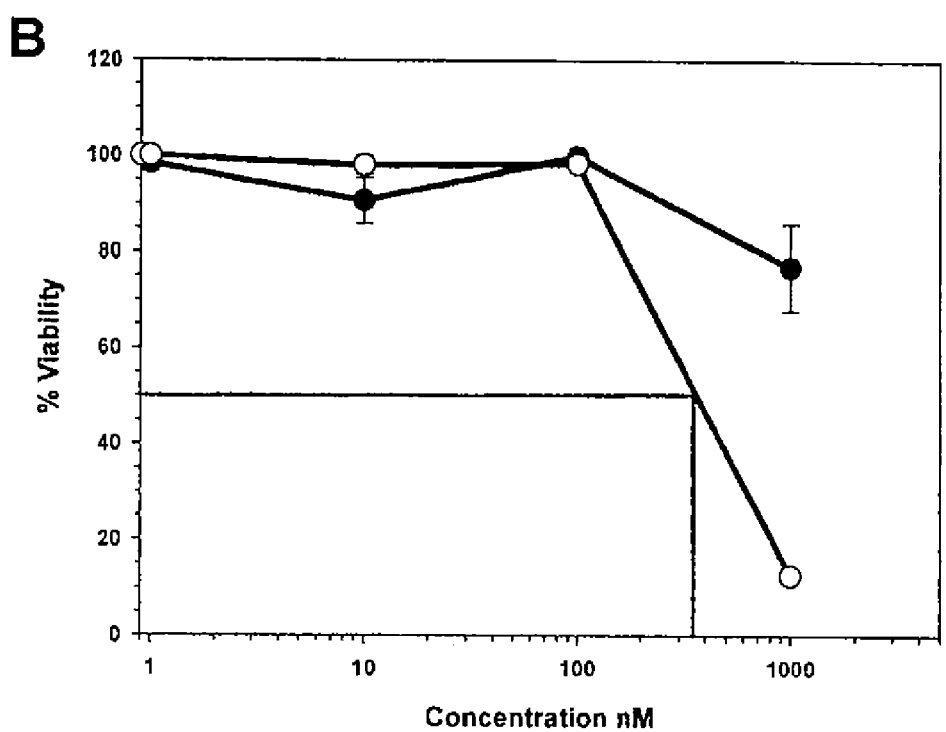
FIG. 18 shows the in vitro cytotoxicity of VB6-011 in an MTS assay of VB6-011 with antigen-positive cells MB-435S (open circle) and antigen-negative cells Panc-1 (black circle). Cells seeded at 1000 cells per well, were incubated with the Fab-de-bouganin purified proteins. After 5 days incubation, the cell viability was measured and $IC_{50}$ was determined.

The negative and positive-antigen cell lines were incubated with different concentrations of VB6-011 from 1 nM to 1 mM. After 5 days incubation, the calculated $IC_{50}$ of VB6-011 was 350 nM. (FIG. 18) (Table 5) In contrast, no $IC_{50}$ could be determined with the antigen negative cell lines.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Table 1: Increase in median fluorescence for VB3-011 over an isotype-matched control for each cell line used in the study.

| Cell line | MF* |
|---|---|
| A375 | 11.5 |
| U118MG | 6.1 |

TABLE 1-continued

Table 1: Increase in median fluorescence for VB3-011 over an isotype-matched control for each cell line used in the study.

| Cell line | MF* |
|---|---|
| U87MG | 4.6 |
| MDA-MB-435S | 4.6 |
| PANC-1 | 2.1 |
| DAUDI | 1.1 |

TABLE 2

| Start | End | Peptide mass | Description (Peptide sequence) |
|---|---|---|---|
| 28 | 50 | | A.RFLAAFLAAAGPFGFALGPSSV.Y (SEQ ID NO: 2) |
| 92 | 117 | | R.PELATAAGGYINGDAAVSEGYAADAF.F (SEQ ID NO: 7) |
| 4 | 8 | 592.7360 | R.SFLVK.K (SEQ ID NO: 8) |
| 12 | 26 | 1601.6900 | K.LDAFSSADLESAYGR.A (SEQ ID NO: 9) |
| 62 | 74 | 1345.5360 | K.GPSPEPMYAAAVR.G (SEQ ID NO: 10) |
| 75 | 123 | 4719.1140 | R.GELGPAAAGSAPPPTPRPELATAAGGYINGDAAVSEGYAADAFFITDGR.S (SEQ ID NO: 11) |
| 128 | 158 | 2457.4690 | K.ASNAGSAAAPSTASAAAPDGDAGGGGAGGR.S (SEQ ID NO: 12) |
| 159 | 167 | 786.8430 | R.SLGSGPGGR.G (SEQ ID NO: 13) |
| 172 | 179 | 731.7640 | R.AGAGTEAR.A (SEQ ID NO: 14) |
| 180 | 190 | 840.8940 | R.AGPGAAGAGGR.H (SEQ ID NO: 15) |
| 199 | 208 | 1099.1660 | K.TYATSSNLSR.H (SEQ ID NO: 16) |
| 215 | 222 | 888.9760 | R.SLDSQLAR.R (SEQ ID NO: 17) |
| 230 | 247 | 2085.5280 | K.VYVSMPAMAMHLLTHDLR.H (SEQ ID NO: 18) |
| 256 | 268 | 1598.8890 | K.AFSRPWLLQGHMR.S (SEQ ID NO: 19) |
| 284 | 288 | 578.6260 | K.AFADR.S (SEQ ID NO: 20) |
| 293 | 302 | 1157.3120 | R.AHMQTHSAFK.H (SEQ ID NO: 21) |
| 312 | 316 | 564.6820 | K.SFALK.S (SEQ ID NO: 22) |
| 317 | 321 | 623.7070 | K.SYLNK.H (SEQ ID NO: 23) |
| 330 | 348 | 1642.8320 | K.GGAGGPAAPAPPQLSPVQA. (SEQ ID NO: 24) |

Table 2: List of peptides along with their respective calculated masses obtained after the reconstruction step is as given in the above table.

TABLE 3

TMA assessment of Antigen Binding Fragment Reactivity with normal tissues by IHC

| Tissue | Location of Staining | Array # | Element | Score* | Comments |
|---|---|---|---|---|---|
| Adrenal | Cytoplasm | 1 | Cortex | + | Not Scored |
| | None | 1 & 2 | Medulla | 0 | |
| | Cytoplasm | 2 | Cortex | 1 | |
| Bone Marrow | None | 1 & 2 | Not Applicable | 0 | |
| Brain | None | 1 | Neurons | 0 | |
| | None | 2 | Neurons | Trace | |
| | Cytoplasm | 1 | Astrocytes | 1 | |
| | Cytoplasm | 2 | Astrocytes | Trace | |
| Breast | None | 1 & 2 | Not Applicable | 0 | |
| Cartilage | None | 1 & 2 | Not Applicable | 0 | |
| Colon | None | 1 & 2 | Not Applicable | 0 | |
| Heart | None | 1 & 2 | Not Applicable | 0 | |
| Kidney | None | 1 & 2 | Glomeruli | 0 | |
| | Cytoplasm | 1 & 2 | Tubules(Proximal & Distal) | 1 | |
| Liver | Cytoplasm | 1 & 2 | Hepatocytes | 1 | |
| | Cytoplasm | 1 | Bile ducts | 0 to 1+ | |
| | None | 2 | Bile ducts | 0 | |
| Lung | None | 1 & 2 | Not Applicable | 0 | |
| Ovary | None | 1 & 2 | Not Applicable | 0 | |
| Pancreas | Cytoplasm | 2 | Acini | 2 | Scattered cells |
| | Cytoplasm | 1 | Acini | Trace to 3+ | |
| | None | 1 & 2 | Ductal cells | 0 | |
| | None | 2 | Islet cells | 0 | |
| | Cytoplasm | 1 | Islet cells | Trace | |
| Peripheral Nerve | None | 1 & 2 | Not Applicable | 0 | |
| Prostate | None | 1 & 2 | Not Applicable | 0 | |
| Salivary Gland | Cytoplasm | 1 & 2 | Ductal cells | 1 | |
| | None | 1 & 2 | Acini | 0 | |
| Skeletal Muscle | None | 1 & 2 | Not Applicable | 0 | |
| Skin | None | 1 & 2 | Not Applicable | 0 | |
| Spleen | None | 1 & 2 | Not Applicable | 0 | |
| Stomach | None | 1 & 2 | Not Applicable | 0 | |
| Testis | Cytoplasm | 1 | Germ cells | Trace | |
| | None | 2 | Leydig cells | 0 | |
| | None | 2 | Germ cells | 0 | |
| | Cytoplasm | 1 | Leydig cells | 1 | |
| Thyroid | None | 1 & 2 | Not Applicable | 0 | |

*Scoring was evaluated on a 0-4+ scale, with 0 = no staining and trace being less than 1+ but greater than 0. Grades 1+ to 4+ represent increased intensity of staining, with 4+ being strong, dark brown staining.

TABLE 4

Tumor TMA analysis for Antigen Binding Fragment

| Tissue | Membrane staining | Score* | Comments |
|---|---|---|---|
| Lymphoma | 7/10 | 1 to 3+ | Strong membrane staining |
| Breast Carcinoma | 27/31 | 1 to 3+ | Strong membrane staining |
| Colon Carcinoma | 23/26 | 1 to 3+ | Prominent membrane reactivity |
| Melanoma | 13/14 | 1 to 3+ | Prominent membrane reactivity |
| Prostate Carcinoma | 17/20 | 1 to 2+ | Majority were strongly positive |
| Cervix Squamous Cell Carcinoma | 22/24 | 1 to 2+ | Majority - strongly positive |
| Cervix Adenocarcinoma | 9/9 | 1 to 2+ | Majority - strongly positive |
| Kaposi Sarcoma | 7/8 | 1 to 2+ | Majority were strongly positive |

*Scoring was evaluated on a 0-4+ scale, with 0 = no staining and trace being less than 1+ but greater than 0. Grades 1+ to 3+ represent increased intensity of staining, with 4+ being strong, dark brown staining.
nd: not determined.

TABLE 5

Biological characterization of VB6-011

| | Affinity (M) | VB6 Saturation conc. (µg/mL) | IgG concentration (µg/mL)* | IC$_{50}$ (nM) |
|---|---|---|---|---|
| VB6-011 | $2 \cdot 10^{-6}$ | 250 | 180 | 350 |

ND: not determined.
*Concentration of IgG that inhibits 50% of the VB6 binding.

References

1. Essentials of Glycobiology. Cold Spring Harbor, N.Y.: Cold Spring Harbor Press; 1999.
2. Altschul S F, Gish W, Miller W, Myers E W, Lipman D J. Basic local alignment search tool. J Mol. Biol. 1990; 215: 403-410.
3. Azumi K, Yokosawa H, Ishii S. Lipopolysaccharide induces release of a metallo-protease from hemocytes of the ascidian, Halocynthia roretzi. Dev. Comp Immunol. 1991; 15:1-7.
4. Baldari C, Murray J A, Ghiara P, Cesareni G, Galeotti C L. A novel leader peptide which allows efficient secretion of a fragment of human interleukin 1 beta in *Saccharomyces cerevisiae*. EMBO J 1987; 6:229-234.
5. Bartel D P, Szostak J W. Isolation of new ribozymes from a large pool of random sequences [see comment]. Science 1993; 261:1411-1418.

6. Bathe E, Sancho E, Franci C et al. The transcription factor snail is a repressor of E-cadherin gene expression in epithelial tumour cells. Nat Cell Biol. 2000; 2:84-89.
7. Brinster R L, Chen H Y, Trumbauer M E, Yagle M K, Palmiter R D. Factors affecting the efficiency of introducing foreign DNA into mice by microinjecting eggs. Proc Natl. Acad. Sci. U.S.A 1985; 82:4438-4442.
8. Carrillo H, Lipman D. The Multiple Sequence Alignment Problem in Biology. SIAM. J. Appl. Math. 1988; 48:1073-1082.
9. Cullen D, Gray G L, Wilson L J et al. Controlled Expression and Secretion of Bovine Chymosin in *Aspergillus Nidulans*. Nat Biotech 1987; 5:369-376.
10. Devereux J, Haeberli P, Smithies O. A comprehensive set of sequence analysis programs for the VAX. Nucleic Acids Res 1984; 12:387-395.
11. Finn P J, Gibson N J, Fallon R, Hamilton A, Brown T. Synthesis and properties of DNA-PNA chimeric oligomers. Nucleic Acids Res 1996; 24:3357-3363.
12. Frische K, Meldal M, Werdelin O et al. Multiple column synthesis of a library of T-cell stimulating Tn-antigenic glycopeptide analogues for the molecular characterization of T-cell-glycan specificity. J Pept. Sci. 1996; 2:212-222.
13. Gautier C, Morvan F, Rayner B et al. Alpha-DNA. IV: Alpha-anomeric and beta-anomeric tetrathymidylates covalently linked to intercalating oxazolopyridocarbazole. Synthesis, physicochemical properties and poly (rA) binding. Nucleic Acids Res 1987; 15:6625-6641.
14. Gennaro A R. Remington's Pharmaceutical Sciences. Easton, Pa.: Mack Publishing Company; 2000.
15. Goding J W. Monoclonal Antibodies: Principles and Practices.: Academic Press; 1986.
16. Goeddel D V. Systems for heterologous gene expression. Methods Enzymol. 1990; 185:3-7.
17. Grimes H L, Chan T O, Zweidler-McKay P A, Tong B, Tsichlis P N. The Gfi-1 proto-oncoprotein contains a novel transcriptional repressor domain, SNAG, and inhibits G1 arrest induced by interleukin-2 withdrawal. Mol. Cell Biol. 1996; 16:6263-6272.
18. Hammer R E, Brinster R L, Rosenfeld M G, Evans R M, Mayo K E. Expression of human growth hormone-releasing factor in transgenic mice results in increased somatic growth. Nature 1985; 315:413-416.
19. Haseloff J, Gerlach W L. Simple RNA enzymes with new and highly specific endoribonuclease activities. Nature 1988; 334:585-591.
20. Helene C. The anti-gene strategy: control of gene expression by triplex-forming-oligonucleotides. Anticancer Drug Des 1991; 6:569-584.
21. Helene C, Thuong N T, Harel-Bellan A. Control of gene expression by triple helix-forming oligonucleotides. The antigene strategy. Ann. N.Y. Acad. Sci. 1992; 660:27-36.
22. Hemavathy K, Guru S C, Harris J, Chen J D, Ip Y T. Human Slug is a repressor that localizes to sites of active transcription. Mol. Cell Biol. 2000; 20:5087-5095.
23. Henikoff S, Henikoff J G. Amino acid substitution matrices from protein blocks. Proc Natl. Acad. Sci. U.S.A 1992; 89:10915-10919.
24. Hinnen A, Hicks J B, Fink G R. Transformation of yeast. Proc Natl. Acad. Sci. U.S.A 1978; 75:1929-1933.
25. Huse W D, Sastry L, Iverson S A et al. Generation of a large combinatorial library of the immunoglobulin repertoire in phage lambda. Science 1989; 246:1275-1281.
26. Hyrup B, Nielsen P E. Peptide nucleic acids (PNA): synthesis, properties and potential applications. Bioorg. Med Chem 1996; 4:5-23.
27. Inoue H, Hayase Y, Imura A et al. Synthesis and hybridization studies on two complementary nona(2'-O-methyl) ribonucleotides. Nucleic Acids Res 1987; 15:6131-6148.
28. Inoue H, Hayase Y, Iwai S, Ohtsuka E. Sequence-dependent hydrolysis of RNA using modified oligonucleotide splints and RNase H. FEBS Lett. 1987; 215:327-330.
29. John Wiley & Sons. Current Protocols in Molecular Biology. New York, N.Y.: John Wiley & Sons; 2006.
30. Kataoka H, Murayama T, Yokode M et al. A novel snail-related transcription factor Smuc regulates basic helix-loop-helix transcription factor activities via specific E-box motifs. Nucleic Acids Res 2000; 28:626-633.
31. Kaufman R J, Murtha P, Davies M V. Translational efficiency of polycistronic mRNAs and their utilization to express heterologous genes in mammalian cells. EMBO J 1987; 6:187-193.
32. Kurjan J, Herskowitz I. Structure of a yeast pheromone gene (MF alpha): a putative alpha-factor precursor contains four tandem copies of mature alpha-factor. Cell 1982; 30:933-943.
33. Lemaitre M, Bayard B, Lebleu B. Specific antiviral activity of a polyp lysine)-conjugated oligodeoxyribonucleotide sequence complementary to vesicular stomatitis virus N protein mRNA initiation site. Proc Natl. Acad. Sci. U.S.A 1987; 84:648-652.
34. Lesk A. Computational Molecular Biology: Sources and Methods for Sequence Analysis. New York, N.Y.: Oxford University Press; 1988.
35. Letsinger R L, Zhang G R, Sun D K, Ikeuchi T, Sarin P S. Cholesteryl-conjugated oligonucleotides: synthesis, properties, and activity as inhibitors of replication of human immunodeficiency virus in cell culture. Proc Natl. Acad. Sci. U.S.A 1989; 86:6553-6556.
36. Luckow V A, Summers M D. High level expression of nonfused foreign genes with *Autographa californica* nuclear polyhedrosis virus expression vectors. Virology 1989; 170:31-39.
37. Mag M, Engels J W. Synthesis and selective cleavage of oligodeoxyribonucleotides containing non-chiral internucleotide phosphoramidate linkages. Nucleic Acids Res 1989; 17:5973-5988.
38. Maione T E, Gray G S, Hunt A J, Sharpe R J. Inhibition of tumor growth in mice by an analogue of platelet factor 4 that lacks affinity for heparin and retains potent angiostatic activity. Cancer Res 1991; 51:2077-2083.
39. McCafferty J, Griffiths A D, Winter G, Chiswell D J. Phage antibodies: filamentous phage displaying antibody variable domains. Nature 1990; 348:552-554.
40. Menozzi F D, Rouse J H, Alavi M et al. Identification of a heparin-binding hemagglutinin present in mycobacteria. J Exp. Med 1996; 184:993-1001.
41. Merrifield R B. Solid Phase Peptide Synthesis 3: An Improved Synthesis of Bradykinin. Biochemistry 1964; 3:1385-1390.
42. Nakakura E K, Watkins D N, Sriuranpong V et al. Mammalian Scratch participates in neuronal differentiation in P19 embryonal carcinoma cells. Brain Res. Mol. Brain Res. 2001; 95:162-166.
43. Nakakura E K, Watkins D N, Schuebel K E et al. Mammalian Scratch: a neural-specific Snail family transcriptional repressor. Proc. Natl. Acad. Sci. U.S.A 2001; 98:4010-4015.
44. Needleman S B, Wunsch C D. A general method applicable to the search for similarities in the amino acid sequence of two proteins. J Mol. Biol. 1970; 48:443-453.

45. Palmiter R D, Norstedt G, Gelinas R E, Hammer R E, Brinster R L. Metallothionein-human GH fusion genes stimulate growth of mice. Science 1983; 222:809-814.
46. Palmiter R D, Brinster R L. Transgenic mice. Cell 1985; 41:343-345.
47. Perry-O'Keefe H, Yao X W, Coull J M, Fuchs M, Egholm M. Peptide nucleic acid pre-gel hybridization: an alternative to southern hybridization. Proc Natl. Acad. Sci. U.S.A 1996; 93:14670-14675.
48. Petersen K H, Jensen D K, Egholm M, Nielsen P E, Buchardt O. A PNA-DNA linker synthesis of N-((4,4'-dimethoxytrityloxy)ethyl)-N-(thymin-1-ylacetyl)glycine. Bioorganic Med Chem Letts 1995; 5:1119-1124.
49. Prydz K, Dalen K T. Synthesis and sorting of proteoglycans. J Cell Sci. 2000; 113 Pt 2:193-205.
50. Sage E H, Bassuk J A, Yost J C, Folkman M J, Lane T F. Inhibition of endothelial cell proliferation by SPARC is mediated through a Ca(2+)-binding EF-hand sequence. J Cell Biochem. 1995; 57:127-140.
51. Sambrook J, MacCallum P, Russell D. Molecular Cloning: A Laboratory Manual: Cold Spring Harbor Laboratory Press; 2001.
52. Schultz L D, Tanner J, Hofmann K J et al. Expression and secretion in yeast of a 400-kDa envelope glycoprotein derived from Epstein-Barr virus. Gene 1987; 54:113-123.
53. Seed B. An LFA-3 cDNA encodes a phospholipid-linked membrane protein homologous to its receptor CD2. Nature 1987; 329:840-842.
54. Sinkar V P, White F F, Gordon M P. Molecular Biology of the RI Plasmid—A Review. J. Biosci. 1987; 11:47-57.
55. Smith G E, Summers M D, Fraser M J. Production of human beta interferon in insect cells infected with a baculovirus expression vector. Mol. Cell Biol. 1983; 3:2156-2165.
56. Smith T F, Waterman M S. Comparions of Biosequences. Advances in Applied Mathematics 1981; 2:482-489.
57. Sugahara K, Yamashina I, De W P, Van H H, Vliegenthart J F. Structural studies on sulfated glycopeptides from the carbohydrate-protein linkage region of chondroitin 4-sulfate proteoglycans of swarm rat chondrosarcoma. Demonstration of the structure Gal(4-O-sulfate)beta 1-3Gal beta 1-4XYL beta 1-O-Ser. J Biol. Chem 1988; 263:10168-10174.
58. Sugahara K, Masuda M, Harada T et al. Structural studies on sulfated oligosaccharides derived from the carbohydrate-protein linkage region of chondroitin sulfate proteoglycans of whale cartilage. Eur. J Biochem. 1991; 202: 805-811.
59. Therasse P, Arbuck S G, Eisenhauer E A et al. New guidelines to evaluate the response to treatment in solid tumors. European Organization for Research and Treatment of Cancer, National Cancer Institute of the United States, National Cancer Institute of Canada. J Natl. Cancer Inst. 2000; 92:205-216.
60. Thompson J D, Higgins D G, Gibson T J. CLUSTAL W: improving the sensitivity of progressive multiple sequence alignment through sequence weighting, position-specific gap penalties and weight matrix choice. Nucleic Acids Res 1994; 22:4673-4680.
61. Tolsma S S, Volpert O V, Good D J et al. Peptides derived from two separate domains of the matrix protein thrombospondin-1 have anti-angiogenic activity. J Cell Biol. 1993; 122:497-511.
62. van der Krol A R, Mol J N, Stuitje A R. Modulation of eukaryotic gene expression by complementary RNA or DNA sequences. Biotechniques 1988; 6:958-976.
63. Wansch Eed. Houben-Weyl: Methods of Organic Chemistry. Stuttgart: Thieme; 1987.
64. Ward E S, Gussow D, Griffiths A D, Jones P T, Winter G. Binding activities of a repertoire of single immunoglobulin variable domains secreted from *Escherichia coli*. Nature 1989; 341:544-546.
65. World Health Organization. World Cancer Report. Geneva, Switzerland: WHO Press; 2003.
66. Zambryski P, Herrerra-Estrella L, DeBlock M, Van Montagu M. In: Setlow J, Hollaender A, eds. Genetic Engineering: Principles and Methods. Vol 6. New York, N.Y.: Plenum Press; 1984:253-278.
67. Zhang Z, Gildersleeve J, Yang Y Y et al. A new strategy for the synthesis of glycoproteins. Science 2004; 303:371-373.
68. Zon G. Oligonucleotide analogues as potential chemotherapeutic agents. Pharm. Res 1988; 5:539-549.

We claim:

1. A method of detecting cancer cells or monitoring cancer in a subject having or suspected of having cancer, comprising detecting a cancer-associated variant of Mammalian Scratch, wherein the cancer-associated variant of Mammalian Scratch comprises a transmembrane domain comprising the amino acid sequence as shown in SEQ ID NO:2, on a cell in a sample from the subject, wherein cancer is indicated, if the cancer-associated variant of Mammalian Scratch is detected on the cell.

2. A method of detecting cancer cells or monitoring cancer in a subject having or suspected of having cancer comprising:
   (a) contacting a sample from the subject with an antibody that binds to a cancer-associated variant of Mammalian Scratch comprising a transmembrane domain comprising the amino acid sequence as shown in SEQ ID NO:2;
   (b) detecting the level of the cancer-associated variant of Mammalian Scratch in the sample; and
   (c) comparing the level of the cancer-associated variant of Mammalian Scratch in the sample to a control sample, wherein increased levels of the cancer-associated variant of Mammalian Scratch as compared to the control indicates that the subject has cancer.

3. A method of detecting cancer cells or monitoring cancer in a subject having or suspected of having cancer, comprising detecting a cancer-associated variant of Mammalian Scratch comprising the amino acid sequence as shown in SEQ ID NO:1, wherein the cancer-associated variant of Mammalian Scratch comprises a transmembrane domain, on a cell in a sample from the subject, wherein cancer is indicated, if the cancer-associated variant of Mammalian Scratch is detected on the cell.

4. A method of detecting cancer cells or monitoring cancer in a subject having or suspected of having cancer comprising:

(a) contacting a sample from the subject with an antibody that binds to a cancer-associated variant of Mammalian Scratch comprising the amino acid sequence as shown in SEQ ID NO:1;

(b) detecting the level of the cancer-associated variant of Mammalian Scratch in the sample; and (c) comparing the level of the cancer-associated variant of Mammalian Scratch in the sample to a control sample, wherein increased levels of the cancer-associated variant of Mammalian Scratch as compared to the control indicates that the subject has cancer.

* * * * *

SEQUENCE LISTING

```
<160> NUMBER OF SEQ ID NOS: 28

<210> SEQ ID NO 1
<211> LENGTH: 347
<212> TYPE: PRT
<213> ORGANISM: Homo sapiens

<400> SEQUENCE: 1

Met Pro Arg Ser Phe Leu Val Lys Lys Val Lys Leu Asp Ala Phe Ser
1               5                   10                  15

Ser Ala Asp Leu Glu Ser Ala Tyr Gly Arg Ala Arg Phe Leu Ala Ala
            20                  25                  30

Phe Leu Ala Ala Ala Gly Pro Phe Gly Phe Ala Leu Gly Pro Ser Ser
        35                  40                  45

Val Tyr Asp Gly Asp Ala Glu Ala Ala Leu Leu Lys Gly Pro Ser Pro
    50                  55                  60

Glu Pro Met Tyr Ala Ala Ala Val Arg Gly Glu Leu Gly Pro Ala Ala
65                  70                  75                  80
```

```
Ala Gly Ser Ala Pro Pro Thr Pro Arg Pro Glu Leu Ala Thr Ala
                85                  90                  95

Ala Gly Gly Tyr Ile Asn Gly Asp Ala Val Ser Glu Gly Tyr Ala
            100                 105                 110

Ala Asp Ala Phe Phe Ile Thr Asp Gly Arg Ser Arg Lys Ala Ser
        115                 120                 125

Asn Ala Gly Ser Ala Ala Pro Ser Thr Ala Ser Ala Ala Pro
    130                 135                 140

Asp Gly Asp Ala Gly Gly Gly Ala Gly Gly Arg Ser Leu Gly
145                 150                 155                 160

Ser Gly Pro Gly Gly Arg Gly Thr Arg Ala Gly Ala Gly Thr Glu
                165                 170                 175

Ala Arg Ala Gly Pro Gly Ala Ala Gly Ala Gly Gly Arg His Ala Cys
            180                 185                 190

Gly Glu Cys Gly Lys Thr Tyr Ala Thr Ser Ser Asn Leu Ser Arg His
            195                 200                 205

Lys Gln Thr His Arg Ser Leu Asp Ser Gln Leu Ala Arg Arg Cys Pro
            210                 215                 220

Thr Cys Gly Lys Val Tyr Val Ser Met Pro Ala Met Ala Met His Leu
225                 230                 235                 240

Leu Thr His Asp Leu Arg His Lys Cys Gly Val Cys Gly Lys Ala Phe
                245                 250                 255

Ser Arg Pro Trp Leu Leu Gln Gly His Met Arg Ser His Thr Gly Glu
            260                 265                 270

Lys Pro Phe Gly Cys Ala His Cys Gly Lys Ala Phe Ala Asp Arg Ser
            275                 280                 285

Asn Leu Arg Ala His Met Gln Thr His Ser Ala Phe Lys His Phe Gln
    290                 295                 300

Cys Lys Arg Cys Lys Lys Ser Phe Ala Leu Lys Ser Tyr Leu Asn Lys
305                 310                 315                 320

His Tyr Glu Ser Ala Cys Phe Lys Gly Gly Ala Gly Pro Ala Ala
                325                 330                 335

Pro Ala Pro Pro Gln Leu Ser Pro Val Gln Ala
            340                 345

<210> SEQ ID NO 2
<211> LENGTH: 24
<212> TYPE: PRT
<213> ORGANISM: Homo sapiens

<400> SEQUENCE: 2

Ala Arg Phe Leu Ala Ala Phe Leu Ala Ala Ala Gly Pro Phe Gly Phe
1               5                   10                  15

Ala Leu Gly Pro Ser Ser Val Tyr
            20

<210> SEQ ID NO 3
<211> LENGTH: 348
<212> TYPE: PRT
<213> ORGANISM: Homo sapiens

<400> SEQUENCE: 3

Met Pro Arg Ser Phe Leu Val Lys Lys Val Lys Leu Asp Ala Phe Ser
1               5                   10                  15

Ser Ala Asp Leu Glu Ser Ala Tyr Gly Arg Ala Arg Ser Asp Leu Gly
            20                  25                  30

Ala Pro Leu His Asp Lys Gly Tyr Leu Ser Asp Tyr Val Gly Pro Ser
```

-continued

```
                35                  40                  45
Ser Val Tyr Asp Gly Asp Ala Glu Ala Leu Leu Lys Gly Pro Ser
 50                  55                  60

Pro Glu Pro Met Tyr Ala Ala Val Arg Gly Glu Leu Gly Pro Ala
 65                  70                  75                  80

Ala Ala Gly Ser Ala Pro Pro Thr Pro Arg Pro Glu Leu Ala Thr
                 85                  90                  95

Ala Ala Gly Gly Tyr Ile Asn Gly Asp Ala Ala Val Ser Glu Gly Tyr
                100                 105                 110

Ala Ala Asp Ala Phe Phe Ile Thr Asp Gly Arg Ser Arg Lys Ala
                115                 120                 125

Ser Asn Ala Gly Ser Ala Ala Pro Ser Thr Ala Ser Ala Ala
130                 135                 140

Pro Asp Gly Asp Ala Gly Gly Gly Gly Ala Gly Gly Arg Ser Leu
145                 150                 155                 160

Gly Ser Gly Pro Gly Arg Gly Gly Thr Arg Ala Gly Ala Gly Thr
                165                 170                 175

Glu Ala Arg Ala Gly Pro Gly Ala Ala Gly Ala Gly Gly Arg His Ala
                180                 185                 190

Cys Gly Glu Cys Gly Lys Thr Tyr Ala Thr Ser Ser Asn Leu Ser Arg
                195                 200                 205

His Lys Gln Thr His Arg Ser Leu Asp Ser Gln Leu Ala Arg Arg Cys
                210                 215                 220

Pro Thr Cys Gly Lys Val Tyr Val Ser Met Pro Ala Met Ala Met His
225                 230                 235                 240

Leu Leu Thr His Asp Leu Arg His Lys Cys Gly Val Cys Gly Lys Ala
                245                 250                 255

Phe Ser Arg Pro Trp Leu Leu Gln Gly His Met Arg Ser His Thr Gly
                260                 265                 270

Glu Lys Pro Phe Gly Cys Ala His Cys Gly Lys Ala Phe Ala Asp Arg
                275                 280                 285

Ser Asn Leu Arg Ala His Met Gln Thr His Ser Ala Phe Lys His Phe
                290                 295                 300

Gln Cys Lys Arg Cys Lys Lys Ser Phe Ala Leu Lys Ser Tyr Leu Asn
305                 310                 315                 320

Lys His Tyr Glu Ser Ala Cys Phe Lys Gly Ala Gly Gly Pro Ala
                325                 330                 335

Ala Pro Ala Pro Pro Gln Leu Ser Pro Val Gln Ala
                340                 345
```

<210> SEQ ID NO 4
<211> LENGTH: 164
<212> TYPE: PRT
<213> ORGANISM: Homo sapiens

<400> SEQUENCE: 4

```
Ala Gly Ala Gly Gly Arg His Ala Cys Gly Glu Cys Gly Lys Thr Tyr
 1                 5                  10                  15

Ala Thr Ser Ser Asn Leu Ser Arg His Lys Gln Thr His Arg Ser Leu
                20                  25                  30

Asp Ser Gln Leu Ala Arg Arg Cys Pro Thr Cys Gly Lys Val Tyr Val
                35                  40                  45

Ser Met Pro Ala Met Ala Met His Leu Leu Thr His Asp Leu Arg His
 50                  55                  60

Lys Cys Gly Val Cys Gly Lys Ala Phe Ser Arg Pro Trp Leu Leu Gln
```

```
                65                  70                  75                  80
Gly His Met Arg Ser His Thr Gly Glu Lys Pro Phe Gly Cys Ala His
                        85                  90                  95
Cys Gly Lys Ala Phe Ala Asp Arg Ser Asn Leu Arg Ala His Met Gln
                100                 105                 110
Thr His Ser Ala Phe Lys His Phe Gln Cys Lys Arg Cys Lys Lys Ser
            115                 120                 125
Phe Ala Leu Lys Ser Tyr Leu Asn Lys His Tyr Glu Ser Ala Cys Phe
        130                 135                 140
Lys Gly Gly Ala Gly Gly Pro Ala Ala Pro Ala Pro Pro Gln Leu Ser
145                 150                 155                 160
Pro Val Gln Ala

<210> SEQ ID NO 5
<211> LENGTH: 1047
<212> TYPE: DNA
<213> ORGANISM: Homo sapiens

<400> SEQUENCE: 5
atgcccaggt ccttcctggt caagaaggtc aaacttgacg cgttctcttc ggccgacctg      60
gagagcgcct acggacgcgc ccgcagcgac ctcggcgcgc cactgcacga taaagggtac     120
ctcagcgact acgtggggcc ctcgtccgtc tacgatggcg acgccgaggc tgcgctgctc     180
aaagggccgt cgccggagcc catgtacgca gcagctgtgc gtggagagct gggtccggcg     240
gctgcagggt ctgcgccgcc gcccaccccg cgcccggagc tggccaccgc tgcgggcggc     300
tacatcaacg gcgacgcggc cgtcagcgag ggctacgcgg cggacgcctt cttcatcacc     360
gacgggcgct cgcggcgtaa gcttccaat gccggctctg ccgccgctcc ctccacagcc     420
tcggcggcgg ccccgacgg cgacgccgga ggcggggcg gggcgggcgg gcgcagcttg      480
ggatccgggc cggggggccg gggcggcacg cgcgcgggg caggcaccga ggcgcgcgcg     540
gggccagggg ccgcaggtgc tggcggccgg cacgcgtgcg gcgagtgcgg caaaacatac     600
gccacgtcgt cgaacctgag ccgccacaag cagacgcacc gcagcctgga cagccagctg     660
gcgcggcgct gcccgacgtg cggcaaggtg tacgtgtcca tgccggccat ggccatgcac     720
ctgctcacgc acgacctgcg ccacaagtgc ggcgtgtgcg gcaaagcctt ctcgcggccc     780
tggctgctgc agggccacat gcgctcgcac accggcgaga aacccttcgg ctgcgcgcac     840
tgcggcaagg ccttcgccga ccgctccaac ctgcgcgcgc acatgcagac gcattcggcc     900
ttcaagcact ccagtgcaa cgctgcaag aagagcttcg cgctcaagtc ctatctcaac     960
aagcactacg agtcggcctg cttcaagggc ggcgccggag cccgcgcggc tcctgcgccg    1020
ccacagctca gccctgtgca ggcctag                                        1047

<210> SEQ ID NO 6
<211> LENGTH: 1044
<212> TYPE: DNA
<213> ORGANISM: Homo sapiens
<220> FEATURE:
<221> NAME/KEY: misc_feature
<222> LOCATION: (87)..(87)
<223> OTHER INFORMATION: n = t or c
<220> FEATURE:
<221> NAME/KEY: misc_feature
<222> LOCATION: (90)..(90)
<223> OTHER INFORMATION: n = g or a
<220> FEATURE:
<221> NAME/KEY: misc_feature
<222> LOCATION: (93)..(93)
<223> OTHER INFORMATION: n = a, t, g or c
```

```
<220> FEATURE:
<221> NAME/KEY: misc_feature
<222> LOCATION: (96)..(96)
<223> OTHER INFORMATION: n = a, t, g or c
<220> FEATURE:
<221> NAME/KEY: misc_feature
<222> LOCATION: (99)..(99)
<223> OTHER INFORMATION: n = t or c
<220> FEATURE:
<221> NAME/KEY: misc_feature
<222> LOCATION: (102)..(102)
<223> OTHER INFORMATION: n = g or a
<220> FEATURE:
<221> NAME/KEY: misc_feature
<222> LOCATION: (105)..(105)
<223> OTHER INFORMATION: n = a, t, g or c
<220> FEATURE:
<221> NAME/KEY: misc_feature
<222> LOCATION: (108)..(108)
<223> OTHER INFORMATION: n = a, t, g or c
<220> FEATURE:
<221> NAME/KEY: misc_feature
<222> LOCATION: (111)..(111)
<223> OTHER INFORMATION: n = a, t, g or c
<220> FEATURE:
<221> NAME/KEY: misc_feature
<222> LOCATION: (114)..(114)
<223> OTHER INFORMATION: n = a, t, g or c
<220> FEATURE:
<221> NAME/KEY: misc_feature
<222> LOCATION: (117)..(117)
<223> OTHER INFORMATION: n = a, t, g or c
<220> FEATURE:
<221> NAME/KEY: misc_feature
<222> LOCATION: (120)..(120)
<223> OTHER INFORMATION: n = t or c
<220> FEATURE:
<221> NAME/KEY: misc_feature
<222> LOCATION: (123)..(123)
<223> OTHER INFORMATION: n = a, t, g or c
<220> FEATURE:
<221> NAME/KEY: misc_feature
<222> LOCATION: (126)..(126)
<223> OTHER INFORMATION: n = t or c
<220> FEATURE:
<221> NAME/KEY: misc_feature
<222> LOCATION: (129)..(129)
<223> OTHER INFORMATION: n = a, t, g or c
<220> FEATURE:
<221> NAME/KEY: misc_feature
<222> LOCATION: (132)..(132)
<223> OTHER INFORMATION: n = g or a

<400> SEQUENCE: 6
atgcccaggt ccttcctggt caagaaggtc aaacttgacg cgttctcttc ggccgacctg      60
gagagcgcct acggacgcgc ccgcttnttn gcngcnttnt tngcngcngc nggnccnttn     120
ggnttngcnt tngggccctc gtccgtctac gatggcgacg ccgaggctgc gctgctcaaa     180
gggccgtcgc cggagcccat gtacgcagca gctgtgcgtg gagagctggg tccggcggct     240
gcagggtctg cgccgccgcc caccccgcgc ccggagctgg ccaccgctgc gggcggctac     300
atcaacggcg acgcggccgt cagcgagggc tacgcggcgg acgccttctt catcaccgac     360
gggcgctcgc ggcgtaaggc ttccaatgcc ggctctgccg ccgctccctc cacagcctcg     420
gcggcggccc ccgacggcga cgccggaggc ggggcgggg cggcgggcg cagcttggga     480 tccgggccgg ggggcggggg cggcacgcgc gcggggcag gcaccgaggc gcgcgcgggg     540
ccaggggccg caggtgctgg cggccggcac gcgtgcggc agtgcggcaa acatacgcc     600 acgtcgtcga acctgagccg ccacaagcag acgcaccgca gcctggacag ccagctggcg     660
cggcgctgcc cgacgtgcgg caaggtgtac cgtgtccatg cggccatggc catgcacctg     720
ctcacgcacg acctgcgcca caagtgcggc gtgtgcggca agccttctc gcggccctgg     780
```

```
ctgctgcagg gccacatgcg ctcgcacacc ggcgagaaac ccttcggctg cgcgcactgc      840
ggcaaggcct tcgccgaccg ctccaacctg cgcgcgcaca tgcagacgca ttcggccttc      900
aagcacttcc agtgcaagcg ctgcaagaag agcttcgcgc tcaagtccta tctcaacaag      960
cactacgagt cggcctgctt caagggcggc gccggaggcc ccgcggctcc tgcgccgcca     1020
cagctcagcc ctgtgcaggc ctag                                            1044
```

```
<210> SEQ ID NO 7
<211> LENGTH: 28
<212> TYPE: PRT
<213> ORGANISM: Homo sapiens

<400> SEQUENCE: 7

Arg Pro Glu Leu Ala Thr Ala Ala Gly Gly Tyr Ile Asn Gly Asp Ala
1               5                   10                  15

Ala Val Ser Glu Gly Tyr Ala Ala Asp Ala Phe Phe
            20                  25

<210> SEQ ID NO 8
<211> LENGTH: 7
<212> TYPE: PRT
<213> ORGANISM: Homo sapiens

<400> SEQUENCE: 8

Arg Ser Phe Leu Val Lys Lys
1               5

<210> SEQ ID NO 9
<211> LENGTH: 17
<212> TYPE: PRT
<213> ORGANISM: Homo sapiens

<400> SEQUENCE: 9

Lys Leu Asp Ala Phe Ser Ser Ala Asp Leu Glu Ser Ala Tyr Gly Arg
1               5                   10                  15

Ala

<210> SEQ ID NO 10
<211> LENGTH: 15
<212> TYPE: PRT
<213> ORGANISM: Homo sapiens

<400> SEQUENCE: 10

Lys Gly Pro Ser Pro Glu Pro Met Tyr Ala Ala Ala Val Arg Gly
1               5                   10                  15

<210> SEQ ID NO 11
<211> LENGTH: 51
<212> TYPE: PRT
<213> ORGANISM: Homo sapiens

<400> SEQUENCE: 11

Arg Gly Glu Leu Gly Pro Ala Ala Ala Gly Ser Ala Pro Pro Thr
1               5                   10                  15

Pro Arg Pro Glu Leu Ala Thr Ala Ala Gly Gly Tyr Ile Asn Gly Asp
            20                  25                  30

Ala Ala Val Ser Glu Gly Tyr Ala Ala Asp Ala Phe Phe Ile Thr Asp
            35                  40                  45

Gly Arg Ser
        50
```

```
<210> SEQ ID NO 12
<211> LENGTH: 33
<212> TYPE: PRT
<213> ORGANISM: Homo sapiens

<400> SEQUENCE: 12

Lys Ala Ser Asn Ala Gly Ser Ala Ala Pro Ser Thr Ala Ser Ala
1               5                   10                  15

Ala Ala Pro Asp Gly Asp Ala Gly Gly Gly Gly Ala Gly Gly Arg
            20                  25                  30

Ser

<210> SEQ ID NO 13
<211> LENGTH: 11
<212> TYPE: PRT
<213> ORGANISM: Homo sapiens

<400> SEQUENCE: 13

Arg Ser Leu Gly Ser Gly Pro Gly Gly Arg Gly
1               5                   10

<210> SEQ ID NO 14
<211> LENGTH: 10
<212> TYPE: PRT
<213> ORGANISM: Homo sapiens

<400> SEQUENCE: 14

Arg Ala Gly Ala Gly Thr Glu Ala Arg Ala
1               5                   10

<210> SEQ ID NO 15
<211> LENGTH: 13
<212> TYPE: PRT
<213> ORGANISM: Homo sapiens

<400> SEQUENCE: 15

Arg Ala Gly Pro Gly Ala Ala Gly Ala Gly Gly Arg His
1               5                   10

<210> SEQ ID NO 16
<211> LENGTH: 12
<212> TYPE: PRT
<213> ORGANISM: Homo sapiens

<400> SEQUENCE: 16

Lys Thr Tyr Ala Thr Ser Ser Asn Leu Ser Arg His
1               5                   10

<210> SEQ ID NO 17
<211> LENGTH: 10
<212> TYPE: PRT
<213> ORGANISM: Homo sapiens

<400> SEQUENCE: 17

Arg Ser Leu Asp Ser Gln Leu Ala Arg Arg
1               5                   10

<210> SEQ ID NO 18
<211> LENGTH: 20
<212> TYPE: PRT
<213> ORGANISM: Homo sapiens

<400> SEQUENCE: 18

Lys Val Tyr Val Ser Met Pro Ala Met Ala Met His Leu Leu Thr His
```

```
                1               5              10              15

Asp Leu Arg His
            20

<210> SEQ ID NO 19
<211> LENGTH: 15
<212> TYPE: PRT
<213> ORGANISM: Homo sapiens

<400> SEQUENCE: 19

Lys Ala Phe Ser Arg Pro Trp Leu Leu Gln Gly His Met Arg Ser
1               5                  10                  15

<210> SEQ ID NO 20
<211> LENGTH: 7
<212> TYPE: PRT
<213> ORGANISM: Homo sapiens

<400> SEQUENCE: 20

Lys Ala Phe Ala Asp Arg Ser
1               5

<210> SEQ ID NO 21
<211> LENGTH: 12
<212> TYPE: PRT
<213> ORGANISM: Homo sapiens

<400> SEQUENCE: 21

Arg Ala His Met Gln Thr His Ser Ala Phe Lys His
1               5                  10

<210> SEQ ID NO 22
<211> LENGTH: 7
<212> TYPE: PRT
<213> ORGANISM: Homo sapiens

<400> SEQUENCE: 22

Lys Ser Phe Ala Leu Lys Ser
1               5

<210> SEQ ID NO 23
<211> LENGTH: 7
<212> TYPE: PRT
<213> ORGANISM: Homo sapiens

<400> SEQUENCE: 23

Lys Ser Tyr Leu Asn Lys His
1               5

<210> SEQ ID NO 24
<211> LENGTH: 20
<212> TYPE: PRT
<213> ORGANISM: Homo sapiens

<400> SEQUENCE: 24

Lys Gly Gly Ala Gly Gly Pro Ala Ala Pro Ala Pro Pro Gln Leu Ser
1               5                  10                  15

Pro Val Gln Ala
            20

<210> SEQ ID NO 25
<211> LENGTH: 66
<212> TYPE: DNA
<213> ORGANISM: Homo sapiens
<220> FEATURE:
```

```
<221> NAME/KEY: misc_feature
<222> LOCATION: (6)..(6)
<223> OTHER INFORMATION: n = t or c
<220> FEATURE:
<221> NAME/KEY: misc_feature
<222> LOCATION: (9)..(9)
<223> OTHER INFORMATION: n = g or a
<220> FEATURE:
<221> NAME/KEY: misc_feature
<222> LOCATION: (12)..(12)
<223> OTHER INFORMATION: n = a, t, g or c
<220> FEATURE:
<221> NAME/KEY: misc_feature
<222> LOCATION: (15)..(15)
<223> OTHER INFORMATION: n = a, t, g or c
<220> FEATURE:
<221> NAME/KEY: misc_feature
<222> LOCATION: (18)..(18)
<223> OTHER INFORMATION: n = t or c
<220> FEATURE:
<221> NAME/KEY: misc_feature
<222> LOCATION: (21)..(21)
<223> OTHER INFORMATION: n = g or a
<220> FEATURE:
<221> NAME/KEY: misc_feature
<222> LOCATION: (24)..(24)
<223> OTHER INFORMATION: n = a, t, g or c
<220> FEATURE:
<221> NAME/KEY: misc_feature
<222> LOCATION: (27)..(27)
<223> OTHER INFORMATION: n = a, t, g or c
<220> FEATURE:
<221> NAME/KEY: misc_feature
<222> LOCATION: (30)..(30)
<223> OTHER INFORMATION: n = a, t, g or c
<220> FEATURE:
<221> NAME/KEY: misc_feature
<222> LOCATION: (33)..(33)
<223> OTHER INFORMATION: n = a, t, g or c
<220> FEATURE:
<221> NAME/KEY: misc_feature
<222> LOCATION: (36)..(36)
<223> OTHER INFORMATION: n = a, t, g or c
<220> FEATURE:
<221> NAME/KEY: misc_feature
<222> LOCATION: (39)..(39)
<223> OTHER INFORMATION: n = t or c
<220> FEATURE:
<221> NAME/KEY: misc_feature
<222> LOCATION: (42)..(42)
<223> OTHER INFORMATION: n = a, t, g or c
<220> FEATURE:
<221> NAME/KEY: misc_feature
<222> LOCATION: (45)..(45)
<223> OTHER INFORMATION: n = t or c
<220> FEATURE:
<221> NAME/KEY: misc_feature
<222> LOCATION: (48)..(48)
<223> OTHER INFORMATION: n = a, t, g or c
<220> FEATURE:
<221> NAME/KEY: misc_feature
<222> LOCATION: (51)..(51)
<223> OTHER INFORMATION: n = g or a

<400> SEQUENCE: 25
cgcttnttng cngcnttntt ngcngcngcn ggnccnttng gnttngcntt ngggccctcg      60
tccgtc                                                                66

<210> SEQ ID NO 26
<211> LENGTH: 30
<212> TYPE: DNA
<213> ORGANISM: Artificial sequence
<220> FEATURE:
<223> OTHER INFORMATION: primer

<400> SEQUENCE: 26
```

-continued

```
gccgacctgg agagcgccta cggacgcgcc                                    30

<210> SEQ ID NO 27
<211> LENGTH: 30
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (12)..(12)
<223> OTHER INFORMATION: n = t or c
<220> FEATURE:
<221> NAME/KEY: misc_feature
<222> LOCATION: (15)..(15)
<223> OTHER INFORMATION: n = g or a
<220> FEATURE:
<221> NAME/KEY: misc_feature
<222> LOCATION: (18)..(18)
<223> OTHER INFORMATION: n = a, t, g or c
<220> FEATURE:
<221> NAME/KEY: misc_feature
<222> LOCATION: (21)..(21)
<223> OTHER INFORMATION: n = a, t, g or c
<220> FEATURE:
<221> NAME/KEY: misc_feature
<222> LOCATION: (24)..(24)
<223> OTHER INFORMATION: n = t or c
<220> FEATURE:
<221> NAME/KEY: misc_feature
<222> LOCATION: (27)..(27)
<223> OTHER INFORMATION: n = g or a
<220> FEATURE:
<221> NAME/KEY: misc_feature
<222> LOCATION: (30)..(30)
<223> OTHER INFORMATION: n = a, t, g or c

<400> SEQUENCE: 27
cgcgcccgct tnttngcngc nttnttngcn                                    30

<210> SEQ ID NO 28
<211> LENGTH: 27
<212> TYPE: DNA
<213> ORGANISM: Artificial sequence
<220> FEATURE:
<223> OTHER INFORMATION: primer

<400> SEQUENCE: 28
tgcgtacatg ggctccggcg acggccc                                       27
```